United States Patent
Wainwright et al.

(10) Patent No.: US 10,324,036 B2
(45) Date of Patent: *Jun. 18, 2019

(54) POROUS PLANAR CELL CAPTURE SYSTEM

(71) Applicants: Charles River Laboratories, Inc., Wilmington, MA (US); ReaMetrix Inc., San Carlos, CA (US)

(72) Inventors: Norman R. Wainwright, Johns Island, SC (US); Bala S. Manian, Los Altos Hills, CA (US); Eric Stimpson, Charleston, SC (US); Brian J. Kolonia, Walnutport, PA (US); Robert K. Kolonia, Milford, NJ (US)

(73) Assignees: Charles River Laboratories, Inc., Wilmington, MA (US); ReaMetrix Inc., San Carlos, CA (US)

( * ) Notice: Subject to any disclaimer, the term of this patent is extended or adjusted under 35 U.S.C. 154(b) by 320 days.

This patent is subject to a terminal disclaimer.

(21) Appl. No.: 13/875,969

(22) Filed: May 2, 2013

(65) Prior Publication Data
US 2013/0316363 A1   Nov. 28, 2013

Related U.S. Application Data

(60) Provisional application No. 61/641,812, filed on May 2, 2012, provisional application No. 61/784,807, filed on Mar. 14, 2013.

(51) Int. Cl.
| | |
|---|---|
| *B01L 3/00* | (2006.01) |
| *G01N 21/64* | (2006.01) |
| *G01N 33/569* | (2006.01) |
| *G01N 15/14* | (2006.01) |
| *B01L 9/00* | (2006.01) |
| *G01N 1/40* | (2006.01) |
| *G01N 15/10* | (2006.01) |

(52) U.S. Cl.
CPC .......... *G01N 21/6486* (2013.01); *B01L 3/502* (2013.01); *B01L 9/52* (2013.01); *G01N 15/1456* (2013.01); *G01N 21/6428* (2013.01); *G01N 33/569* (2013.01); *B01L 2200/025* (2013.01); *B01L 2300/069* (2013.01); *B01L 2300/0681* (2013.01); *B01L 2300/0803* (2013.01); *G01N 2001/4088* (2013.01); *G01N 2015/1006* (2013.01)

(58) Field of Classification Search
CPC ..... B01L 3/502; B01L 9/52; B01L 2300/0681
USPC ....................................... 435/308.1
See application file for complete search history.

(56) References Cited

U.S. PATENT DOCUMENTS

| | | |
|---|---|---|
| 4,725,891 A | 2/1988 | Manian |
| 4,739,416 A | 4/1988 | Manian |
| 4,838,632 A | 6/1989 | Manian |
| 4,930,893 A | 6/1990 | Manian |
| 5,137,609 A | 8/1992 | Manian et al. |
| 5,172,419 A | 12/1992 | Manian |
| 5,185,450 A | 2/1993 | Owen |
| 5,221,454 A | 6/1993 | Manian et al. |
| 5,296,341 A | 3/1994 | Manian |
| 5,314,805 A | 5/1994 | Haugland et al. |
| 5,436,134 A | 7/1995 | Haugland et al. |
| 5,437,980 A | 8/1995 | Haugland |
| 5,445,946 A | 8/1995 | Roth et al. |
| 5,534,416 A | 7/1996 | Millard et al. |
| 5,545,535 A | 8/1996 | Roth et al. |
| 5,547,849 A | 8/1996 | Baer et al. |
| 5,565,678 A | 10/1996 | Manian |
| 5,585,246 A | 12/1996 | Dubrow et al. |
| 5,603,900 A * | 2/1997 | Clark et al. ................... 422/535 |
| 5,658,751 A | 8/1997 | Yue et al. |
| 5,663,057 A | 9/1997 | Drocourt et al. |
| 5,843,680 A | 12/1998 | Manian et al. |
| 5,922,617 A | 7/1999 | Wang et al. |
| 5,932,428 A | 8/1999 | Dubrow et al. |
| 5,956,146 A | 9/1999 | Nakagawa |
| 6,130,745 A | 10/2000 | Manian et al. |
| 6,181,413 B1 | 1/2001 | Manian |
| 6,200,762 B1 | 3/2001 | Zlokarnik et al. |
| 6,203,996 B1 | 3/2001 | Duffy et al. |
| 6,214,563 B1 | 4/2001 | Negulescu et al. |
| 6,221,621 B1 | 4/2001 | Kinders et al. |

(Continued)

FOREIGN PATENT DOCUMENTS

| | | |
|---|---|---|
| CA | 1256360 A1 | 6/1989 |
| CA | 2002902 A1 | 5/1990 |

(Continued)

OTHER PUBLICATIONS

Sterlitech PETE (Polyester) Membranes (2013) pp. 1-2. downloaded from http://www.sterlitech.com/filters/membrane-disc-filters/polester-pete-membranes.html on Apr. 23, 2014.*

(Continued)

*Primary Examiner* — Sharmila G Landau
*Assistant Examiner* — Paul C Martin
(74) *Attorney, Agent, or Firm* — Goodwin Procter LLP

(57) ABSTRACT

The invention relates to a porous planar cell capture system for use in determining the presence and/or amount of cells, for example, viable cells, in a liquid sample, and to methods of using such a cell capture system. The cell capture system contains a fluid permeable, planar membrane adopted to retain cells thereon, a fluid permeable support member that supports the membrane, and an optional register associated with the membrane.

12 Claims, 43 Drawing Sheets

(56) References Cited

U.S. PATENT DOCUMENTS

| | | |
|---|---|---|
| 6,238,874 B1 | 5/2001 | Jarnagin et al. |
| 6,323,337 B1 | 11/2001 | Singer et al. |
| 6,420,183 B1 | 7/2002 | Krahn et al. |
| 6,441,894 B1 | 8/2002 | Manian et al. |
| 6,459,805 B1 | 10/2002 | Reynolds et al. |
| 6,737,238 B2 | 5/2004 | Suzuki et al. |
| 6,750,024 B2 | 6/2004 | Lee et al. |
| 6,750,457 B2 | 6/2004 | Heffelfinger et al. |
| 7,016,087 B2 | 3/2006 | Heffelfinger et al. |
| 7,018,804 B1 | 3/2006 | Zeigler |
| 7,063,952 B2 | 6/2006 | Krahn et al. |
| 7,067,324 B2 | 6/2006 | Knapp et al. |
| 7,118,878 B1 | 10/2006 | Hawkins et al. |
| 7,138,280 B2 | 11/2006 | Krahn et al. |
| 7,205,100 B2 | 4/2007 | Buttry et al. |
| 7,582,483 B2 | 9/2009 | Mizutani et al. |
| 7,615,376 B2 | 11/2009 | Krahn et al. |
| 7,785,536 B2 | 8/2010 | Knapp et al. |
| 8,021,848 B2 | 9/2011 | Straus |
| 8,093,015 B2 | 1/2012 | Obermann et al. |
| 8,148,515 B1 | 4/2012 | Mao et al. |
| 8,163,562 B2 | 4/2012 | Knapp et al. |
| 8,178,359 B2 | 5/2012 | Krahn et al. |
| 8,441,634 B2 | 5/2013 | Manian |
| 8,518,710 B2 | 8/2013 | Knapp et al. |
| 8,524,503 B2 | 9/2013 | Mao et al. |
| 2006/0040400 A1 | 2/2006 | Mizutani et al. |
| 2006/0121443 A1 | 6/2006 | Zeigler |
| 2006/0129327 A1 | 6/2006 | Kim et al. |
| 2008/0153125 A1 | 6/2008 | Buttry et al. |
| 2008/0305514 A1 | 12/2008 | Alford et al. |
| 2010/0105093 A1 | 4/2010 | Bugler et al. |
| 2011/0294206 A1 | 12/2011 | Tai et al. |
| 2012/0104280 A1 | 5/2012 | Manian |
| 2012/0107950 A1 | 5/2012 | Manian |
| 2012/0114536 A1 | 5/2012 | Manian et al. |
| 2013/0315802 A1 | 11/2013 | Manian et al. |

FOREIGN PATENT DOCUMENTS

| | | |
|---|---|---|
| CA | 1311685 C | 12/1992 |
| CA | 2190516 A1 | 12/1995 |
| CA | 2236687 A1 | 5/1997 |
| CA | 2289566 A1 | 12/1998 |
| CA | 2427106 A1 | 5/2001 |
| CA | 2405769 A1 | 10/2001 |
| CA | 2428074 A1 | 5/2002 |
| CA | 2445509 A1 | 12/2002 |
| CA | 2549014 A1 | 7/2005 |
| CA | 2559393 A1 | 9/2005 |
| CA | 2598937 A1 | 8/2006 |
| CA | 2623597 A1 | 3/2007 |
| CA | 2705100 A1 | 5/2009 |
| CA | 2724173 A1 | 11/2009 |
| CA | 2768699 A1 | 1/2011 |
| EP | 0563858 A1 | 10/1993 |
| EP | 0612850 A2 | 8/1994 |
| EP | 0713087 A1 | 5/1996 |
| EP | 0881489 A1 | 12/1998 |
| EP | 1219950 A1 | 7/2002 |
| EP | 1219951 A1 | 7/2002 |
| EP | 1624071 A2 | 2/2006 |
| EP | 2024727 A1 | 2/2009 |
| EP | 1688740 | 8/2009 |
| JP | 7229828 | 8/1995 |
| JP | 7280741 | 10/1995 |
| JP | 8145620 | 6/1996 |
| JP | 2001-228088 A | 8/2001 |
| JP | 2001-242082 A | 9/2001 |
| JP | 2002-323437 A | 11/2002 |
| WO | WO-1986/05206 A1 | 9/1986 |
| WO | WO-1992/02632 A1 | 2/1992 |
| WO | WO-1995/00660 A1 | 1/1995 |
| WO | WO-1997/12226 A1 | 4/1997 |
| WO | WO-1999/09455 A1 | 2/1999 |
| WO | WO-1999/35499 A1 | 7/1999 |
| WO | WO-2000/50872 A2 | 8/2000 |
| WO | WO-2003/022999 A2 | 3/2003 |
| WO | WO-2007/131596 A1 | 11/2007 |
| WO | WO-2008/042003 A2 | 4/2008 |
| WO | WO-2008/127677 A2 | 10/2008 |
| WO | WO-2009/029039 A1 | 3/2009 |
| WO | WO-2009/082218 A1 | 7/2009 |
| WO | WO-2010/006615 A2 | 1/2010 |
| WO | WO-2010/129521 A1 | 11/2010 |
| WO | WO-2010/151131 A2 | 12/2010 |
| WO | WO-2011/118764 A1 | 9/2011 |
| WO | WO-2011/124927 A1 | 10/2011 |
| WO | WO-2011/151793 A1 | 12/2011 |
| WO | WO-2012/051437 A1 | 4/2012 |
| WO | WO-2012/059784 A1 | 5/2012 |
| WO | WO-2012/059785 A1 | 5/2012 |
| WO | WO-2012/059786 A1 | 5/2012 |
| WO | WO-2013/166336 A1 | 11/2013 |
| WO | WO-2013/166337 A1 | 11/2013 |
| WO | WO-2013/166338 A2 | 11/2013 |

OTHER PUBLICATIONS

Anonymous, Invitrogen Bacteria Counting (2007), pp. 1-4, downloaded from http://tools.lifetechnologies.com/content/sfs/manuals/mp07277.pdf on Jun. 12, 2014.

Berney et al. Assessment and Interpretation of Bacterial Viability by Using the Live/Dead Baclight Kit in Combination With Flow Cytometry; Applied and Environmental Microbiology, vol. 73, No. 10 (2007) pp. 3283-3290.

Giao et al. Validation of SYT09/Propidim Iodide Uptake for Rapid Detection of Viable but Noncultivable Legionella Pneumophila; Microbial Ecology, vol. 58 (2009) pp. 56-62.

"Bacterial Detection and Live/Dead Discrimination by Flow Cytometry," BD Biosciences, 2002,www.bdbiosciences.com, 6 pages.

"CyQUANT Cell Proliferation Assay Kit (C-7026)—Prodcut Information," Revised—Jan. 12, 2001 (5 pages).

"CyQUANT Direct Cell Proliferation Assay Kit," Retrieved from the Internet: URL:http://tools.invitrogen.comjcontent/sfsjmanualsjmp35011.pdf, Jul. 20, 2009 (8 pages).

de Grooth, B.G. et al. (1985) "The Cytodisk: Cytometer Based Upon a New Principle of Cell Alignment," Cytometry, 6:226-233.

Deligeorgiev, T. et al. (2009) "Intercalating Cyanine Dyes for Nucleic Acid Detection," Recent Patents on Material Science, 2: 1-26.

Diaz, A. (1990) "Absorption and Emission Spectroscopy and Photochemistry of 1,10-Anthraquinone Derivatives: A Review," Journal of Photochemistry and Photobiology A: Chemistry, 53: 141-167.

Doose, S. et al. (2005) "A Close Look at Fluorescence Quenching of Organic Dyes by Tryptophan," ChemPhysChem, 6: 2277-2285.

Fujimoto, B. et al. (1994) "Fluorescence and Photobleaching Studies of Methylene Blue Binding to DNA," J. Phys. Chem., 98(26): 6633-6643.

Hassan, S. M., et al. (2010) "Hemolytic and Antimicrobial Activities Differ Among Saponin-rich Extracts From Guar, Quillaja, Yucca, and Soybean," Appl. Biochem. Biotechnol., 162: 1008-1017.

International Search Report and Written Opinion for PCT/US2013/039347, dated Aug. 9, 2013 (9 pages).

International Search Report and Written Opinion for PCT/US2013/039349, dated Aug. 9, 2013 (8 pages).

International Search Report for PCT/US2013/039350, dated Nov. 26, 2013 (4 pages).

Jepras, R. I. et al. (1995) "Development of a Robust Flow Cytometric Assay for Determining Numbers of Viable Bacteria," Appl. Environ. Microbiol., 61: 2696-2701.

Kelley, S. et al. (2000) "Luminescence quenching by DNA-bound viologens: effect of reactant identity on efficiency and dynamics of electron transfer in DNA," Journal of Photochemistry and Photobiology B: Biology, 58: 72-79.

Koley, D. et al. (2010) "Triton X-100 concentration effects on membrane permeability of a single HeLa cell by scanning electrochemical microscopy (SECM)," PNAS, 107(39): 16783-16787.

(56) References Cited

OTHER PUBLICATIONS

Kossanyi, J. et al. (2000) "Electron transfer reaction and demetalation of phthalocyanines," International Journal of Photoenergy, 2:9-15.

Li, H. et al. (2005) "A live-cell high-throughput screening assay for identification of fatty acid uptake inhibitors," Analytical Biochemistry, 336(1): 11-19.

Lipscomb. L. et al. (1996) "Structure of a DNA-Porphyrin Complex," Biochemistry, 35(9): 2818-2823.

López-Amorós, R. et al. (1997) "Assessment of *E. coli* and *Salmonella* Viability and Starvation by confocal Laser Microscopy and Flow Cytometry Using Rhodamine 123, DiBAC4(3), Propidium Iodide , and CTC," Cytometry, 29: 298-305.

Marmé, N. et al. (2003) "Inter- and Intramolecular Fluorescence Quenching of Organic Dyes by Tryptophan," Bioconjugate Chem., 14(6): 1133-1139.

Nafisi, S. et al. (2006) "Stability and structural features of DNA intercalation with ethidium bromide, acridine orange and methylene blue," Journal of Molecular Structure, 827(1-3): 35-43.

Njoh, K. et al. (2006) "Spectral Analysis of the DNA Targeting Bisalkylaminoanthraquinone DRAQ5 in Intact Living Cells," Cytometry Part A, 69A: 805-814.

Prentø, P. et al. (2003) "Methyl green-pyronin Y staining of Nuvleic acids: studies on the effects of staining time, dye composition and diffusion rates," Biotechnic & Histochemistry, 78(1): 27-33.

Richer, H. et al. (1988) "Effect of ascorbate on oxygen uptake and growth of *Escherichia coli* B," Can. J. Microbiol., 34: 822-824.

Roth, P. (2008) "Synthesis and Evaluation of Guanidino Phthalocyanines for G-quadruplex Binding," Diplom Thesis, Institute of Organic Chemistry, University of Zurich, 80 pages.

ScanRDI®—Real-Time Microbiology Results; Product Insert; AES Chemunex, 2008 (8 pages).

Scott, J. E. (1972) "Histochemistry of Alcian Blue. III. The Molecular Biological Basis of Staining by Alcian Blue 8GX and Analogous Phthalocyanins," Histochemie, 32: 191-212.

Shapiro, H. (1981) "Flow Cytometric Estimation of DNA and RNA Content in Intact Cells Stained with Hoechst 33342 and Pyronin Y," Cytometry, 2(3): 143-150.

Shapiro, H. et al. (1986) "Flow Cytometry of DNA Content Using Oxazine 750 or Related Laser Dyes With 633 nm Excitation," Cytometry, 7: 107-110.

Singh, R. et al. (2003) "Bridged Tetraquaternary Salts from N,N'-Polyfluoroalkyl-4,4'-bipyridine," Inorg. Chem., 42(23): 7416-7421.

Smith, R. et al. (2010) "Evaluation of the ScanRDI as a Rapid Alternative to the Pharmacopoeial Sterility Test Method: Comparison of the Limits of Detection," PDA J. Pharm. Sci. And Tech., 64(4): 356-363.

Snehalatha, M. et al. (2008) "Azure A chloride: computational and spectroscopic study," J. Raman Spectrosc., 40: 176-182.

Song, G. et al. (2005) "Oxazine 170 Induices DNA:RNA:DNA Triplex Formation," J. Med. Chem., 48(10): 3471-3473.

Tarin, J. et al. (1998) "Dithiothreitol prevents age-associated decrease in oocyte/conceptus viability in vitro," Human Reproduction, 13(2): 381-386.

Vaiana, A. et al. (2003) "Fluorescence Quenching of Dyes by Tryptophan: Interactions at Atomic Detail from Combination of Experiment and Computer Simulation," J. Am. Chem. Soc., 125(47): 14564-14572.

Vogelsang, J. et al. (2009) "Controlling the fluorescence of ordinary oxazine dyes for single-molecule switching and superresolution microscopy," PNAS, 106(20): 8107-8112.

Yip, D. et al. (1972) "The Dye-Exclusion Test for Cell Viability: Persistence of Differential Staining Following Fixation," In Vitro, 7(5): 323-329.

Zhao, X. et al. (2004) "A rapid bioassay for single bacterial call quantitation using bioconjugated nanoparticles," PNAS, 101(42): 15027-15032.

AES Chemunex, ABRASP Meeting (Oct. 20, 2011), downloaded from http://www.abrasp.org.br/downloads/2011/aes.pdf on Apr. 9, 2014, 56 pages.

Millipore Isopore Membrane Filters, downloaded from https://millipore.com/catalogue/module/c153 on Apr. 9, 2014, 2 pages.

* cited by examiner

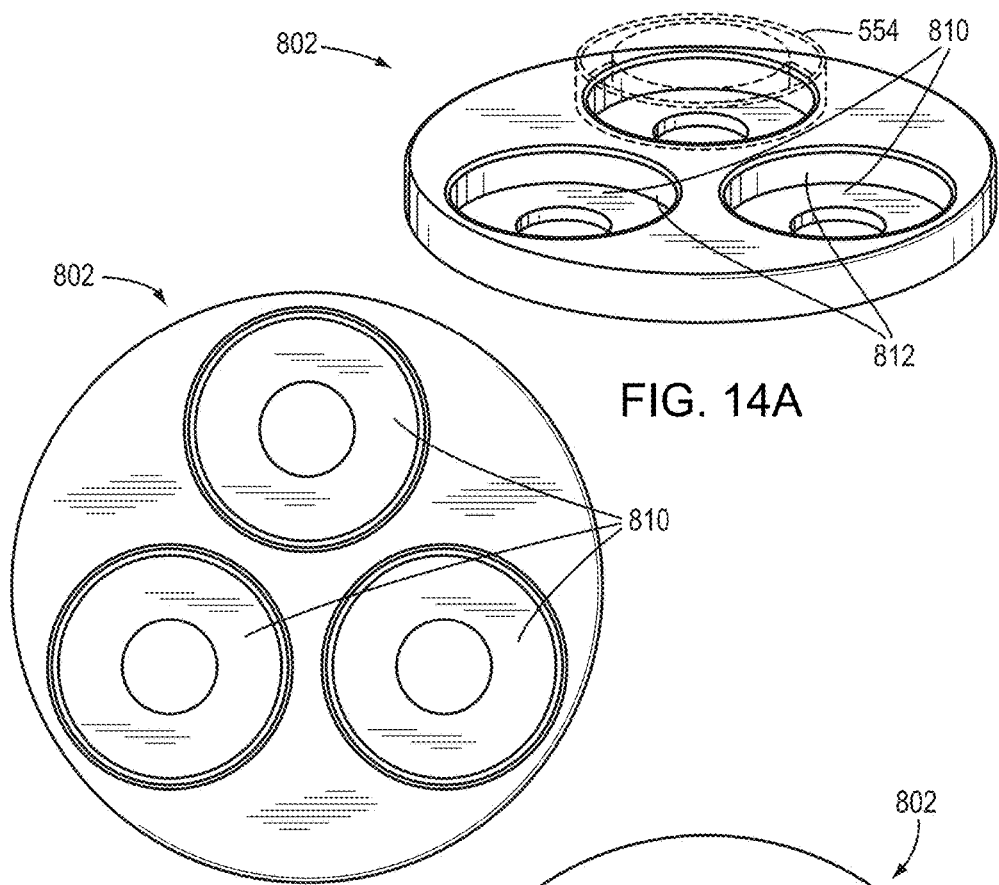
FIG. 14A
FIG. 14B
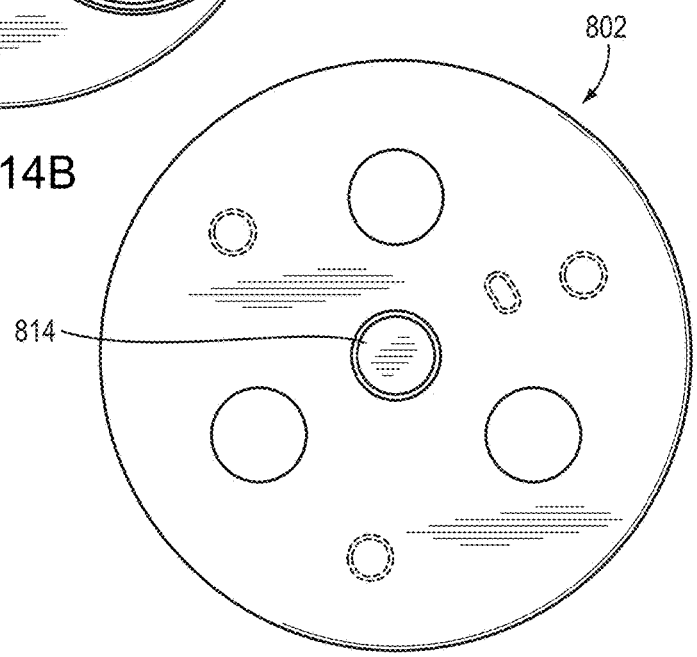
FIG. 14C

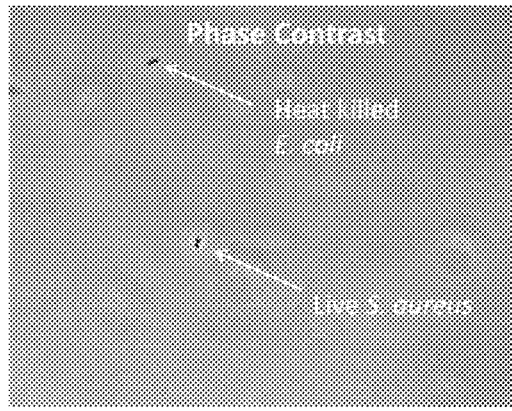 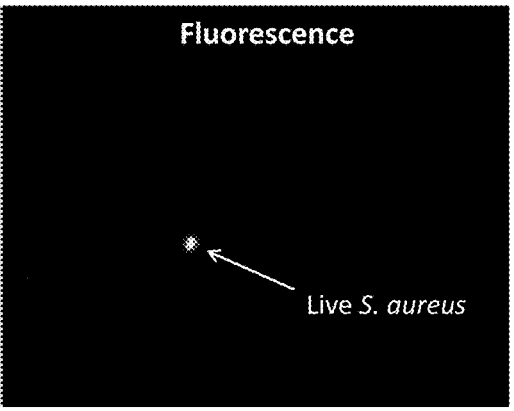
FIG. 24A   FIG. 24B
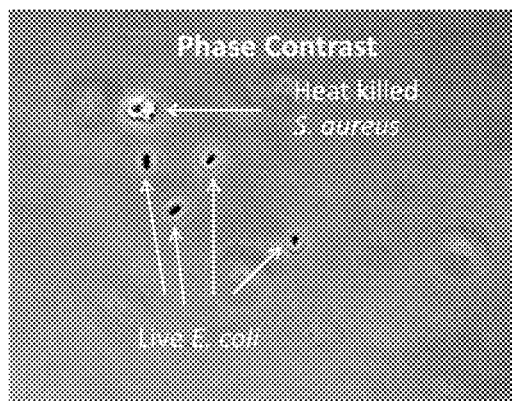 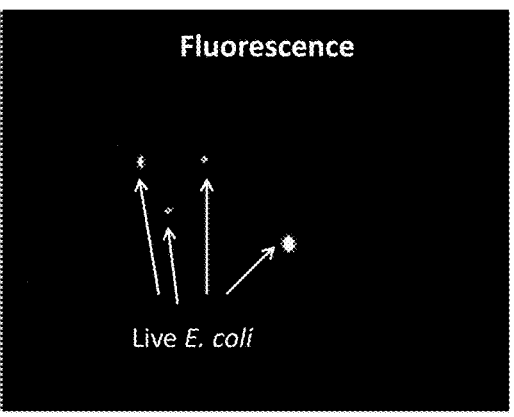
FIG. 24C   FIG. 24D

POROUS PLANAR CELL CAPTURE SYSTEM

CROSS-REFERENCE TO RELATED APPLICATIONS

This application claims priority to and the benefit of U.S. Provisional Patent Application No. 61/641,812, filed May 2, 2012, and U.S. Provisional Patent Application No. 61/784,807, filed on Mar. 14, 2013; the entire contents of each application are incorporated herein by reference.

FIELD OF THE INVENTION

This invention relates generally to cell capture system for use in determining the presence and/or amount of cells, for example, viable cells, in a liquid sample, and to methods of using such a cell capture system.

BACKGROUND

Microbial contamination by, for example, Gram positive bacteria, Gram negative bacteria, and fungi, for example, yeasts and molds, may cause severe illness and, in some cases, even death in human and animal subjects. Manufacturers in certain industries, for example, food, water, cosmetic, pharmaceutical, and medical device industries, must meet exacting standards to verify that their products do not contain levels of microbial contaminants that would otherwise compromise the health of a consumer or recipient. These industries require frequent, accurate, and sensitive testing for the presence of microbial contaminants to meet certain standards, for example, standards imposed by the United States Food and Drug Administration or Environmental Protection Agency.

Depending upon the situation, the ability to distinguish between viable and non-viable cells can also be important. For example, during the manufacture of pharmaceuticals and biologics, it is important that the water used in the manufacturing process is sterile and free of contaminants. Furthermore, it is important that water contained in medicines (for example, liquid pharmaceutical and biological dosage forms, for example, injectable dosage forms) and liquids (for example, saline) that are administered to a subject, for example, via non-parenteral routes, is also sterile and free of contaminants. On the other hand, the presence of some viable microorganisms in drinking water may be acceptable up to a point. In order to be potable, drinking water must meet exacting standards. Even though microorganisms may be present in the water supply the water may still be acceptable for human consumption. However, once the cell count exceeds a threshold level, the water may no longer be considered safe for human consumption. Furthermore, the presence of certain predetermined levels of microorganisms in certain food products (for example, fresh produce) and drinks (for example, milk) may be acceptable. However, once those levels have been exceeded the food or drink may be considered to have spoiled and no longer be safe of human consumption.

Traditional cell culture methods for assessing the presence of microbial contamination and/or the extent of microbial contamination can take several days to perform, which can depend upon the organisms that are being tested for. During this period, the products in question (for example, the food, drink, or medical products) may be quarantined until the results are available and the product can be released. As a result, there is a need for systems and methods for rapidly detecting (for example, within hours or less) the presence and/or amount of microbial contaminants, in particular, viable microbial contaminants, in a sample.

SUMMARY

The invention is based, in part, upon the discovery of a cell capture system that can be used to determine the presence of viable cells in a cell containing sample. The cell capture system can be used in combination with an optical detection system that detects the presence of viable cells in the sample. The results can be used to measure the bioburden (for example, to measure the number and/or percentage and/or fraction of viable cells) of a particular sample of interest.

In one aspect, the invention provides a cell capture system. The system comprises a fluid permeable, planar membrane comprising an exposed first surface, at least a portion of which is adapted to retain cells thereon. The portion (i) defines a plurality of pores having an average diameter less than about 1 µm so as to permit fluid to traverse the portion of the membrane while retaining cells thereon, (ii) is substantially non-autofluorescent when exposed to light having a wavelength in a range from about 350 nm to about 1000 nm, and (iii) has a flatness tolerance of up to about 100 µm. The cell capture system optionally further comprises a register (for example, line, spot, or other feature) associated with the membrane so as to permit the determination of the location of cells retained on at least a portion of the planar membrane.

The membrane can be of any of a variety of shapes, for example, circular, annular, ovoid, square, rectangular, elliptical, etc., and can have some portion or all of one side exposed for cell retention. Moreover, the membrane may form one or more apertures therein to accommodate a mask and may be formed from several separate membranes assembled together with the mask or other structural element. In one embodiment, the membrane may be in the shape of a disc, for example, a substantially planar disc. The membrane (for example, in the form of a disc) can have a thickness in a range selected from the group consisting of from 1 µm to 3,000 µm, from 10 µm to 2,000 µm, and from 100 µm to 1,000 µm.

In certain embodiments, the cell capture system further comprises a fluid permeable support member adjacent at least a portion of a second surface of the membrane that is opposite the first surface of the membrane. The fluid permeable support, for example, in the form of a rigid porous plastic frit, retains enough fluid to maintain moisture in the porous membrane disposed adjacent the permeable support, which in certain embodiments, can help maintain the viability of cells retained on the porous membrane. The support member can have a thickness in a range selected from the group consisting of from 0.1 mm to 10 mm, from 0.5 mm to 5 mm, and from 1 mm to 3 mm.

In certain embodiments, the cell capture system further comprises a mask proximate at least another portion of the first surface of the membrane. Depending upon the design configuration (for example, when the porous membrane is a disk), the mask can be circular.

In certain embodiments, the cell capture system further comprises a plurality of detectable particles, for example, fluorescent particles. The fluorescent particles can be adapted to be excited by a beam of light having a wavelength at least in a range from about 350 nm to about 1000 nm, or a wavelength in a range from about 350 nm to about 600 nm or a wavelength in a range from about 600 nm to about 750 nm. The particles can be used as part of a positive control to ensure that one or more of the cell capture system, the cell capture method, the detection system, and the method of detecting the viable cells are operating correctly.

Depending upon the design of the cell capture system, the particles (for example, fluorescent particles) can be pre-disposed upon at least a portion of the porous membrane or disposed within a well formed in a mask. Alternatively, the particles (for example, fluorescent particles) can be mixed with the liquid sample prior to passing the sample through the porous membrane. In such an approach, the fluorescent particles can be dried in a vessel that the sample of interest is added to. Thereafter, the particles can be resuspended and/or dispersed within the liquid sample. Alternatively, the fluorescent particles can be present in a second solution that is mixed with the liquid sample of interest. Thereafter, the particles can be dispersed within the liquid sample.

In certain embodiments, the cell capture system, in particular the porous membrane, has a sterility assurance level less than $10^{-6}$, $10^{-7}$, $10^{-8}$, or $10^{-9}$. This can be achieved, for example, by sterilizing the cell capture system, via techniques known in the art, for example, autoclaving, exposure to ionizing radiation, for example, gamma radiation, or exposure to a sterilizing fluid or gas, for example, ethylene oxide. The cell capture system can be enclosed within a receptacle, for example, a bag, prior to, during, or after sterilization. It is contemplated that the cell capture system can be placed within a receptacle, for example, within a bag that is sealed, for example, hermetically sealed, before terminal sterilization, for example, via exposure to ionizing radiation.

In another embodiment, the invention provides a cell capture cup comprising an open cylindrical portion and an annular seal adapted to mate and engage with a base comprising the cell capture system of any one of the foregoing aspects and embodiments. The cell capture cup and the base can have a sterility assurance level less than $10^{-6}$, $10^{-7}$, $10^{-8}$, or $10^{-9}$, which can be achieved using any of the approaches discussed hereinabove.

In another aspect, the invention provides a method of determining the presence and/or amount of cells in a liquid sample. The method comprises the steps of: (a) capturing cells present in the sample on the any one of the cell capture system and/or the cell capture cup disclosed herein; and (b) determining the presence or amount of cells captured in step (a). The method can further comprise the step of labeling the captured cells with a detectable moiety, for example, a fluorescent label. The determining step can utilize an optical detector, for example, a fluorescence detector.

In another aspect, the invention provides a method of detecting presence of viable cells, and/or measuring the viability of cells, in a liquid sample. The method comprises the steps of: (a) capturing cells present in the sample and/or the cell capture cup disclosed herein; (b) selectively labeling captured viable cells; and (c) detecting the presence of cells labeled in step (b) and/or measuring the viability of cells labeled in step (b). The cells can be labeled using at least one of a viability stain and a viability staining system, each of which can comprise a fluorescent moiety. The labeled viable cells can be detected with an optical detector, for example, a fluorescence detector.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIGS. 14A-14C are schematic perspective, top, and bottom views, respectively, of an exemplary stage;

FIGS. 24A-E are phase contrast and fluorescence images of mixed populations of viable and non-viable microorganisms stained with exemplary pairs of nucleic acid binding fluorescent dyes and a nucleic acid binding fluorescence quenchers, where the cells were imaged using an epifluorescent microscope (FIGS. 24A-D, where phase contrast images are shown in FIGS. 24A and C, and the corresponding fluorescence images are shown in FIGS. 24B and D, respectively) or using a detection system shown in FIG. 1A.

DESCRIPTION

Figure 1A:
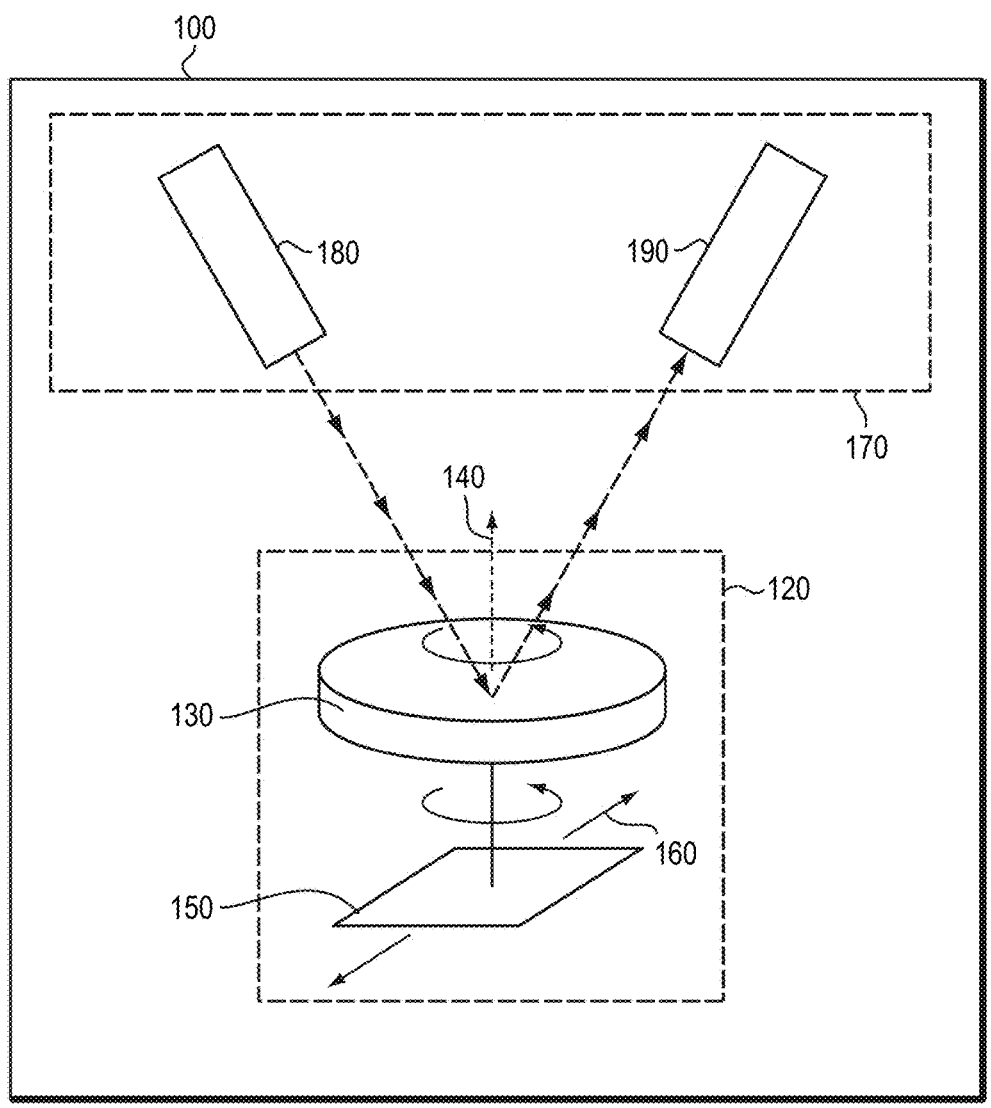
FIG. 1A is a schematic representation of an exemplary detection system that can be used to determine the presence and/or amount of viable cells in a cell sample.

The instant invention is directed to a cell capture system, a method of capturing cells (including viable cells) in the cell capture system, a method for selectively staining viable cells, (e.g., viable cells captured in the cell capture system), and to a method for determining the presence and/or amount of viable cells in a cell sample (e.g., a liquid sample). The cell capture system and the various methods can be used, either alone or in combination, to determine the presence and/or amount of viable cells in a cell containing sample and, in particular, can be used to determine the bioburden (e.g., to measure the number and/or percentage and/or fraction of viable cells in a sample) of a particular sample of interest. The cell capture system and the various methods can be used to measure the bioburden of cells in a liquid sample (e.g., a water sample), a comestible fluid (e.g., wine, beer, milk, baby formula or the like), a body fluid (e.g., blood, lymph, urine, cerebrospinal fluid or the like), growth media, a liquid sample produced by harvesting cells from a source of interest (e.g., via a swab) and then dispersing and/or suspending the harvested cells, if any, in a liquid (e.g., buffer or growth media).

It is contemplated that, by using the devices and methods described herein, it will be possible to determine the presence and/or amount of viable cells in sample within less than approximately 2 hours, less than approximately 1 hour, or even less than approximately 30 minutes after the cells have been captured on a porous membrane of the cell capture system. It is contemplated, however, depending upon the desired sensitivity, it is possible to culture the cells captured on the porous membrane (e.g., for 15 minutes to several hours) to permit cell proliferation. Nevertheless, by using the devices and methods described herein, even when including a culturing step, it is possible to determine the presence and/or amount of viable cells in a sample much faster than other technologies available in the art.

Each of the various aspects and certain embodiments of the invention will be discussed in detail below.

(I) Cell Capture System

The cell capture system described herein can be used with an optical detection system that detects the presence of viable cells. The results can be used to measure the bioburden (e.g., to measure the number and/or percentage and/or fraction of viable cells in a sample) of a particular sample of interest. Exemplary detection systems are described, for example, in International Patent Application No. PCT/IB2010/054965, filed Nov. 3, 2010, U.S. patent application Ser. No. 13/034,402, filed Feb. 24, 2011, International Patent Application No. PCT/IB2010/054966, filed Nov. 3, 2010, U.S. patent application Ser. No. 13/034,380, filed Feb. 24, 2011, International Patent Application No. PCT/IB2010/054967, filed Nov. 3, 2010, and U.S. patent application Ser. No. 13/034,515, filed Feb. 24, 2011. One embodiment of an exemplary system 100, as shown schematically in FIG. 1A, comprises a sample assembly 120 comprising (i) a rotating platform 130 upon which a porous membrane having cells disposed thereon rotates about a rotation axis 140, and (ii) a movable platform 150 that translates linearly (see track 160) relative to a detection system 170 that comprises a light source 180 (e.g., a white light source or a laser light source (e.g., a near infrared laser)), and at least one detector 190, for example, a fluorescence detector. A beam of light from light source 180 (excitation light) impinges rotating platform 130 and the planar membrane disposed thereon, while emission light is detected by detector 190. The light source 180 and the detector 190 may be arranged at similar angles relative to the platform 130 as the beam of light will impact and leave the platform 130 at substantially the same angle. In certain circumstances, the detection system consists of a single detector that detects a single wavelength range (see FIG. 12B) or multiple wavelength ranges. Alternatively, the detection system consists of multiple detectors, each of which is capable of detecting a different wavelength range.

Figure 1B:
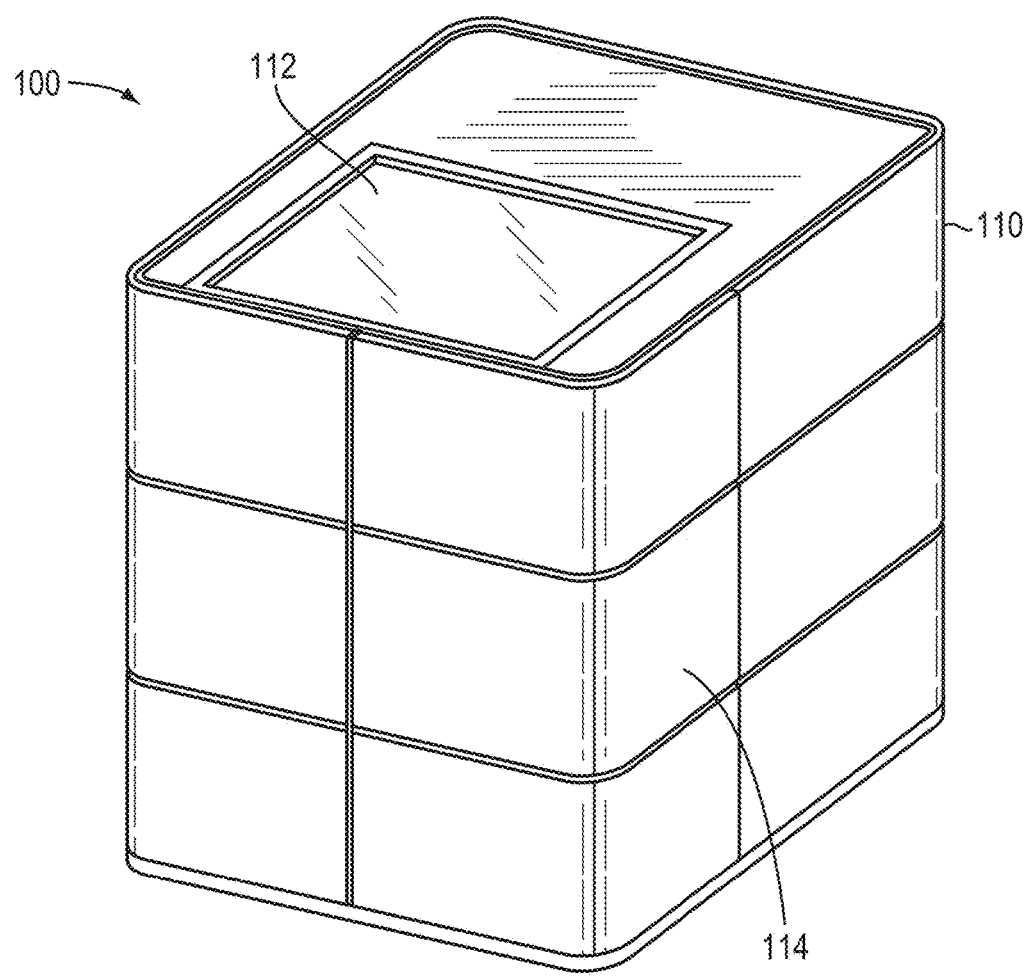
FIG. 1B is a schematic perspective view of an exemplary detection system with a door in a closed position.
Figure 1C:
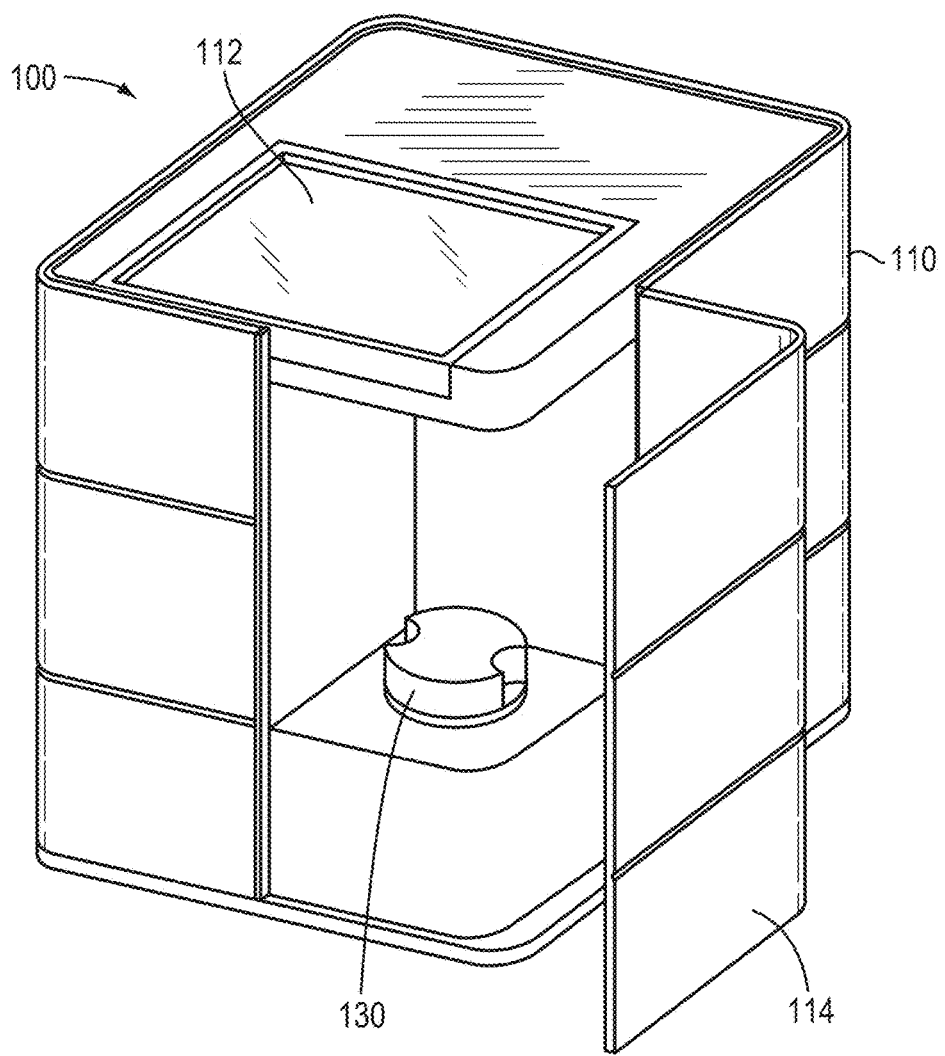
FIG. 1C is a schematic perspective view of the exemplary detection system of FIG. 1B with the door in an open position.
Figure 1D:
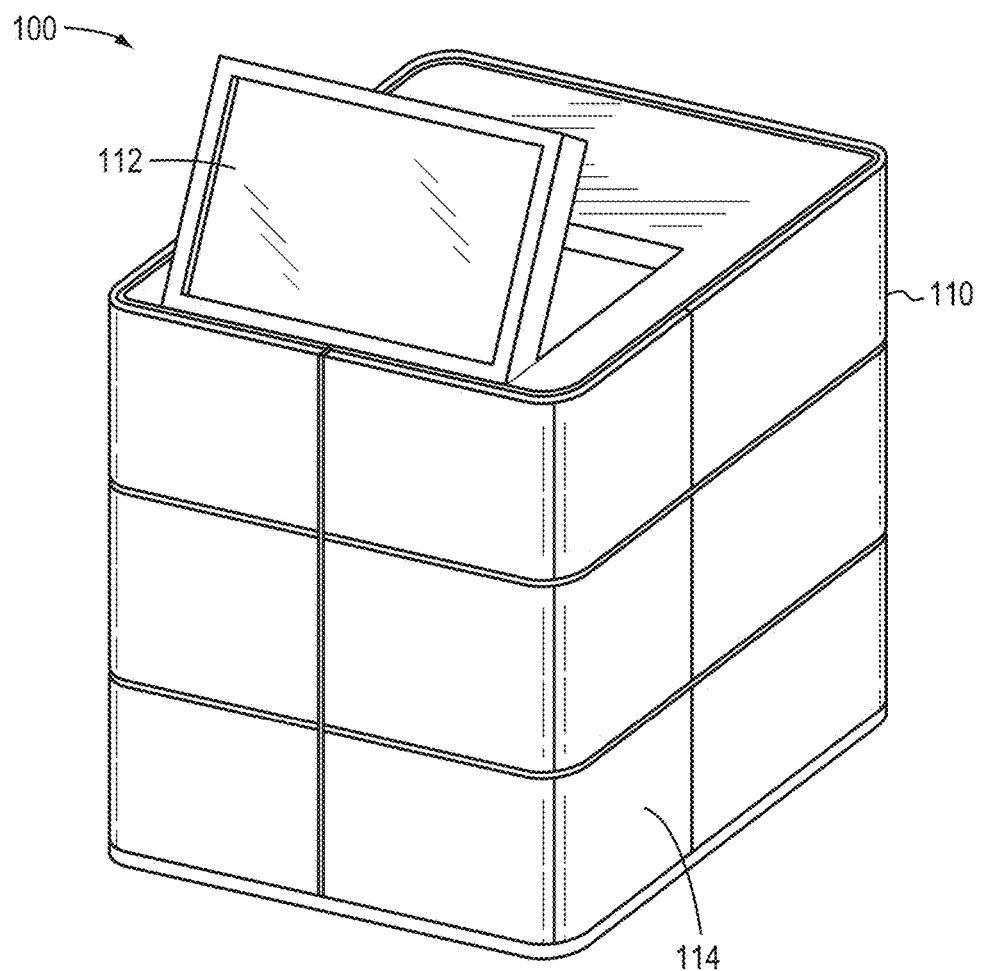
FIG. 1D is a schematic perspective view of the exemplary detection system of FIG. 1B with a touchscreen in a raised position.

FIGS. 1B-1D depict the exemplary cell detector system 100 having an enclosure 110 and a display (e.g., a touchscreen) 112. The enclosure 110 is sized to house the rotating platform 130, which may be accessed through a door 114 on the enclosure 110. The enclosure 110 may be manufactured in various shapes and sizes, including in the depicted rectangular prism form that is approximately 10 in.×10 in.×12 in. (l×w×h). Other shapes may be a cube, cylinder, sphere, or other prism, amongst others. While dimensions vary depending on the shape, the enclosure 110 may range in scale from a few inches to several feet, and possibly lesser or greater, depending on the application. FIG. 1B depicts a cell detection system with the door 114 in a closed configuration and FIG. 1C depicts the same system with door 114 in an open configuration to show rotating platform 130. The touchscreen 112 provides a user interface for controlling the operation of the system 100, and may display information regarding the system's 100 current operating parameters. The touchscreen 112 may be adjustable into a more upright position (as depicted in FIG. 1D) in order to facilitate easier operation. In certain embodiments, the touchscreen 112 is only active when in the upright position. In other embodiments, the touchscreen 112 is always active, or only at select times (e.g., when engaged by a user).

It is understood that such detection systems operate optimally when the cells are disposed upon a solid support or otherwise maintained in a planar orientation with a tight flatness tolerance (e.g., within a flatness tolerance of up to about 100 µm (±50 µm), e.g., up to about 10 µm (±5 µm), up to about 20 µm (±10 µm), up to about 30 µm (±15 µm), up to about 40 µm (±20 µm), up to about 50 µm (±25 µm), up to about 60 µm (±30 µm), up to about 70 µm (±35 µm), up to about 80 µm (±40 µm), up to about 90 µm (±45 µm)), so that the cells can be visualized readily by a detection system within a narrow focal plane. If a dynamic focusing system is employed, it is contemplated that flatness tolerances greater than 100 µm can be tolerated. Accordingly, it can be preferable to use a support system that maintains the membrane and any captured cells in a substantially planar orientation and within a suitably tight flatness tolerance to permit reliable detection. Depending on the detection system and requirements post detection, the support system may be adapted to present and/or maintain planarity of the membrane when dry and/or when wet or moist after cells have been captured on the solid support after passing a cell containing solution through the solid support via pores disposed within the solid support.

The invention provides a cell capture system comprising a fluid permeable, planar membrane comprising an exposed first surface, at least a portion of which is adapted to retain cells thereon. The portion can: (i) define a plurality of pores having an average diameter less than about 1 µm so as to permit fluid to traverse the portion of the membrane while retaining cells thereon; (ii) be substantially non auto-fluorescent when exposed to light having a wavelength in a range from about 350 nm to about 1000 nm; and (iii) have a flatness tolerance of up to about 100 µm. The cell capture system 100 optionally further comprises a register (e.g., line, spot, or other mark, indicia or structural feature) associated with the membrane so as to permit the determination of the location of cells (for example, the viable cells) retained on at least a portion of the planar membrane. For a disc shaped membrane, polar coordinates (i.e., radial "r" and angular "θ" coordinate locations) may be suitable.

The membrane can be of any of a variety of shapes, e.g., circular, annular, ovoid, square, rectangular, elliptical, etc., and can have some portion or all of one side exposed for cell retention. Moreover, the membrane may form one or more apertures therein to accommodate a mask and may be formed from several separate membranes assembled together with the mask or other structural element. In one embodiment, the membrane may be in the shape of a disc, e.g., a substantially planar disc. In certain embodiments, the portion of the porous membrane for capturing cells and/or particles is greater than 400 mm$^2$, 500 mm$^2$, 600 mm$^2$, 700 mm$^2$, 800 mm$^2$, 900 mm$^2$ or 1,000 mm$^2$. The membrane (e.g., in the form of a disc) can have a thickness in a range selected from the group consisting of approximately from 1 µm to 3,000 µm, from 10 µm to 2,000 µm, and from 100 µm to 1,000 µm.

In certain embodiments, the cell capture system 100 further comprises a fluid permeable support member adjacent at least a portion of a second opposing surface of the membrane. The fluid permeable support, for example, in the form of a smooth planar porous plastic frit, retains enough fluid to maintain moisture in the porous membrane disposed adjacent the permeable support, which in certain embodiments, can be important to maintain the viability of cells retained on the porous membrane. The support member can have a thickness in a range selected from the group consisting of approximately from 0.1 mm to 10 mm, from 0.5 mm to 5 mm, and from 1 mm to 3 mm.

In certain embodiments, the cell capture system 100 further comprises a mask proximate at least another portion of the first surface of the membrane. Depending upon the design configuration (e.g., when the porous membrane is a disk), the mask can be circular or annular, optionally with radial spokes or supports.

The porous membrane defines a plurality of pores having an average diameter less than about 1 µm so as to permit fluid to traverse the membrane while retaining cells thereon. In certain embodiments, the average pore diameter is about or less than about 0.9 µm, 0.8 µm, 0.7 µm, 0.6 µm, 0.5 µm, 0.4 µm, 0.3 µm, 0.2 µm, 0.1 µm, or 0.05 µm. In certain embodiments, the average pore diameter is about 0.2 µm, and in other embodiments the average pore diameter is about 0.4 µm. Suitable membranes can be fabricated from nylon, nitrocellulose, polycarbonate, polyacrylic acid, poly(methyl methacrylate) (PMMA), polyester, polysulfone, polytetrafluoroethylene (PTFE), polyethylene and aluminum oxide.

In addition, the porous membrane is substantially non-autofluorescent when exposed to light having a wavelength in the range from about 350 nm to about 1,000 nm. As used herein with reference to the porous membrane, the term "substantially non-autofluorescent when exposed to a beam of light having a wavelength in the range from about 350 nm to about 1,000 nm" is understood to mean that the porous membrane emits less fluorescence than a fluorescently labeled cell or a fluorescent particle disposed thereon when illuminated with a beam of light having a wavelength, fluence and irradiance sufficient to cause a fluorescence emission from the cell or particle. It is understood that a user and/or detector should be able to readily and reliably distinguish a fluorescent event resulting from a fluorescent particle or a fluorescently labeled cell from background fluorescence emanating from the porous membrane. The porous membrane is chosen so that it is possible to detect or visualize a fluorescent particle or a fluorescently labeled cell disposed on such a porous membrane. In certain embodiments, the fluorescence emitted from a region of a porous membrane (e.g., a region having approximately the same surface area as a cell or cell colony or particle being visualized) illuminated with a beam of light may be no greater than approximately 30% (e.g., less than 30%, less than 27.5%, less than 25%, less than 22.5%, less than 20%, less than 17.5%, less than 15%, less than 12.5%, less than 10%, less than 7.5%, less than 5%, or less than 2.5%) of the fluorescence emitted from a fluorescent particle or a fluorescently labeled cell, when measured under the same conditions, for example, using a beam of light with the same wavelength, fluence and/or irradiance.

Suitable membranes that are non-autofluorescent can be fabricated from a membrane, e.g., a nylon, nitrocellulose, polycarbonate, polyacrylic acid, poly(methyl methacrylate) (PMMA), polyester, polysulfone, polytetrafluoroethylene (PTFE), or polyethylene membrane impregnated with carbon black or sputtered with an inert metal such as but not limited to gold, tin or titanium. Membranes that have the appropriate pore size which are substantially non-autofluorescent include, for example, ISOPORE™ membranes (Merck Millipore), NUCLEOPORE™ Track-Etched membranes (Whatman), ipBLACK Track Etched Membranes (distributed by AR Brown, Pittsburgh, Pa.), and Polycarbonate (PCTE) membrane (Sterlitech).

In order to facilitate accurate detection and count estimation of the captured cells, it is beneficial (even essential in some instances, depending on the configuration and capabilities of the detection system) that the membrane is substantially planar (e.g., substantially wrinkle free) during cell detection. As used herein, the term "substantially planar" is understood to mean that an article has a flatness tolerance of less than approximately 100 μm. This is because height imperfections (e.g., wrinkles) may interfere with the optical detection/measurement system, leading to erroneous results. As a result, it can be important for the porous membrane when dry and/or wet and depending on detection conditions), retains a relatively tight flatness tolerance, within the detection capability of the detection system. Various approaches described below allow the porous membrane to be held substantially flat after cells from a sample fluid are captured thereon and other approaches may be apparent to those skilled in the art based on the discussion herein.

In certain embodiments, the cell capture system further comprises a plurality of detectable particles, for example, fluorescent particles. The fluorescent particles can be adapted to be excited by a beam of light having a wavelength at least in a range from about 350 nm to about 1000 nm, a wavelength in a range from about 350 nm to about 600 nm a wavelength in a range from about 600 nm to about 750 nm, or any of the wavelength ranges discussed above. The particles can be used as part of a positive control to ensure that one or more of the cell capture system, the cell capture method, the detection system, and the method of detecting the viable cells are operating correctly.

Depending upon the design of the cell capture system, the particles (for example, fluorescent particles) can be pre-disposed upon at least a portion of the porous membrane or disposed within a well formed in a mask. Alternatively, the particles (for example, fluorescent particles) can be mixed with the liquid sample prior to passing the sample through the porous membrane. In such an approach, the fluorescent particles can be dried in a vessel that the sample of interest is added to. Thereafter, the particles can be resuspended and/or dispersed within the liquid sample. Alternatively, the fluorescent particles can be present in a second solution that is mixed with the liquid sample of interest. Thereafter, the particles can be dispersed within the liquid sample.

Figure 2A:
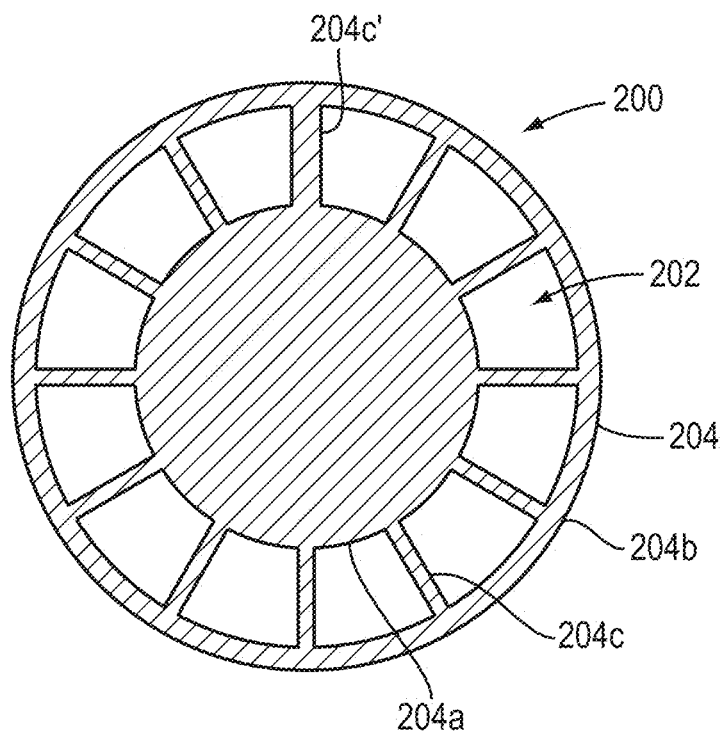
FIG. 2A is a schematic top view of an exemplary membrane assembly.

FIG. 2A shows an exemplary membrane assembly 200 comprising a porous planar membrane 202 and a frame (or mask) 204 to hold porous membrane 202 substantially flat, i.e., without allowing the formation of significant wrinkles therein. As shown, frame 204 comprises a central portion 204a connected to a circumferential portion or outer rim 204b via a plurality of spokes (e.g., tensioning spokes) 204c. One of the spokes denoted 204c' may be thicker than the other spokes 204c and represents a register from which the co-ordinates of cells disposed on the membrane can be measured (for example, r, θ values), where r is the radial distance measured from the axis of rotation and θ is the included angle between (i) a radial line traversing the point of rotation and the cell and (ii) the register 204c'.

Membrane 202 comprises a plurality of pores having an average diameter about or less than about 1 μm, for example, about or less than about 0.9 μm, 0.8 μm, 0.7 μm, 0.6 μm, 0.5 μm, 0.4 μm, 0.3 μm, 0.2 μm, 0.1 μm, or 0.05 μm. As such, when a liquid fluid containing cells and/or particles contacts membrane 202, the fluid can traverse through the membrane via the pores, while the cells and/or particles are retained on a surface of the membrane 202. The membrane 202 is substantially non auto-fluorescent when exposed to light having a wavelength in the range from about 350 nm to about 1000 nm. Moreover, the membrane 202 has a smooth surface having a flatness tolerance no greater than about 100 μm when restrained or configured for detection by the associated detection system.

Figure 2B:
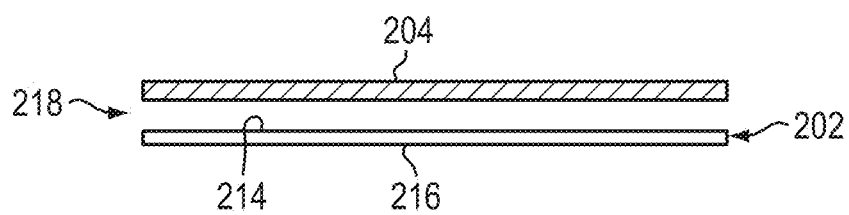
FIG. 2B is a schematic, exploded side view of the membrane assembly of FIG. 2A.

As shown in FIG. 2B, membrane 202 has a first surface 214 and a second surface 216 that is opposite the first surface. First surface 214 may be affixed to the frame 204, e.g., via an adhesive bonding layer 218. The central portion 204a can be affixed to a central portion of membrane 202. In the embodiment shown, the diameter of the membrane 202 is about the same as that of the outer rim 204b, and as a result, the outer rim 204b is affixed to the perimeter of the membrane 202. The spokes 204c extend radially from the central portion 204a and may be affixed to the membrane 202. This configuration can hold the membrane 202 substantially flat, preventing or minimizing the formation of wrinkles. Furthermore, the formation of wrinkles can also be mitigated or eliminated by applying downward pressure on the central portion 204a, which increases the surface tension in membrane 202.

Figure 3A:
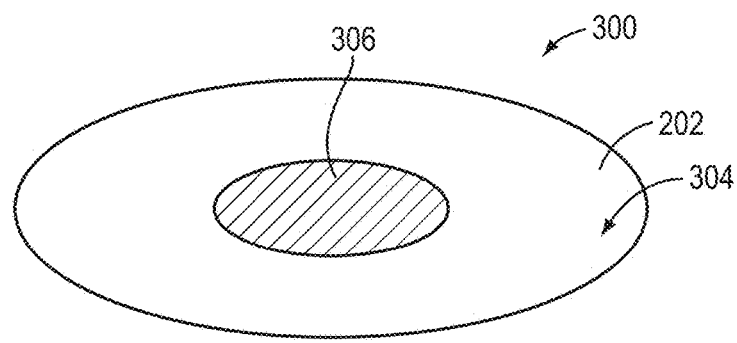
FIGS. 3A and 3B are schematic representations of exemplary membrane assemblies.

In another approach, as depicted in FIG. 3A, a circular membrane assembly 300 comprises a porous membrane 202 having an upper surface 304. A circular mask 306, affixed to a central portion of the surface 304, holds the membrane 202 substantially flat. In the membrane assembly 300, cells in the fluid sample, if any are present therein, are captured on the exposed portion of the surface 304 that is not covered by the mask 306. Membrane assembly 300 may be disposed on a fluid permeable porous support member, as described below, that may maintain the desired flatness of the membrane during detection. Alternatively or additionally, in order to keep the membrane 202 substantially flat, downward pressure may be applied to the mask 306. Materials suitable for the mask 306 include plastic, polycarbonate, polystyrene, polypropylene, and other materials having water repellant properties.

Figure 3B:
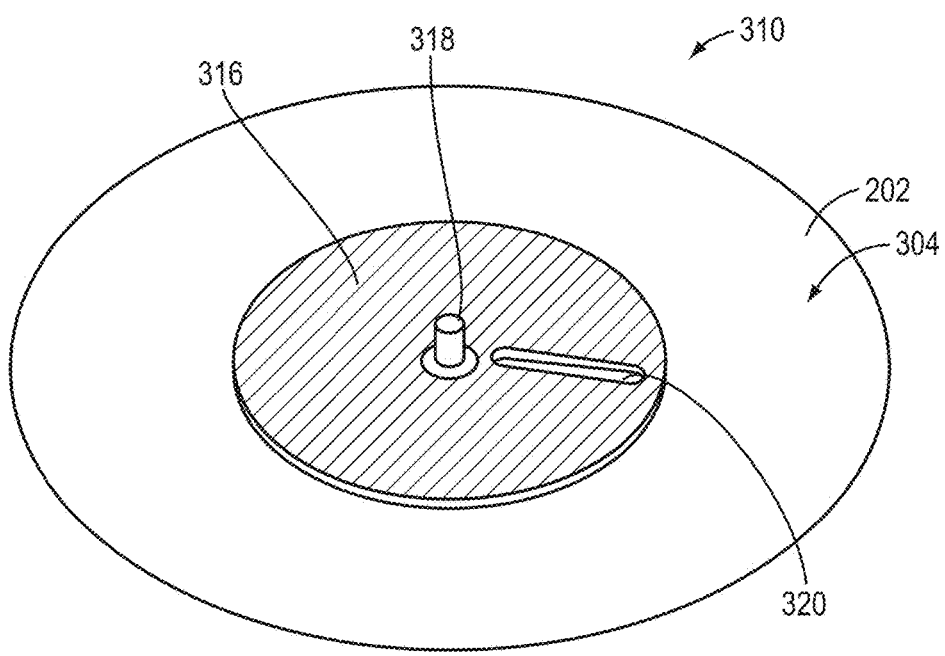

FIG. 3B depicts a membrane assembly 310 that is similar to the membrane assembly 300 shown in FIG. 3A. A mask 316 is similar to the mask 306, but the mask 316 has a protrusion or nipple 318 that allows a user to pick up the assembly 310 (including the membrane 202) with fingers or forceps, and transfer the assembly 310 to another location, e.g., on a membrane holder. The top surface of the mask 316 also defines a well 320 that may serve as a register so that the location of a particle or cell detected on the surface 304 of the membrane 202 can be described with reference to the location of the well 320. Alternatively or in addition, control particles to be detected may be initially disposed in the well 320. In certain other embodiments, the mask may include either the protrusion or the well, but not both.

Figure 4A:
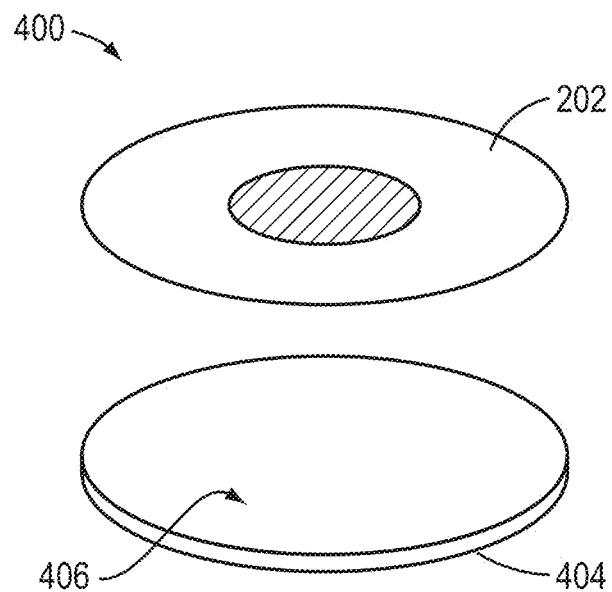
FIG. 4A is a schematic, exploded perspective view of an exemplary membrane assembly having a permeable membrane and a fluid permeable support member.
Figure 4B:
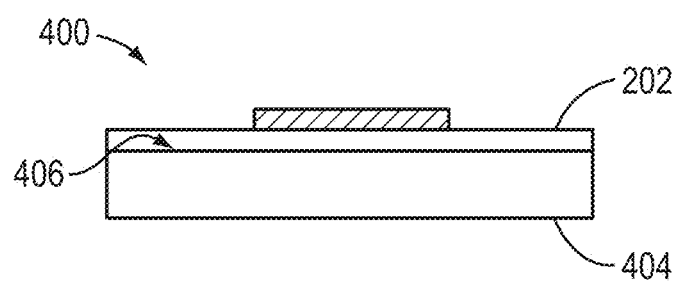
FIG. 4B is a schematic side view of the exemplary permeable membrane assembly of FIG. 4A.

In another approach, as depicted in FIGS. 4A and 4B, the porous membrane 202 may be disposed in a membrane assembly 400 to maintain the porous membrane 202 in a substantially planar configuration without the need for the frame 204 or the masks 306 or 316, by placing the porous membrane 202 upon a fluid permeable, solid support member 404. In one embodiment, when the porous membrane 202 is wetted, surface tension between the membrane 202 and the solid support member 404 conforms the bottom surface of the membrane 202 to an upper mating surface 406 of the support member 404. For example, in one embodiment, the support member 404 may be a fluid permeable, solid substantially planar element that keeps membrane 202 in a substantially planar configuration, for example, when the membrane is wetted. The support member 404 is porous, and the upper mating surface 406 is substantially flat and smooth. In another embodiment, the solid support member 404 is coated with a non-toxic adhesive, for example, polyisobutylene, polybutenes, butyl rubber, styrene block copolymers, silicone rubbers, acrylic copolymers, or some combination thereof. When a downward pressure is applied, for example, from a vacuum, the porous membrane 202 becomes loosely adhered to the solid support member 404, which results in the porous membrane conforming to the surface 406 of the solid support member 404. The support member 404 is porous, and the upper mating surface 406 is substantially flat and smooth. For example, in one embodiment, the surface 406 has a flatness tolerance of up to about 100 µm. The diameter of the support member 404 is approximately the same as that of the membrane 202, and preferably the support member 404 has a substantially uniform thickness. The support member can have a thickness in a range selected from the group consisting of approximately from 0.1 mm to 10 mm, from 0.5 mm to 5 mm, and from 1 mm to 3 mm. Materials suitable for making the porous support member 404 include plastic, polycarbonate, high density polyethylene (HDPE), glass, and metal. In one embodiment, the support member 404 is fabricated by sintering plastic particles made from poly (methyl methacrylate) having a mean diameter of 0.15-0.2 mm held at a temperature near the melting point of the particles and at a pressure sufficient to cause sintering of the particles to fuse them together and form a uniform structure.

Although the membrane 202 and the support member 404 are depicted as circular, this is illustrative only. In other embodiments, the membrane 202 and/or the support member 404 may be shaped as a square, a rectangle, an oval, etc. In general, the shape and the surface area of the support member, if it is used, is selected such that the surface of the support member is approximately the same size as or slightly smaller than the membrane disposed thereon.

The membrane 202 is disposed in contact with the substantially flat, smooth surface 406 of the support member 404 before the sample fluid is poured onto the membrane 202. The generally flat surface 406 helps keep the membrane 202 substantially flat after the sample fluid is drained. The fluid permeable solid support 404 can also serve as a reservoir for fluid passed through the membrane 202 and the fluid permeable solid support 404, to provide the additional benefit of preventing the membrane 202 and viable cells disposed thereon from drying out during the detection process. Drying can be detrimental to the viability of the cells retained on the membrane 202.

With reference to FIGS. 5A-5E, a cup and base assembly 500 having a cup 502 and a base 504 is used to facilitate the capture of cells present in a liquid sample on a membrane (e.g., the membrane 202) disposed within the base 504. The base 504 has a surface 506 (see, FIG. 5D), an outer wall 508, and a lip 510. The surface 506 defines at least one opening 512 and, optionally, circular and radial protrusions or grooves 514 to facilitate drainage of liquid passed through the membrane 202. The wall 508 has a circumferential groove 516 under the lip 510. In certain embodiments (see FIG. 5D), the cup 502 comprises a wall 520 having a circumferential protrusion 522 adapted to mate with the base groove 516 to releasably interlock the cup 502 to the base 504. A lip section 524 of the wall 520, i.e., the section below the protrusion 522, inclines inwardly to form a circumferential sealing lip adapted to contact an upper surface of the porous membrane 202. The lip section 524 also captures the porous membrane 202 (and in certain embodiments the frame 200 and/or the support member 404) between the cup 520 and the base 504.

Figure 5A:
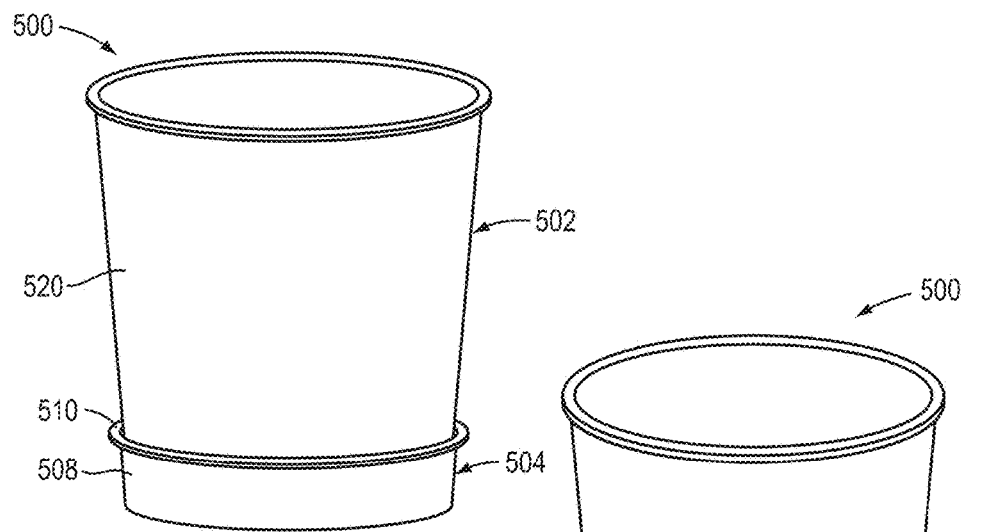
FIG. 5A is a schematic perspective view of an exemplary cell capture cup and a corresponding base.
Figure 5B:
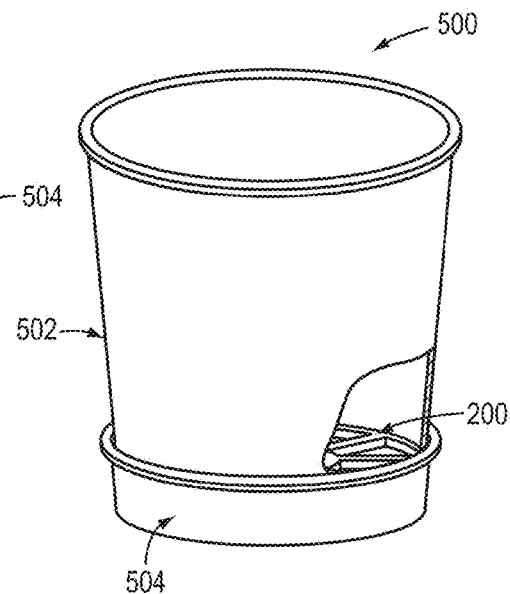
FIG. 5B is a schematic partial cut-away view of the cup and base of FIG. 5A showing a membrane assembly.
Figure 5C:
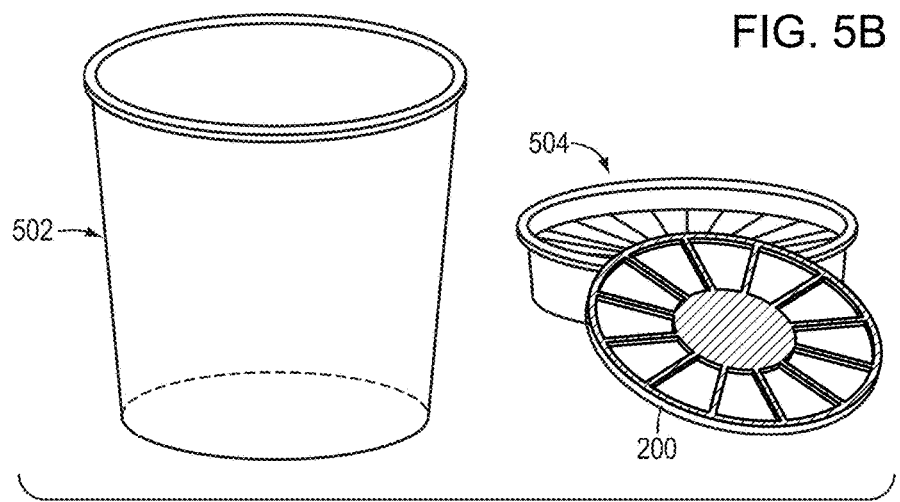
FIG. 5C is a schematic perspective view of the cup, base, and membrane assembly of FIG. 5B in an unassembled state.
Figure 5D:
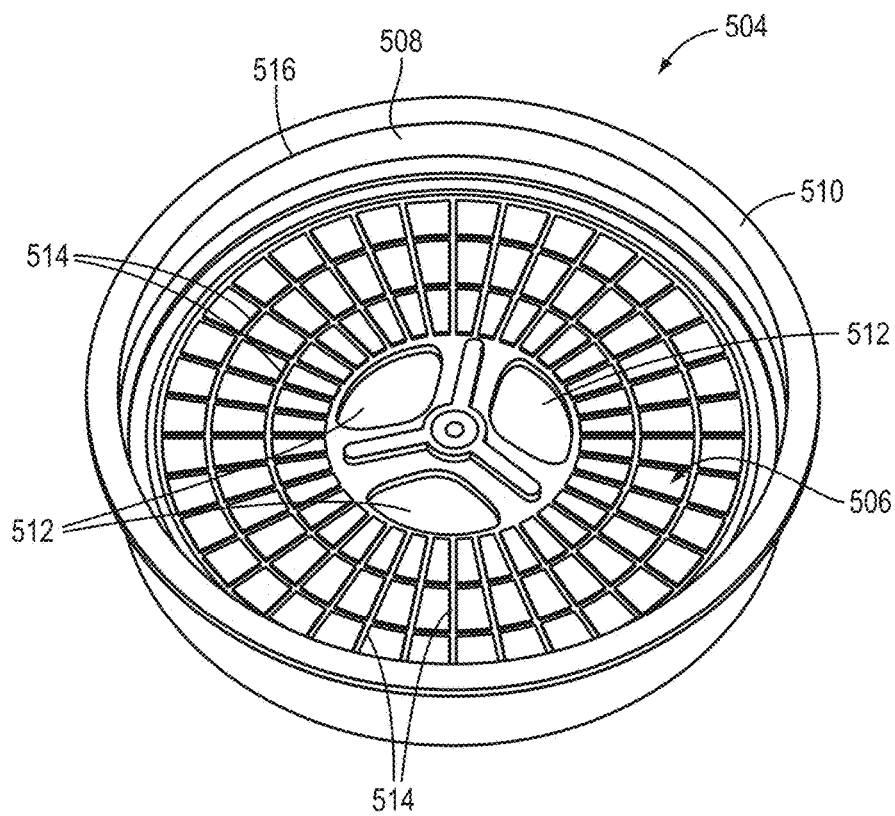
FIG. 5D is a schematic perspective view of the base of FIG. 5A.
Figure 5E:
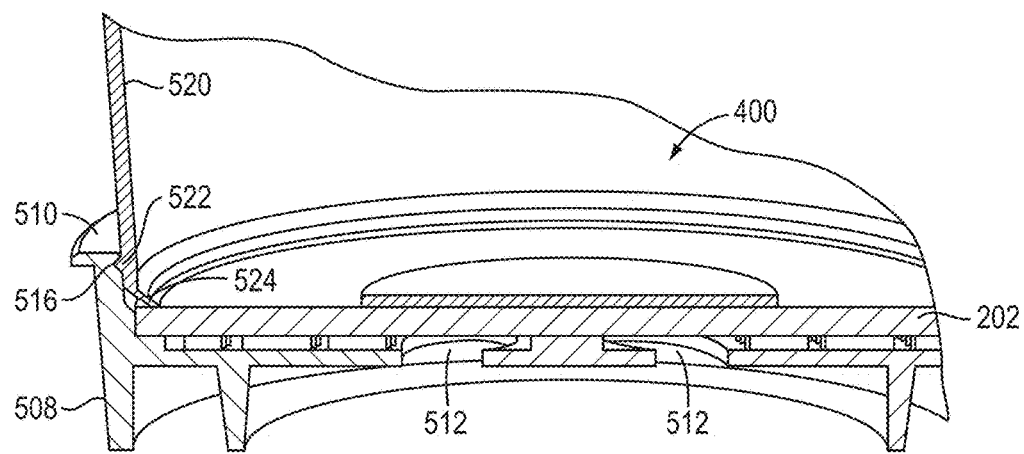
FIG. 5E is a schematic partial cross-sectional view of the cup and base of FIG. 5B with a different membrane holder assembly and posts from a separate holder.

More generally, a membrane and any components for holding the membrane generally flat, such as a holder having spokes (described with reference to FIGS. 2A and 2B), masks (described with reference to FIGS. 3A and 3B), and/or the supporting member (described with reference to FIGS. 4A and 4B) can be received within the cup and base assembly 500 and disposed on the surface 506 of the base 504. The cup 502 then is disposed over the membrane assembly such that the wall protrusion 522 fits into the groove 516 of the base 504, as depicted in FIG. 5E. This fit helps ensure the proper positioning between the cup 502 and the base 504, particularly with respect to the membrane 202 contained therebetween. The dimensions of the section 524 (e.g., the length, the angle of inclination, etc.) are selected such that the section 524 presses against the membrane assembly 400 disposed in the base 504 to provide a fluidic seal and ensure a flat membrane 202.

Figure 6A:
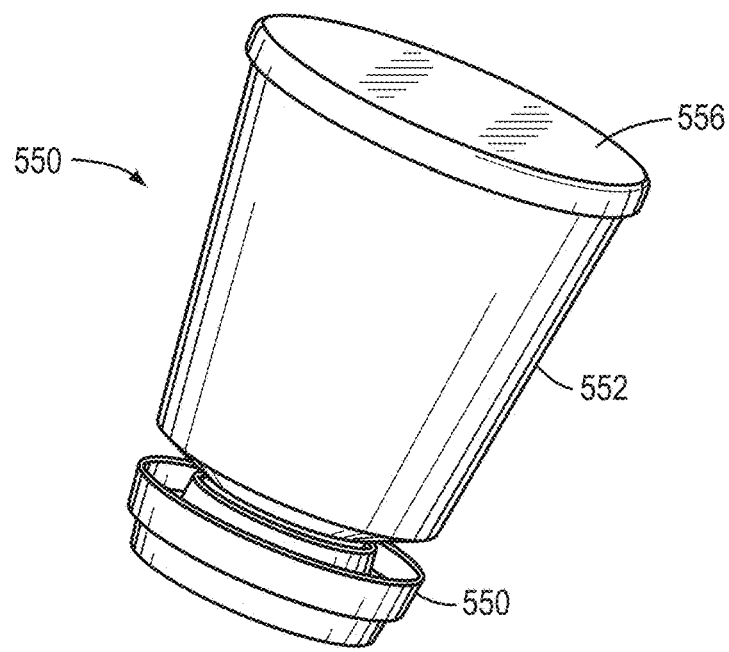
FIGS. 6A-6D are schematic perspective, side, top, and bottom views, respectively, of a cup assembly having a lid, a cup, a membrane, and a base.
Figure 6B:
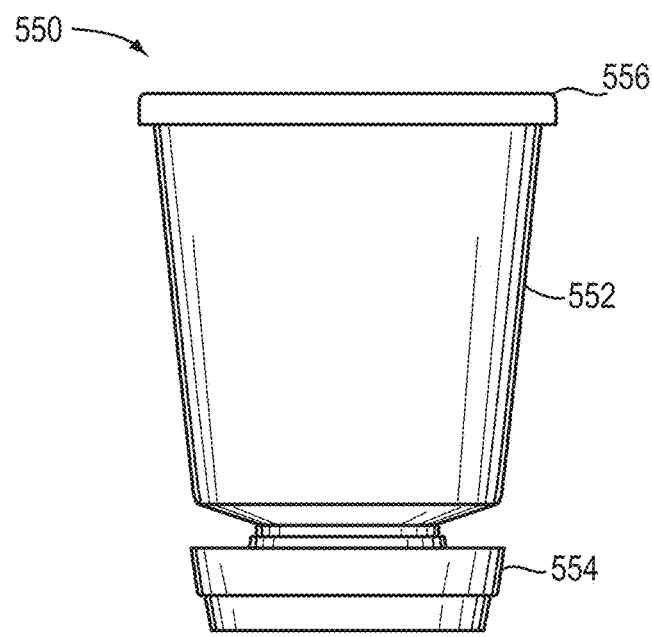
Figure 6C:
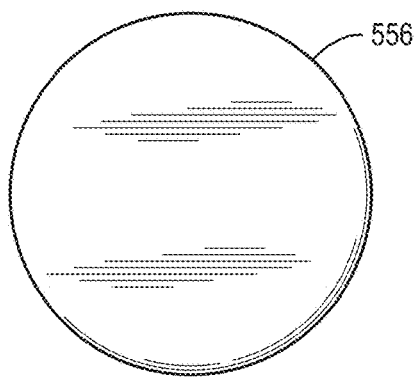
Figure 6D:
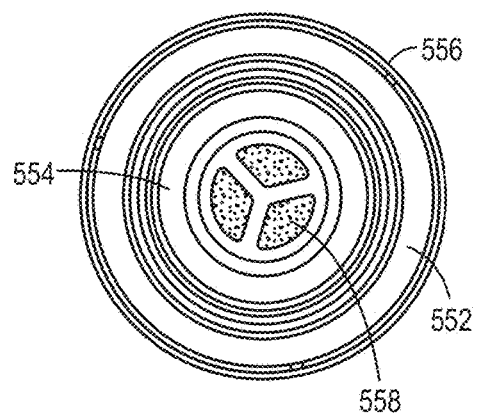
Figure 6E:
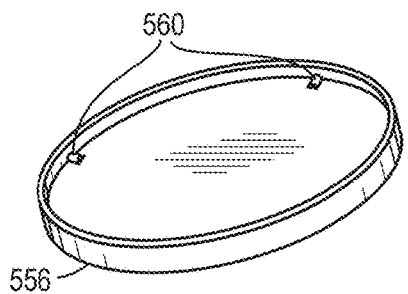
FIG. 6E is a schematic bottom perspective view of the lid of FIG. 6A.
Figure 6F:
FIG. 6F is a schematic side view of the lid of FIG. 6A.
Figure 7A:
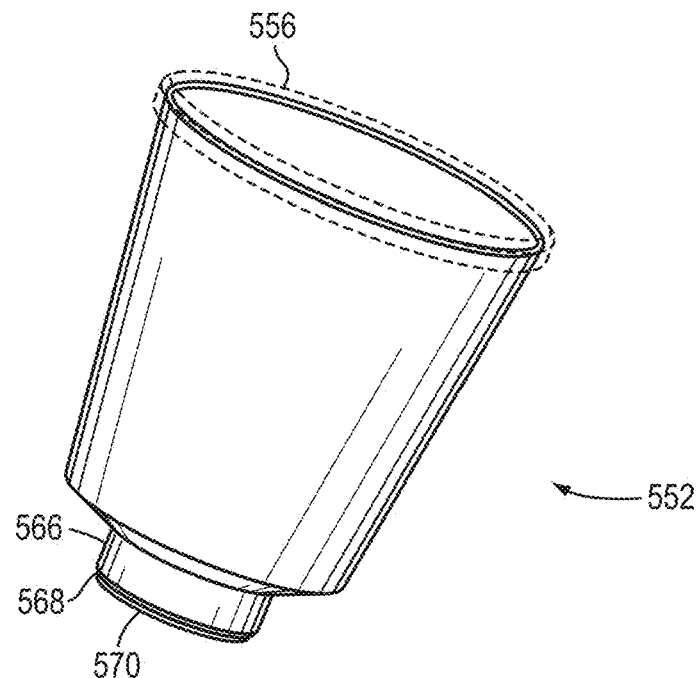
FIGS. 7A-7D are schematic perspective, side, top and bottom views, respectively, of a cup member shown in the cup assembly of FIG. 6A.
Figure 7B:
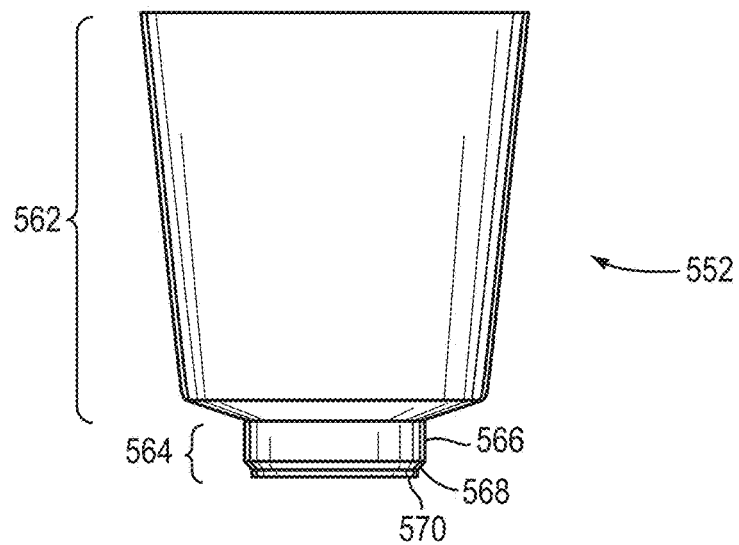
Figure 7C:
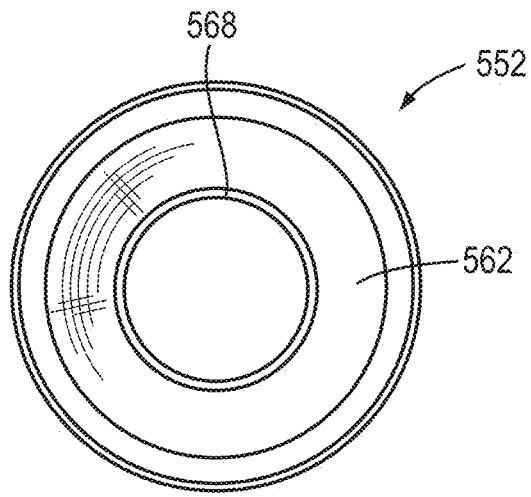
Figure 7D:
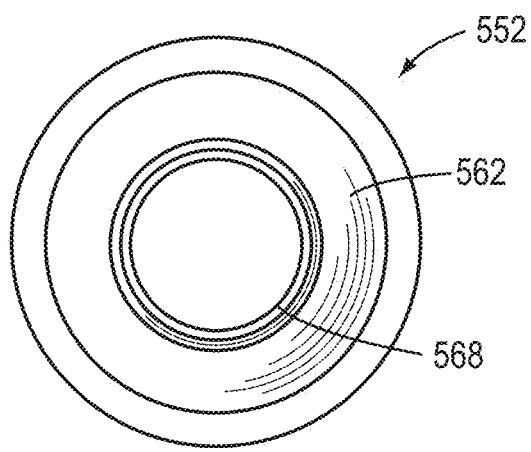
Figure 8A:
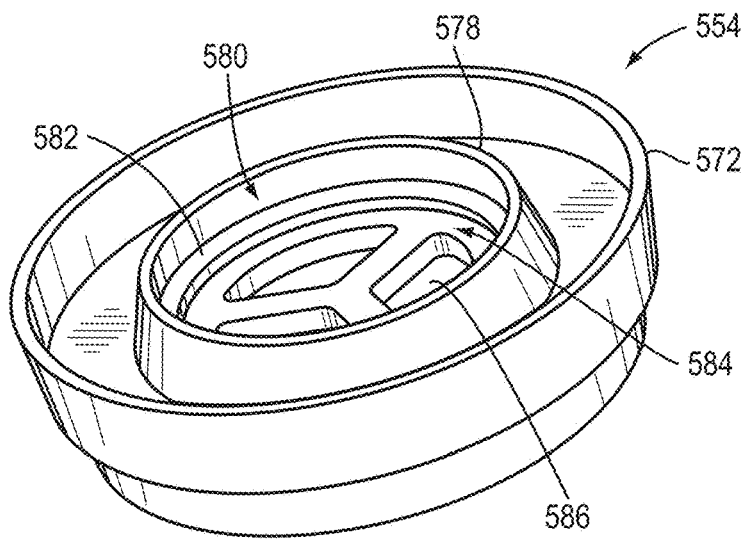
FIGS. 8A-8D are schematic perspective, top, bottom, and side views, respectively, of the base of the cup assembly of FIG. 6A.
Figure 8B:
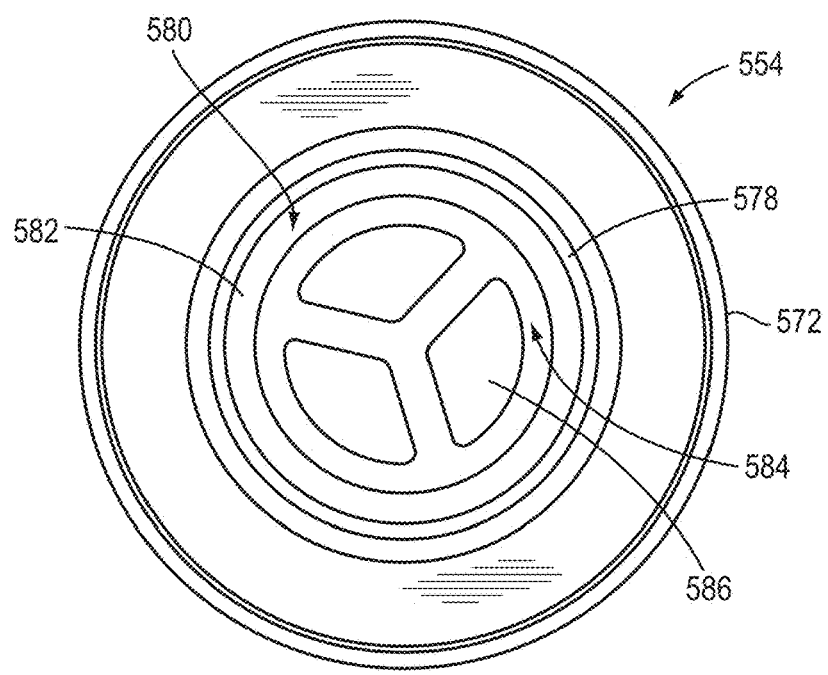
Figure 8C:
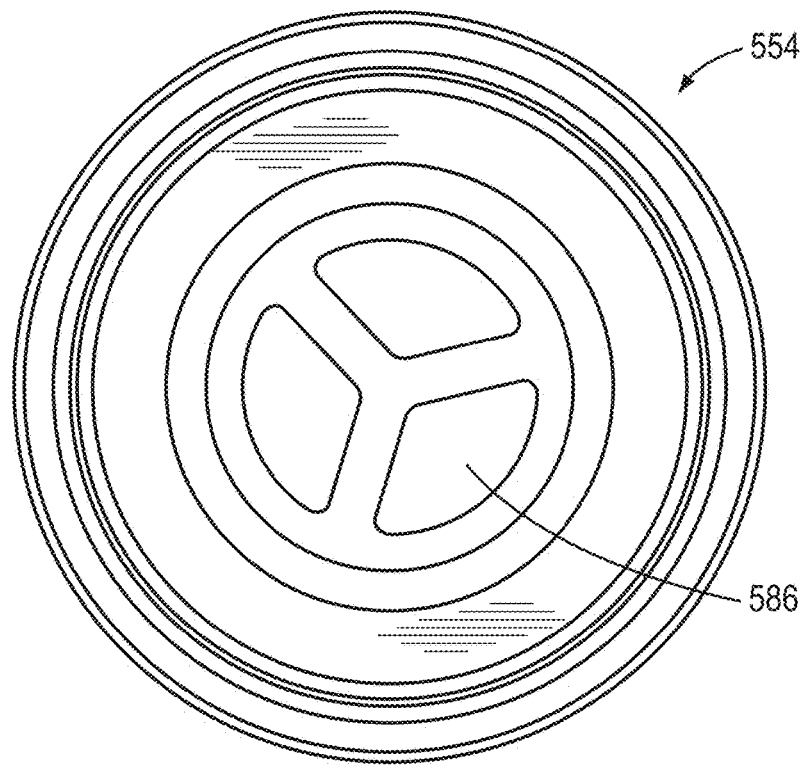
Figure 8D:
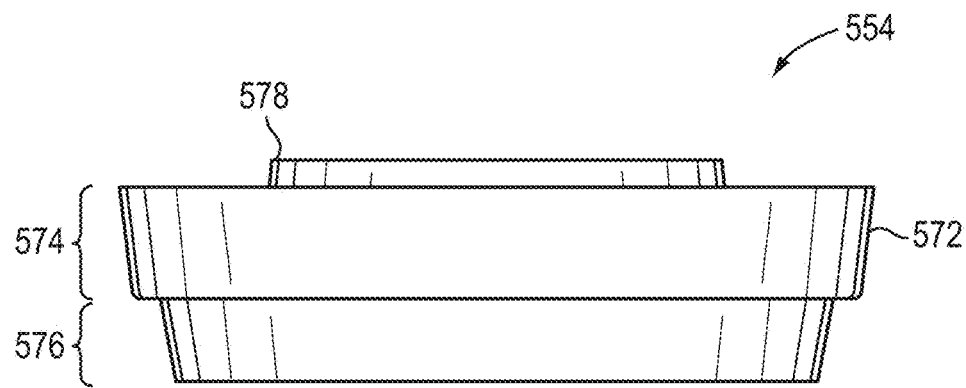
Figure 9A:
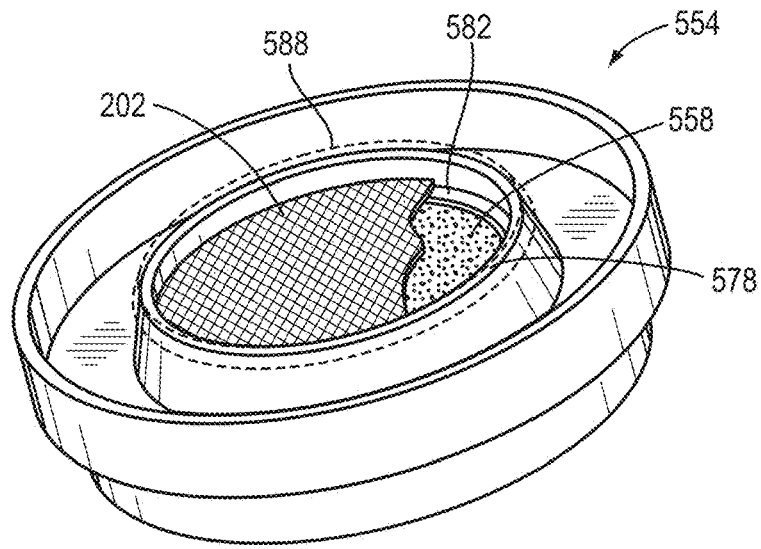
FIG. 9A is a schematic perspective view of the base of FIG. 8A showing a partial cut away view of the membrane and underlying permeable support member.
Figure 9B:
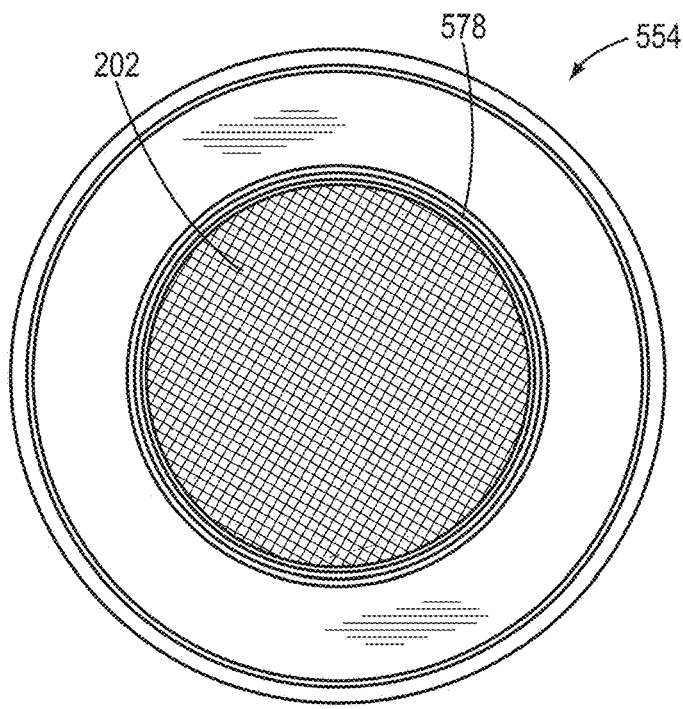
FIGS. 9B-9D are schematic top, bottom, and side views of the base (complete membrane and underlying permeable support member) of FIG. 9A.
Figure 9C:
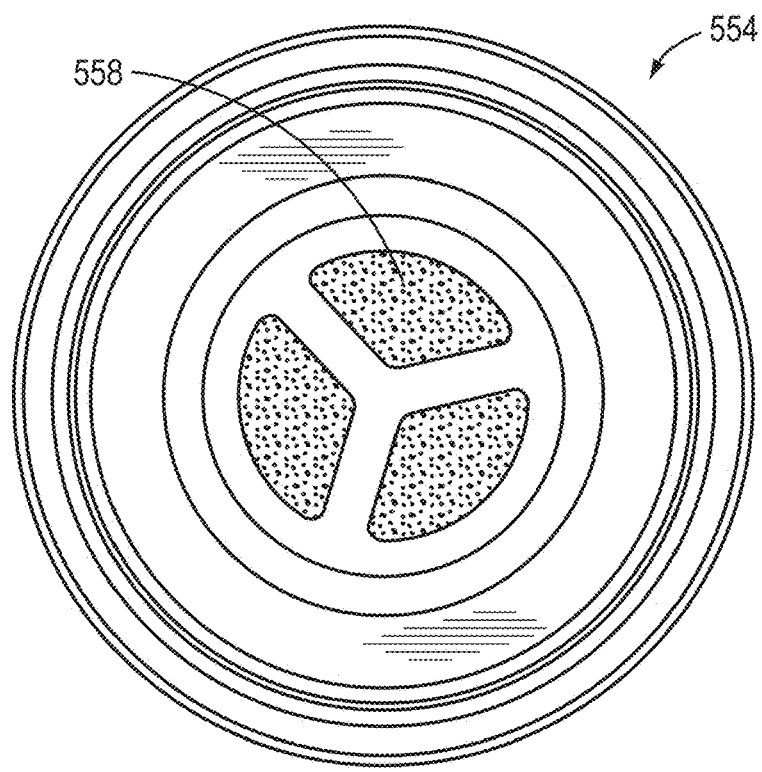
Figure 9D:
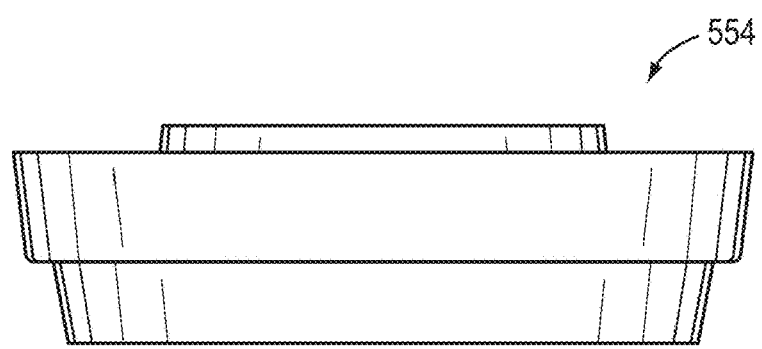

FIGS. 6A-6D depict another embodiment of a cup and base assembly 550. The cup and base assembly 550 has a cup 552 and a base 554 that in many aspects function similarly to the cup 502 and the base 504. The cup and base assembly 550 may also optionally contain a lid 556 for keeping the interior of the cup 552 protected from contaminants, both before and after use. A support member 558 (such as the support 404) is disposed in the base 554 for supporting the membrane 202 (depicted in FIGS. 9A and 9B). In the embodiment depicted, the lid 556 is substantially circular to interfit with cup 552, although any complementary shapes would be suitable. The lid 556 is shown in greater detail in FIGS. 6E and 6F, including ridges 560 that provide a small offset between the top of the cup 552 and a bottom surface of the top of the lid 556.

FIGS. 7A-7D depict the cup 552 in greater detail. The cup 552 includes an upper portion 562 that is substantially hollow and tapers out towards the top to provide an increased sectional area into which fluid may be poured. Further tapering directs the fluid toward a lower section 564 that is adapted to be received within the base 554. A vertical segment 566 can provide increased stability when the cup 552 is disposed within the base 554, from which a lip section 568 (similar to lip section 524) extends at an angle. A further vertical section 570 may also be provided for contacting the membrane 202.

FIGS. 8A-8D depict the base 554. The base 554 includes an outer wall 572 defining an upper portion 574 that may catch extraneous fluid. A lower portion 576 is adapted to be received within a stage (described in detail below), and may be tapered to provide a tight fight when mounted thereon. An interior wall 578 defines a central recess 580 for receiving the cup 552, and more particularly the vertical segment 566. A tight fit and overlap between the vertical segment 566 and the interior wall 578 help ensure a stable fit while the cup 552 is mounted on the base 554. A ledge 582 for receiving the membrane 202 is located at a bottom of the interior wall 578, and further defines a recess 584 in the middle to receive the support member 558. The relationship of the base 554, the membrane 202, and the support member 558 is depicted in FIGS. 9A-9D, along with an optional lid 588 (depicted transparently in FIG. 9A). Openings 586 may be provided in the bottom of the base 554, similar to the openings 512.

In certain embodiments, the cell capture system, in particular the porous membrane, has a sterility assurance level less than $10^{-6}$, $10^{-7}$, $10^{-8}$, or $10^{-9}$. This can be achieved, for example, by sterilizing the cell capture system, via techniques known in the art, for example, via autoclaving, exposure to ionizing radiation, for example, gamma radiation or exposure to a sterilizing fluid or gas, for example, ethylene oxide or vaporized hydrogen peroxide. The cell capture system can be enclosed within a receptacle (e.g., a bag), prior to, during, or after sterilization. The cell capture system can be placed within a receptacle (e.g., a bag) and sealed (e.g., hermetically sealed) before terminal sterilization (e.g., via exposure to ionizing radiation).

In another embodiment, the invention provides a cell capture cup comprising an open cylindrical portion and an annular seal adapted to mate with a base comprising the cell capture system of any one of the foregoing aspects and embodiments. The cell capture cup and base can have a sterility assurance level less than $10^{-6}$, $10^{-7}$, $10^{-8}$, or $10^{-9}$, which can be achieved using any or all of the approaches discussed herein.

(II) Cell Capture Method

Figure 10A:
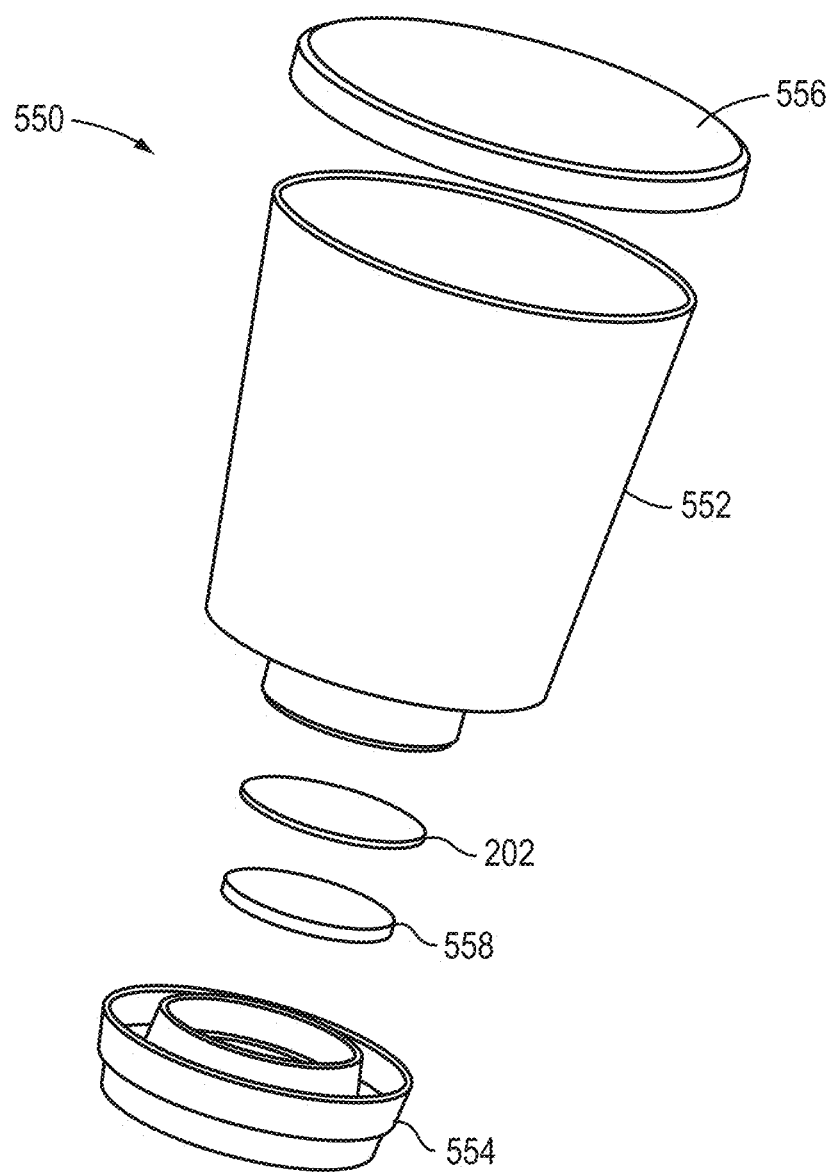
FIG. 10A is a schematic exploded perspective view of the cup assembly of FIG. 6A.
Figure 10B:
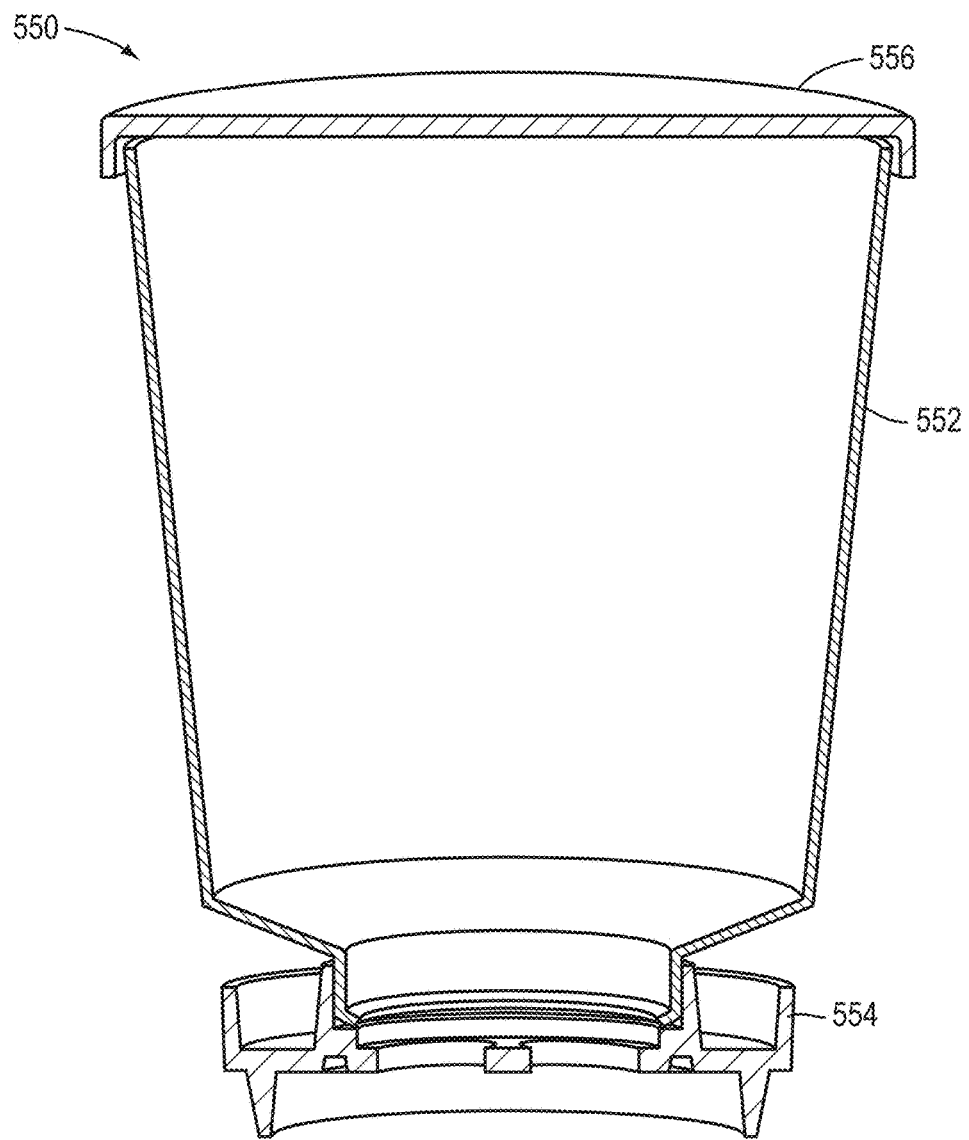
FIG. 10B is a schematic cross-sectional view of the cup assembly of FIG. 6A, without a membrane and a permeable support member.

FIG. 10A depicts the components of an exemplary cup and base assembly 550. The porous support member 558 and the membrane 202 are disposed in the center of the base 554. The cup 552 then is installed on top of the membrane 202, helping to maintain the membrane 202 in a flat position. The lid 556 may be provided on top of the cup 552 to protect the interior of the cup 552 from being contaminated. FIG. 10B depicts the fitting of the components (without the membrane 202 and the support 558.

Figure 10C:
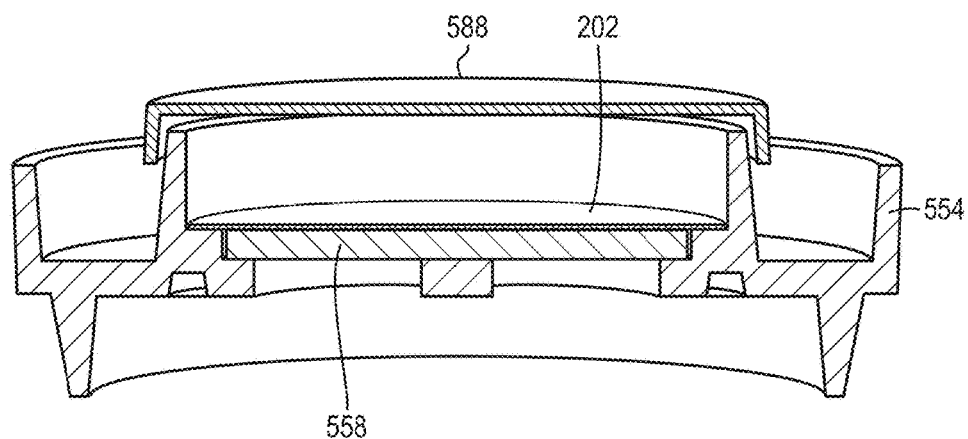
FIG. 10C is a schematic cross-sectional view of the base of FIG. 9A with a membrane, a permeable support member, and a base lid.

During use, a sample fluid is poured into the cup 552. Due to the tapers of the cup 552, the fluid wets the membrane assembly and passes through the membrane 202. The fluid typically passes through the membrane assembly (e.g., through the membrane 202, and the porous support member 558, if one is used) toward the base 554. Negative pressure, for example, a vacuum, can be advantageously employed to draw fluid through the membrane 202 to the openings 586 (e.g., in the embodiment of FIG. 5E, via the grooves 514), and to help keep the membrane substantially flat. After the fluid is drawn through the cup and base assembly 550, any particles and/or cells in the fluid that cannot pass through membrane 202 are retained on the upper exposed surface of the membrane 202. After pouring the fluid into the cup assembly, the cup 552 may be separated from the base 554, as depicted in FIG. 10C, and a lid 558 placed on top of the base 554. The lid 588 may be provided on top of the base 554 to protect the moistened membrane 202 and support 558 from contamination when the base is transferred to the stage 802 (FIG. 11B) or when the base containing membrane 202 is incubated, for example, for 15 minutes to 8 hours to permit the captured viable cells to proliferate.

Figure 11A:
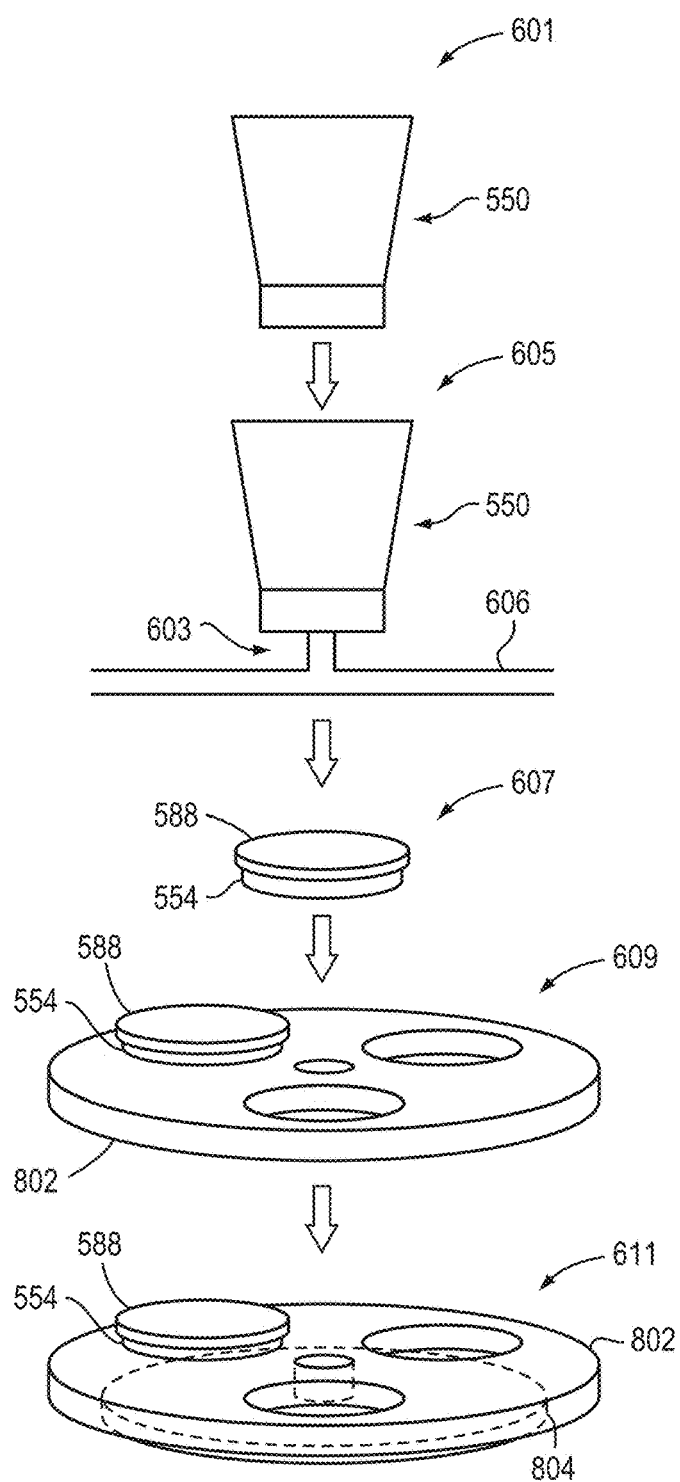
FIG. 11A depicts a process for capturing cells on a permeable membrane.
Figure 11B:
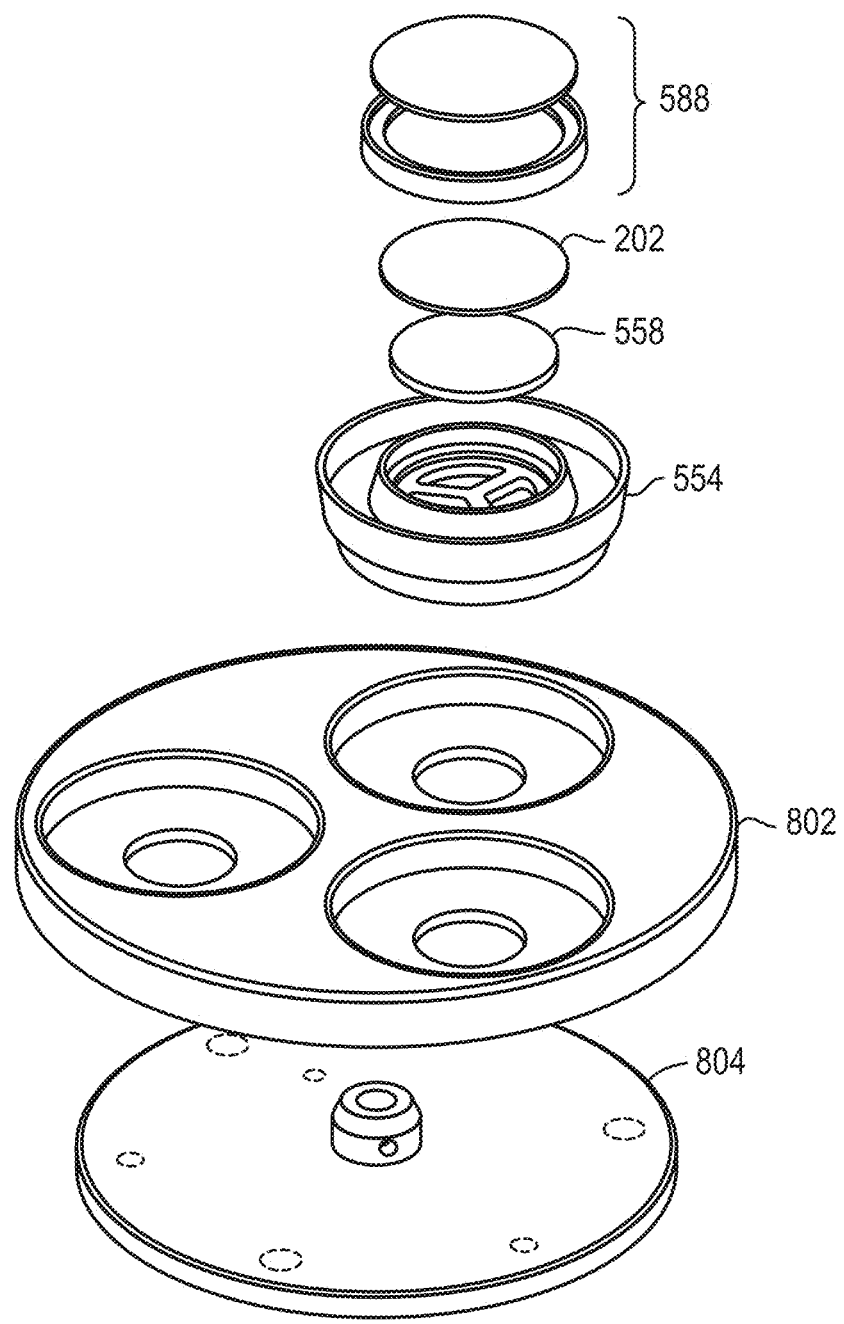
FIG. 11B depicts a schematic exploded perspective view of a chuck, stage, base, support member, membrane, and base lid components.

An exemplary flow chart showing the assembly of the cell capture system, the passage of liquid sample through the cell capture system and the assembly of the membrane holder for use in an exemplary optical detection system is shown in FIG. 11A.

With reference to FIG. 11A, in step 601, a cup and base assembly 550 is provided. In step 603, the cup and base assembly 550 is coupled to a vacuum system (e.g., a vacuum manifold 606) and a negative pressure is applied to the underside of the cup and base assembly 550. In step 605, the liquid sample is poured into the cup and base assembly 550, and any cells present in the liquid sample are retained on the upper exposed surface of the porous membrane 202. This pouring step can occur before, at the same time, or after step 603. It is contemplated that the substantially non-autofluorescent membrane permits a flow rate therethrough of at least 5 or at least 10 mL/cm$^2$/min with a vacuum of about 5 Torr or about 10 Torr. The cells can then be stained with a viability stain or a viability staining system, for example, as discussed in Section III so that it is possible to selectively detect and distinguish viable cells from non-viable cells. The cells may optionally be washed with a physiologically acceptable salt and/or buffer solution to remove residual non-specifically bound fluorescent dye and/or quencher.

In step 607, the membrane assembly is removed from the cup 552, typically in combination with the base 554, though removal independent from the base 554 may be possible. In step 609, the base 554 (and thereby the membrane 202) is disposed on a stage 802. In step 611, the stage 802 is disposed on a chuck 804. The stage 802 and the chuck 804 are described in greater detail below. Steps 609 and 611 may be performed in reverse order or concurrently. The stage 802 and the chuck 804 can be located in the exemplary detection system 100 of FIG. 1A at the start of the process in order to detect any cells (viable and/or non-viable cells) and/or particles captured on the surface of membrane 202. In other embodiments, the stage 802 and/or the chuck 804 may be assembled with the base 554 remote from the detection system 100.

(III) Cell Staining

Once the cells are captured on the permeable membrane, the cells can be stained using a viability stain or a viability staining system so as to detect or otherwise distinguish viable cells from non-viable cells. The particular staining protocol will depend upon a variety of factors, such as, the cells being detected, the stain or staining system being employed, and whether the cells are going to be stained and detected immediately or whether the cells are going to be cultured for a period of time, for example, from 30 minutes to several hours, to permit the cells to proliferate so that a plurality of cells rather than a single cell is detected at a particular locus. Exemplary staining and, where desired, culturing protocols are discussed in the following sections.

It is understood that a variety of stains and staining systems can be used to selectively stain viable versus non-viable cells. As used herein, the term "non-viable cells" is understood to mean cells that are already dead or cells undergoing cell death. Some approaches are based on the principle that viable cells exclude certain reagents, such as trypan blue, alcian blue, eosin Y, nigrosin, propidium iodide, ethidium bromide, and ethidium monoazide. For example, when using trypan blue, the non-viable cells stain blue whereas the viable cells are not stained. Other approaches are based upon the principle that viable cells take up and/or modify certain reagents (for example, fluorescent dyes), where non-viable cells do not. Dyes that selectively label either viable cells or non-viable cells are described in U.S. Pat. No. 5,534,416 and PCT Publication No. WO92/02632, which include esterase-dependent dyes, nucleic acid binding dyes, dyes dependent upon intracellular oxidation, and membrane potential sensitive dyes.

It is understood that the viability stains and viability staining systems that selectively label viable cells can use a variety of principles. For example, the fluorescent dyes may penetrate both viable and non-viable cells, but the fluorescent dyes may become modified in a viable cell such that fluorescent dye becomes activated within the viable cell (for example, the activated dye may bind to a cellular substrate or cellular organelle or the like, or may become capable of fluorescence emission upon illumination with excitation light), or made insoluble within the viable cell. The modification can occur as result of metabolic activity within the cell, for example, via enzymatic activity within the cell. By way of example, the fluorescent dye optionally contains a substrate for an esterase enzyme. Other systems may use a combination of a fluorescent dye and a quencher or two or more different quenchers that quench the emission from the fluorescent dye upon excitation. Other systems may use a plurality of fluorescent dyes or a combination of a dye and quencher, where the emission profile (for example, emission wavelength) is modulated by the presence of a second fluorescent dye or the quencher. It is understood that in, each of the foregoing systems, a plurality of different fluorescent dyes can be employed, for example, 2, 3, 4, or 5 different fluorescent dyes that target and/or stain different cells or cell types, organelles, structures, proteins, glycoproteins, lipids, glycolipids, nucleic acids, carbohydrates, etc., to increase confidence that a fluorescent event is actually caused by a cell rather than a non-specific acellular event.

By way of example, viability stains that can be activated within viable cells, for example, via metabolic activity (for example, esterase enzymatic activity) within the cells, are described in U.S. Pat. Nos. 5,314,805, and 5,534,416, U.S. Patent Application Publication No. US2008/0305514, and PCT Publication No. WO92/02632. In one embodiment, the fluorescent dye can contain an esterase substrate. An esterase substrate membrane permeable dye becomes chemically modified via an esterase enzyme in a viable cell that creates carboxyl groups that trap the modified fluorescent dye within intact, viable cells. In these cases, the background can be reduced by using a membrane impermeable quencher or with a mild detergent to remove any fluorescence from extracellular regions or non-viable cells. In such an approach, only the viable cells are detected. Exemplary esterase substrate-based membrane permeable dyes are discussed in U.S. Pat. No. 5,534,416, including without limitation, Calcein Blue AM, Carboxycalcein Blue AM, Fluorescein diacetate, carboxyfluorescein diacetate, 5-carboxyfluoresein diacetate AM, sulfofluorescein diacetate, BCECF-AM, and Calcein AM.

Fluorescent dyes that preferentially label non-viable cells rather than viable cells (for example, permeate the membranes of non-viable rather than viable cells) include for example, PO-PRO-1, BO-PRO-1, YO-PRO-1, TO-PRO-1, PO-PRO-3, BO-PRO-3, YO-PRO-3, TO-PRO-3, POPO-1, BOBO-1, YOYO-1, POPO-3, BOBO-3, YOYO-3 and ethidium bromide (U.S. Pat. No. 5,534,416).

In addition, it is completed that the fluorescent dyes useful in the practice of the invention include dyes that bind to nucleic acids within the cells. The dyes can permeate and bind to nucleic acids in viable cells, permeate and bind nucleic acids in non-viable cells, or permeate and bind nucleic acids in viable and non-viable cells. The choice of the dye will depend upon the detection protocol to be employed.

A variety of viability staining systems have been developed and are described, for example, in U.S. Patent Publication 2008/0305514, U.S. Pat. Nos. 5,314,805, and 5,534,416, Canadian Patent application CA 02236687, and PCT Publication WO2011/124927, where the viable cells are labeled with one fluorescent dye, and the non-viable cells are labeled with a second, different fluorescent dye. In other words, the non-viable cells are still fluorescent, however, the fluorescence emissions from the dead cells can be distinguished from the fluorescent emissions from the viable cells.

Canadian Patent Application No. 02236687 describes a system that employs two different fluorescent dyes, a first dye that is capable of non-specific transfer across a selective membrane which labels all cells, and a second dye that is incapable of moving across a selective membrane and can only enter cells that have compromised membranes. In this case, the viable cells are labeled with the first dye and the non-viable cells are labeled with the first and second dyes. Given the differences in the emission spectra of viable and non-viable cells, it is possible to distinguish the viable cells from the non-viable cells. The non-viable cells, however, still generate a fluorescent signal when irradiated with light of the appropriate wavelength.

U.S. Patent Publication 2008/0305514 describes a system where a first fluorescent dye, for example, a fluorescent dye containing an esterase substrate, permeates and selectively labels viable cells, and a second, different nucleic acid binding fluorescent dye permeates both viable and non-viable cells and stains the nucleic acid present in both viable and non-viable cells. In this approach, a fluorescent dye can be, for example, an esterase substrate that has a high intracellular retention because the esterase in viable cells converts the dye into a form that can no longer traverse the cellular membrane. The approach can also employ a nucleic acid stain (for example, a 4',6-diamidino-2-phenylindole dye) that labels both viable and non-viable cells. When excited with the appropriate wavelengths of light, the viable cells emit light from both the first and second fluorescent dyes (i.e., there are two different fluorescent events) whereas the non-viable cells emit light from just the second fluorescent dye. The use of both the viability stain (for example, the esterase substrate) and the nucleic acid stain can increase confidence that a fluorescent event is actually caused by a cell and not via a non-specific event. The non-viable cells still generated a fluorescent signal when irradiated with light of the appropriate wavelength.

U.S. Pat. No. 5,314,805 describes a different system that employs two different fluorescent dyes. A first fluorescent dye, for example, calcein AM (an esterase substrate), permeates and selectively labels viable cells. Viable cells are detectable by a green fluorescent signal generated upon enzymatic hydrolysis of calcein AM. Non-viable cells are detected with a second different fluorescent dye, for example, ethidium homodimer. Non-viable cells are detectable by red fluorescence resulting from nucleic acids stained with the ethidium homdimer. As a result, it is possible to distinguish between viable and non-viable cells based upon the emission profile of each cell. The non-viable cells still generate a fluorescent signal when irradiated with light of the appropriate wavelength.

U.S. Pat. No. 5,534,416 describes a different system that employs two different fluorescent dyes. A first fluorescent dye, a cyclic-substituted unsymmetrical cyanine dye, stains all cells (both viable cells and non-viable cells). The second fluorescent dye, is a dye that selectively labels either viable cells or non-viable cells and gives a fluorescence response that is different from the first fluorescent dye. When the second fluorescent dye is a dye that selectively stains viable cells, the viable cells are stained with the first and second dyes, and the non-viable cells are stained with the first dye. In contrast, when the second fluorescent dye is a dye that selectively stains non-viable cells, the viable cells are stained with the first dye and the non-viable cells are labeled with the first and second dyes. During either approach, given the differences in the emission spectra of viable and non-viable cells, it is possible to distinguish the viable cells from the non-viable cells. The non-viable cells, however, still generate a fluorescent signal when irradiated with light of the appropriate wavelength.

In certain staining systems, the fluorescent dyes traverse the intact membranes of viable cells but become insoluble or trapped within viable cells as a result of metabolic activity within the cells. Furthermore, the fluorescent dyes can be used with one or more quenchers that selectively enter non-viable cells, which therefore increase the selectivity for a fluorescent event emanating from viable cells. In other circumstances, the fluorescent dyes may permeate both viable and non-viable cells. In this scenario, the fluorescent dye can be used with one or more quenchers that selectively permeate non-viable cells, which therefore increase selectively for a fluorescent event emanating from viable cells.

In an alternative approach, U.S. Patent Application Publication No. US2006/0040400 and European Application No. EP 1624 071 describes the use of a fluorescent dye and a quencher. A fluorescent dye (for example, carboxyfluorescein diacetate) permeates both viable and non-viable cells. The quencher then is added to the fluorescently stained cells that is capable of permeating the membrane of a viable cell but does not quench the fluorescence of the fluorescent dye at the pH in the viable cells, but quenches the fluorescence at a pH substantially different from the pH of the viable cells. In this approach, the quencher is added to the cells at a pH that is substantially different from the pH value of the viable cells. In this approach, the quencher is not operative to quench fluorescence at the pH of viable cells but quenches fluorescence at the pH of non-viable cells.

Despite the cell viability stains and viability staining systems available and useful in the practice of the methods and systems described herein, there is a desire to develop a simple, rapid, robust staining protocol that can be used to selectively detect viable cells (both single cells and clusters of cells) with little or no background fluorescence emanating from non-viable cells, especially under the conditions (for example, using the excitation light) used to excite the viable cells and/or the system (e.g., membrane, solid support, optical cell or flow cell) containing or supporting the cells. In addition, the staining system should not compromise the viability of the cells being detected. Furthermore, as discussed below, if desired, the staining system should permit the simultaneous proliferation and staining of viable cells in the cell sample.

The invention provides a method for selectively labeling viable cells (for example, prokaryotic cells or eukaryotic cells) in a cell containing sample. The staining method can be used in combination with a cell capture system and/or an optical detection system for detecting the presence of viable cells in a cell sample. The staining procedure can be used to stain viable cells disposed upon a solid support, for example, microscope slide and/or a well in a culture plate, or within a liquid sample, for example, within an optical cell or a flow cell. The staining protocol can be used in a method to measure the bioburden (for example, to measure the number and/or percentage and/or fraction of viable cells (for example, viable microorganisms, for example, bacteria, yeast, and fungi)) of a particular sample of interest.

The invention provides a method of detecting viable cells in a cell sample. The method comprises exposing cells in the cell sample to (i) a membrane permeable fluorescent dye under conditions that permit the fluorescent dye to permeate both viable and non-viable cells, and (ii) a membrane impermeable fluorescence quencher capable of quenching fluorescence produced by the fluorescent dye under conditions to permit the quencher to selectively permeate non-viable cells but not viable cells. Thereafter, the method comprises exposing the cells to a beam of light having a wavelength capable of exciting the fluorescent dye to produce a fluorescent emission, and detecting the fluorescent emission, if any, from the cells with a detector (e.g., a single detector that detects a single wavelength range or a plurality of different wavelength ranges) or a plurality of detectors (e.g., different detectors each capable of detecting a different wavelength range), thereby to detect the viable cells in the cell sample. The fluorescent dye within the non-viable cells emits substantially less fluorescence than the fluorescent dye within the viable cells. As a result, the non-viable cells emit substantially less fluorescence than the viable cells.

Under certain circumstances, for example, when the quencher is capable of creating fluorescent emissions, the wavelength of the excitation light can be selected so as not to photoexcite, or substantially not to photoexcite, the quencher. Alternatively, the detector can be chosen and/or configured so as to preferentially detect the emission events from the dye rather than the emission events from the quencher.

In addition, the invention provides a method of detecting viable cells in a cell sample. The method comprises exposing cells in the cell sample to (i) a membrane permeable fluorescent dye under conditions that permit the fluorescent dye to permeate both viable and non-viable cells, and (ii) a membrane impermeable fluorescence quencher capable of quenching fluorescence produced by the fluorescent dye under conditions to permit the quencher to selectively permeate non-viable cells but not viable cells. Thereafter, the cells are exposed to light having a wavelength capable of exciting the fluorescent dye to produce a fluorescent emission. The fluorescent emission, if any, from the cells, is detected with one or more detectors configured to preferentially detect a detectable emission from the fluorescent dye rather than a detectable emission from the quencher so that the detectable emission from the quencher, if created, is no greater than 50% (e.g., no greater than 40%, no greater than 30%, no greater than 20%, no greater than 10%) of the detectable emission from the fluorescent dye. As a result, under the detection conditions employed, the non-viable cells emit substantially less fluorescence detected by the detector than the viable cells. As a result, the method can be used to detect the viable cells in the cell sample.

In certain embodiments, the non-viable cells emit no or substantially no fluorescence detectable by the detector upon exposure to the light. In certain other embodiments, the non-viable cells emit no or substantially no fluorescence upon exposure to the beam of light.

It is understood that the choice of the appropriate dye-quencher pair depends upon a number of factors including one or more of: the emission spectrum of the dye, the absorbance spectrum of the quencher, the emission spectrum of the quencher, if the quencher has an emission spectrum, and the bandwidth of detection in a given detector. Each of these features are discussed below.

In general, exemplary membrane permeable fluorescent dyes useful in the practice of this method have one or more of the following features: fluorescent when exposed to a beam of light having a wavelength maxima in the range of from about 350 nm to about 1000 nm, water soluble with or without a surfactant such as a mild detergent or cyclodextrin carrier agent, non-toxic at concentrations required for detectable staining, and a hydrophobic character that allows for passive diffusion through a viable cell membrane. In certain embodiments, the membrane permeable fluorescent dye may also be characterized as containing at least one charged group (e.g., a quaternary nitrogen group). In certain embodiments, the fluorescent dye can be excited to undergo fluorescence by radiation from a red laser, for example, a red laser that emits light having a wavelength in the range of 620 nm to 640 nm.

In addition, exemplary membrane impermeable fluorescent quenchers useful in the practice of this method have one or more of the following features: non-toxic at concentrations sufficient for quenching signal from the fluorescent dye, water soluble, hydrophilic and polar containing either highly charged groups such as but not limited to carboxyl, amino, phenoxide, sulfate, sulfonate, phosphate, or phosphonate moieties, and/or substituted with polar ligands such as polyethylene glycol, polypropylene glycol, or polyvinyl alcohol, so that the polarity of the quencher prevents passive diffusion through a viable cell membrane and/or is actively pumped out of a viable cell. In certain embodiments, the membrane impermeable fluorescent quencher optionally contains at least two charged groups (e.g., at least one quaternary nitrogen group). In another embodiment, the quencher does not fluorescence when exposed to light having a wavelength, a wavelength range, or a plurality of wavelength ranges, that is emitted from the membrane permeable fluorescent dye when excited by the light source used for detecting the presence of viable cells.

Exemplary fluorescent dye and fluorescence quencher pairs can be selected for use in the practice of the inventions described herein and can be chosen, for example, from the fluorescent dyes and fluorescence quenchers set forth in TABLES I and II below.

Exemplary fluorescent dyes (e⁻ acceptors) can be selected from Oxazine 1, Oxazine 170, Oxazine 750, Oxazine 4, Rhodamine 700, Rhodamine 800, Cresyl Violet, Nile blue, Methylene Blue, Azure A, Azure B and Azure C, which can be used in combination with an exemplary quencher (e⁻ donor) selected from sodium ascorbate, 5'guanosine monophosphate, L-tryptophan, potassium hexacyanoferrate (II), diphenylamine-2-sulfonic acid, copper phthalocyanine-3,4', 4'',4'''-tetrsulfonic acid tetrasodium salt and humic acid.

Exemplary fluorescent dyes (e⁻ donors) can be selected from metallated phthalocyanines or porhyrins, Hoeschst 33342, and other Hoeschst dyes, Ru(phen_dppz$^{2+}$ and Rh(phi)bpy$^{3+}$, which can be used in combination with a quencher (e⁻ acceptor) selected from bipyridinium derivatives (for example, N,N'-dimethyl-4,4'-bipyridinium dichloride, 1,1'-ethylene-2,2'-bipyridyyldiylium dibromide, and anthraquinones (for example, bisalkylaminoanthraquinones).

TABLE I

EXEMPLARY FLUORESCENT DYES

| Dye No. | Fluorescent Dye | Structure | Source | Fluorescent Profile Excitation (λ max) Emission (λ max) | Exemplary Excitation Wavelength (nm) | Typical PET Quencher |
|---|---|---|---|---|---|---|
| D1 | Oxazine 1 Pechlorate | 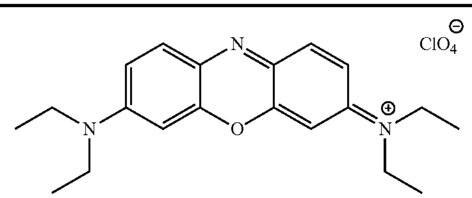 | Sigma-Aldrich, St. Louis, MO | Excitation: 643 nm Emission: 665 nm | 640 nm | Electron donor |
| D2 | Oxazine 170 Perchlorate | 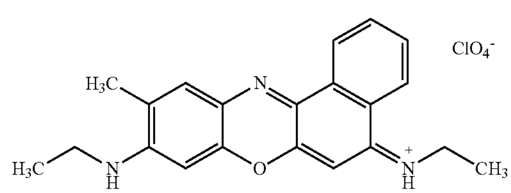 | Sigma-Aldrich, St. Louis, MO | Excitation: 613 nm Emission: 641 nm | 532 nm, 640 nm | Electron donor |

TABLE I-continued

EXEMPLARY FLUORESCENT DYES

| Dye No. | Fluorescent Dye | Structure | Source | Fluorescent Profile Excitation (λ max) Emission (λ max) | Exemplary Excitation Wavelength (nm) | Typical PET Quencher |
|---|---|---|---|---|---|---|
| D3 | Oxazine 750 Perchlorate | 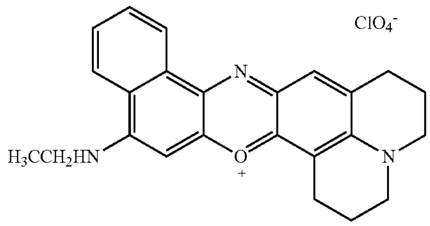 | Sigma-Aldrich, St. Louis, MO | Excitation: 685 nm Emission: 695 nm | 640 nm | Electron donor |
| D4 | Rhodamine 6G | 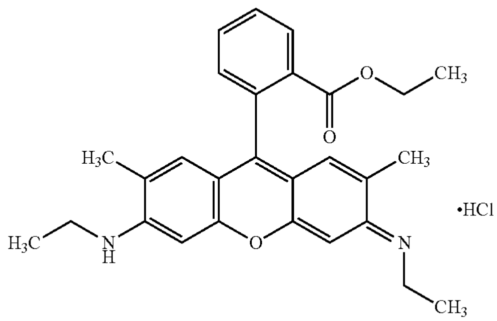 [SMILES: CC/N=c1\cc2oc3cc(NCC)c(C)cc3c(-c3ccccc3C(=O)OCC)c-2cc1C ; Cl] | Sigma-Aldrich, St. Louis, MO | Excitation: 524 nm Emission: 552 nm | 488 nm, 532 nm | Electron donor |
| D5 | Rhodamine B | 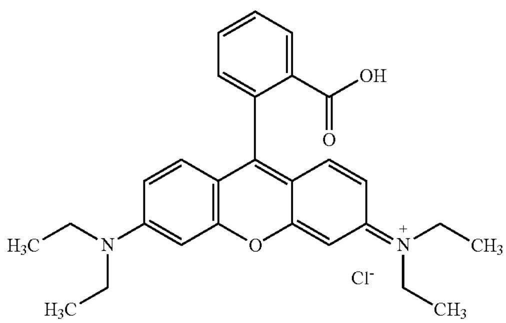 | Sigma-Aldrich, St. Louis, MO | Excitation: 545 nm Emission: 565 nm | 488 nm, 532 nm | Electron donor |
| D6 | Rhodamine 700 | 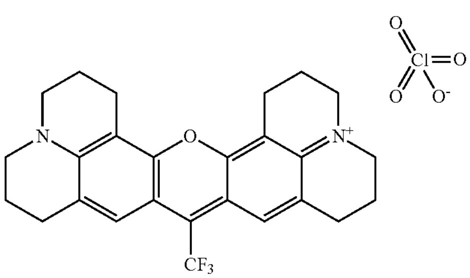 [SMILES: FC(F)(F)C1=c2cc3c4c(c2Oc2c1cc1c5c2CCCN5CCC1)CCC[N+]=4CCC3 ; [O-][Cl+3]([O-])([O-])[O-]] | AnaSpec, Fremont, CA | Excitation: 643 nm Emission: 664 nm | 640 nm | Electron donor |
| D7 | Rhodamine 800 | 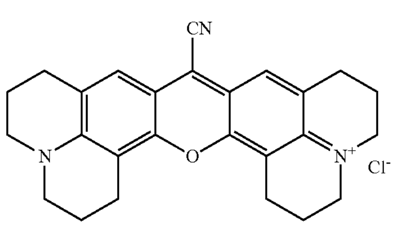 [SMILES: N#CC1=c2cc3c4c(c2Oc2c1cc1c5c2CCCN5CCC1)CCC[N+]=4CCC3 ; [Cl-]] | Sigma-Aldrich, St. Louis, MO | Excitation: 682 nm Emission: 712 nm | 640 nm | Electron donor |

TABLE I-continued

EXEMPLARY FLUORESCENT DYES

| Dye No. | Fluorescent Dye | Structure | Source | Fluorescent Profile Excitation (λ max) Emission (λ max) | Exemplary Excitation Wavelength (nm) | Typical PET Quencher |
|---|---|---|---|---|---|---|
| D8 | Acridine Orange | (structure) ·xH₂O ·HCl | Sigma-Aldrich, St. Louis, MO | Excitation: 502 nm Emission: 525 nm | 488 nm | Electron acceptor |
| D9 | 4',6-diamidino-2-phenylindole (DAPI) | (structure) | Sigma-Aldrich, St. Louis, MO | Excitation: 358 nm Emission: 461 nm | 355 nm | Electron acceptor |
| D10 | Hoechst 33258 | (structure) ·3HCl ·xH₂O | Sigma-Aldrich, St. Louis, MO | Excitation: 355 nm Emission: 465 nm | 355 nm | Electron acceptor |
| D11 | Hoechst 33342 | (structure) ·3HCl | Sigma-Aldrich, St. Louis, MO | Excitation: 355 nm Emission: 465 nm | 355 nm | Electron acceptor |
| D12 | BOXTO | | TATAA Biocenter, San Francisco, CA | Excitation: 515 nm Emission: 552 nm | 488 nm | Electron acceptor |
| D13 | Vybrant DyeCycle Violet | | Life Technologies Inc., Grand Island, NY | Excitation: 369 nm Emission: 437 nm | 365 nm, 405 nm | Electron acceptor |
| D14 | Vybrant DyeCycle Green | | Life Technologies Inc., Grand Island, NY | Excitation: 506 nm Emission: 534 nm | 488 nm | Electron acceptor |
| D15 | Vybrant DyeCycle Orange | | Life Technologies Inc., Grand Island, NY | Excitation: 519 nm Emission: 563 nm | 488 nm, 532 nm | Electron acceptor |
| D16 | Vybrant DyeCycle Ruby | | Life Technologies Inc., Grand Island, NY | Excitation: 638 nm Emission: 686 nm | 488 nm, 532 nm, 633 nm | Electron acceptor |

TABLE I-continued

EXEMPLARY FLUORESCENT DYES

| Dye No. | Fluorescent Dye | Structure | Source | Fluorescent Profile Excitation (λ max) Emission (λ max) | Exemplary Excitation Wavelength (nm) | Typical PET Quencher |
|---|---|---|---|---|---|---|
| D17 | Draq5 | 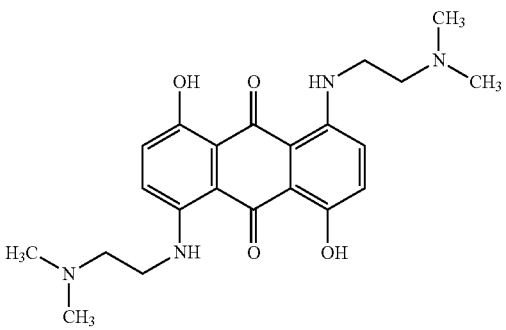 | BioStatus Limited, Leicestershire, UK | Excitation: 488-647 nm Emission: 697 nm | 488 nm, 532 nm, 633 nm | Electron donor |
| D18 | CYTRAK Orange | | BioStatus Limited, Leicestershire, UK | Excitation: 515 nm Emission: 605 nm | 488 nm, 532 nm | Electron donor |
| D19 | Tris (bipyridine) ruthenium (II) dichloride | 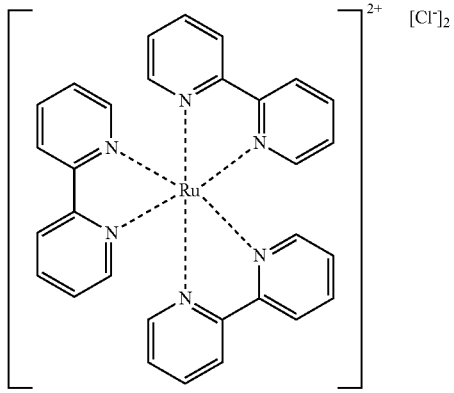 | Sigma-Aldrich, St. Louis, MO | Excitation: 452 nm Emission: 623 nm | 355 nm, 488 nm | Electron acceptor |
| D20 | Cresyl Violet Perchlorate | 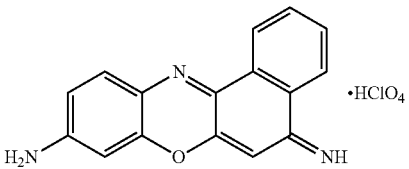 | Sigma-Aldrich, St. Louis, MO | Excitation: 602 nm Emission: 614 nm | 532 nm | Electron donor |
| D21 | SYTO 9 | | Life Technologies Inc., Grand Island, NY | Excitation: 485 nm Emission: 498 nm | 488 nm | Electron acceptor or donor |
| D22 | SYTO 11 | | Life Technologies Inc., Grand Island, NY | Excitation: 508 nm Emission: 527 nm | 488 nm | Electron acceptor or donor |
| D23 | SYTO 12 | | Life Technologies Inc., Grand Island, NY | Excitation: 499 nm Emission: 522 nm | 488 nm | Electron acceptor or donor |
| D24 | SYTO 13 | | Life Technologies Inc., Grand Island, NY | Excitation: 488 nm Emission: 509 nm | 488 nm | Electron acceptor or donor |
| D25 | SYTO 14 | | Life Technologies Inc., Grand Island, NY | Excitation: 517 nm Emission: 549 nm | 488 nm | Electron acceptor or donor |

TABLE I-continued

EXEMPLARY FLUORESCENT DYES

| Dye No. | Fluorescent Dye | Structure | Source | Fluorescent Profile Excitation (λ max) Emission (λ max) | Exemplary Excitation Wavelength (nm) | Typical PET Quencher |
|---|---|---|---|---|---|---|
| D26 | SYTO 16 | | Life Technologies Inc., Grand Island, NY | Excitation: 488 nm Emission: 518 nm | 488 nm | Electron acceptor or donor |
| D27 | SYTO 18 | | Life Technologies Inc., Grand Island, NY | Excitation: 490 nm Emission: 507 nm | 488 nm | Electron acceptor or donor |
| D28 | SYTO 21 | | Life Technologies Inc., Grand Island, NY | Excitation: 494 nm Emission: 517 nm | 488 nm | Electron acceptor or donor |
| D29 | SYTO 24 | | Life Technologies Inc., Grand Island, NY | Excitation: 490 nm Emission: 515 nm | 488 nm | Electron acceptor or donor |
| D30 | SYTO 25 | | Life Technologies Inc., Grand Island, NY | Excitation: 521 nm Emission: 556 nm | 488 nm, 532 nm | Electron acceptor or donor |
| D31 | SYTO BC | | Life Technologies Inc., Grand Island, NY | Excitation: 485 nm Emission: 500 nm | 488 nm | Electron acceptor or donor |
| D32 | SYTO 80 | | Life Technologies Inc., Grand Island, NY | Excitation: 531 nm Emission: 545 nm | 488 nm, 532 nm | Electron acceptor or donor |
| D33 | SYTO 81 | | Life Technologies Inc., Grand Island, NY | Excitation: 530 nm Emission: 544 nm | 488 nm, 532 nm | Electron acceptor or donor |
| D34 | SYTO 82 | | Life Technologies Inc., Grand Island, NY | Excitation: 541 nm Emission: 560 nm | 488 nm, 532 nm | Electron acceptor or donor |
| D35 | SYTO 83 | | Life Technologies Inc., Grand Island, NY | Excitation: 543 nm Emission: 559 nm | 488 nm, 532 nm | Electron acceptor or donor |
| D36 | SYTO 84 | | Life Technologies Inc., Grand Island, NY | Excitation: 567 nm Emission: 582 nm | 488 nm, 532 nm | Electron acceptor or donor |
| D37 | SYTO 85 | | Life Technologies Inc., Grand Island, NY | Excitation: 567 nm Emission: 583 nm | 488 nm, 532 nm | Electron acceptor or donor |
| D38 | SYTO 17 | | Life Technologies Inc., Grand Island, NY | Excitation: 621 nm Emission: 634 nm | 580 nm | Electron acceptor or donor |
| D39 | SYTO 59 | | Life Technologies Inc., Grand Island, NY | Excitation: 622 nm Emission: 645 nm | 580 nm, 633 nm | Electron acceptor or donor |
| D40 | SYTO 60 | | Life Technologies Inc., Grand Island, NY | Excitation: 652 nm Emission: 678 nm | 633 nm | Electron acceptor or donor |
| D41 | SYTO 61 | | Life Technologies Inc., Grand Island, NY | Excitation: 628 nm Emission: 645 nm | 580 nm, 633 nm | Electron acceptor or donor |
| | | | Life | Excitation: | 633 nm | Electron |

TABLE I-continued

EXEMPLARY FLUORESCENT DYES

| Dye No. | Fluorescent Dye | Structure | Source | Fluorescent Profile Excitation ($\lambda$ max) Emission ($\lambda$ max) | Exemplary Excitation Wavelength (nm) | Typical PET Quencher |
|---|---|---|---|---|---|---|
| D42 | SYTO 62 | | Technologies Inc., Grand Island, NY | 652 nm Emission: 676 nm | | acceptor or donor |
| D43 | SYTO 63 | | Life Technologies Inc., Grand Island, NY | Excitation: 657 nm Emission: 673 nm | 633 nm | Electron acceptor or donor |
| D44 | SYTO 64 | | Life Technologies Inc., Grand Island, NY | Excitation: 599 nm Emission: 619 nm | 580 nm | Electron acceptor or donor |

TABLE II

EXEMPLARY FLUORESCENCE QUENCHERS

| Quencher No. | Quencher | Structure | Source | PET Profile | FRET Quenching Applicable Range |
|---|---|---|---|---|---|
| Q1 | Sodium Ascorbate | 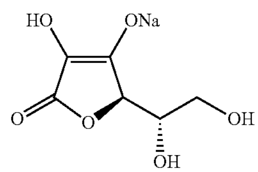 | Sigma-Aldrich, St. Louis, MO | Electron donor | N/A |
| Q2 | Potassium hexacyanoferrate (II) | 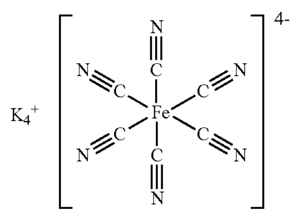 | Sigma-Aldrich, St. Louis, MO | Electron donor | N/A |
| Q3 | Guanosine 5'-monophosphate sodium salt | 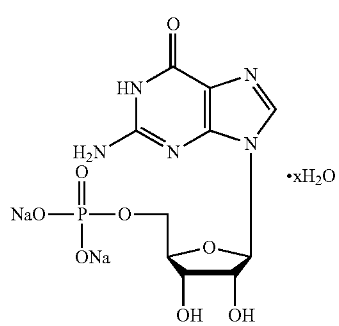 | Sigma-Aldrich, St. Louis, MO | Electron donor | N/A |
| Q4 | Sodium diphenylamine-4-sulfonate | 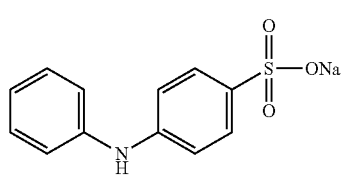 | Sigma-Aldrich, St. Louis, MO | Electron donor | N/A |

TABLE II-continued

EXEMPLARY FLUORESCENCE QUENCHERS

| Quencher No. | Quencher | Structure | Source | PET Profile | FRET Quenching Applicable Range |
|---|---|---|---|---|---|
| Q5 | 4-Sulfocalix[6]arene | (structure) | Tokyo Chemical Industry Co., Ltd., Portland, OR | Electron donor | N/A |
| Q6 | 4-Sulfocalix[8]arene | (structure) | Tokyo Chemical Industry Co., Ltd., Portland, OR | Electron donor | N/A |
| Q7 | Methyl viologen | (structure) | Sigma-Aldrich, St. Louis, MO | Electron acceptor | N/A |

TABLE II-continued

EXEMPLARY FLUORESCENCE QUENCHERS

| Quencher No. | Quencher | Structure | Source | PET Profile | FRET Quenching Applicable Range |
|---|---|---|---|---|---|
| Q8 | Sodium 2-anthraquinone-sulfonate | 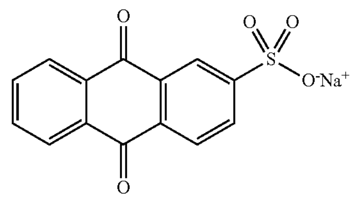 | Sigma-Aldrich, St. Louis, MO | Electron acceptor | N/A |
| Q9 | Potassium hexacyano-ferrate (III) | 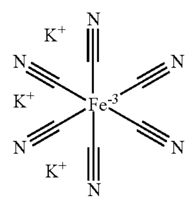 | Sigma-Aldrich, St. Louis, MO | Electron acceptor | N/A |
| Q10 | Tartazine | 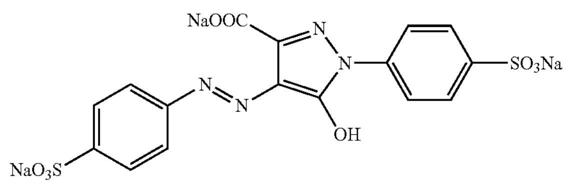 | Sigma-Aldrich, St. Louis, MO | N/A | 400-500 nm |
| Q11 | Amaranth | 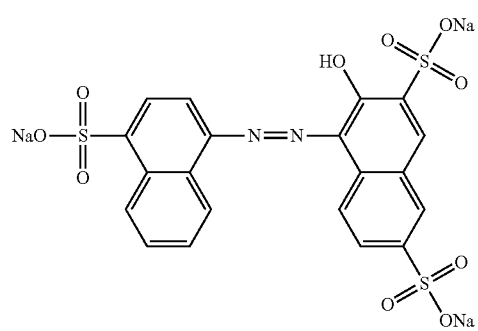 | Sigma-Aldrich, St. Louis, MO | N/A | 500-600 nm |
| Q12 | Trypan Blue | 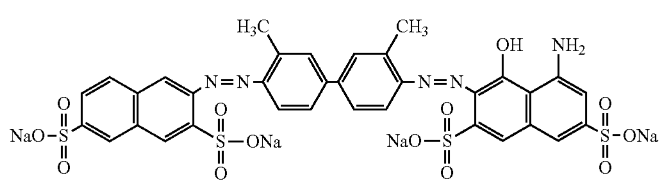 | Sigma-Aldrich, St. Louis, MO | N/A | 550-650 nm |
| Q13 | Naphthol Green B | 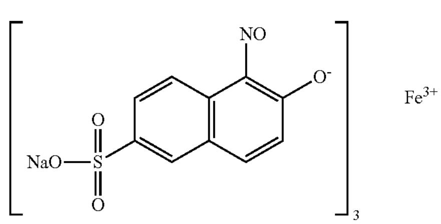 | Sigma-Aldrich, St. Louis, MO | N/A | 600-750 nm |

TABLE II-continued

EXEMPLARY FLUORESCENCE QUENCHERS

| Quencher No. | Quencher | Structure | Source | PET Profile | FRET Quenching Applicable Range |
|---|---|---|---|---|---|
| Q14 | IR-783 | 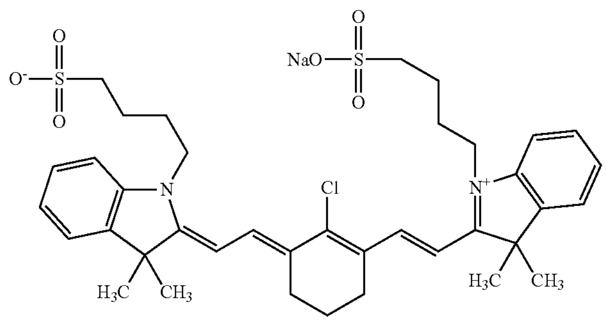 | Sigma-Aldrich, St. Louis, MO | N/A | 600-780 nm |
| Q15 | Copper phthalocyanine-3,4',4'',4'''-tetrasulfonic acid tetrasodium salt | 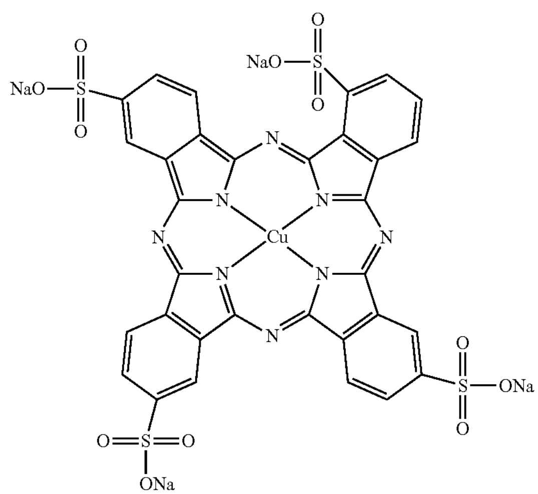 | Sigma-Aldrich, St. Louis, MO | Electron donor and acceptor | 500-700 nm |
| Q16 | (3-{[4-chloro-9,10-dioxo-5,8-bis({[3-trimethylammonio)propyl]amino})anthracen-1-yl]amino}propyl)trimethylazanium trihalide | X⁻ = Cl⁻, Br⁻, or I⁻ | | Electron acceptor | 400-750 nm |

TABLE II-continued

EXEMPLARY FLUORESCENCE QUENCHERS

| Quencher No. | Quencher | Structure | Source | PET Profile | FRET Quenching Applicable Range |
|---|---|---|---|---|---|
| Q17 | (3-{[9,10-dioxo-4,5,8-tris({[3-trimethyl-ammonio)propyl]amino})anthracen-1-yl]amino}propyl)trimethyl-azanium tetrahalide | [structure shown; $X^- = Cl^-, Br^-, or\ I^-$] | | Electron acceptor | 500-800 nm |
| Q18 | N-methyl-4-[(4-{methyl[3-(trimethyl-ammonio)propyl]amino}phenyl)imino]-N-[2-(trimethyl-ammonio)ethyl]cyclohexa-2,5-dien-1-Iminium trihalide | [structure shown; $X^- = Cl^-, Br^-, or\ I^-$] | | Electron acceptor | 550-800 nm |
| Q19 | Draq7 | | BioStatus Limited, Leicestershire, UK | Electron acceptor | 400-640 nm |

The membrane impermeable quenchers for use in the practice of the inventions described herein typically suppress fluorescence from the fluorescent dye by either photo-induced electron transfer (PET), sometimes referred to as static quenching, or fluorescence resonance energy transfer (FRET), or some combination thereof. The efficiency of these quenching mechanisms are distance-dependent, meaning that the fluorescent dye molecule and quencher molecule must be in close enough proximity for the suppression of fluorescence to take place. It is possible to select the conditions to maximize the chances that efficient quenching can be accomplished. An exemplary, spectral overlap between the fluorescent dye and quencher is shown schematically in FIG. 12A. In such a system, the fluorescent emission of the fluorescent dye is suppressed by the quencher via a FRET mechanism. Using such principles it is possible to create fluorescent dye-quencher pairs useful in the practice of the invention.

In one approach, the fluorescent dye-quencher pairs can be selected to have a binding affinity for one another, by means of, for example, electrostatic and/or hydrophobic interactions, which when bound results in a substantially non-fluorescent ground-state complex. In other words, the fluorescent dye and fluorescence quencher may bind to one another in the cell.

Exemplary combinations of fluorescent dyes and fluorescence quenchers useful in such an approach are set forth in TABLE III.

TABLE III

Exemplary Dye - Quencher Combinations

| Exemplary Dye | Exemplary Quencher |
|---|---|
| D1 | Q1, Q2, Q3, Q4, Q5, Q6, Q8, Q13, Q14, or Q15, or any combination thereof |

TABLE III-continued

Exemplary Dye - Quencher Combinations

| Exemplary Dye | Exemplary Quencher |
|---|---|
| D2 | Q1, Q2, Q3, Q4, Q5, Q6, Q8, Q13, Q14, or Q15, or any combination thereof |
| D3 | Q1, Q2, Q3, Q4, Q5, Q6, Q8, Q13, Q14, or Q15, or any combination thereof |
| D4 | Q1, Q2, Q3, Q4, Q5, Q6, Q8, Q11, Q12, or Q15, or any combination thereof |
| D6 | Q1, Q2, Q3, Q4, Q5, Q6, Q8, Q13, Q14, or Q15, or any combination thereof |
| D7 | Q1, Q2, Q3, Q4, Q5, Q6, Q8, Q13, Q14, or Q15, or any combination thereof |
| D8 | Q2, Q5, Q6, Q11, or Q12, or any combination thereof |
| D20 | Q1, Q2, Q3, Q4, Q5, Q6, Q8, Q13, Q14, or Q15, or any combination thereof |

In another approach, the fluorescent dye and/or quencher can be selected to have binding affinities for a specific cellular component, organelle, or structure, such as a nucleic acid. For example, the fluorescent dye, the fluorescence quencher, or both bind to a nucleic acid in a cell. When the fluorescent dye and quencher are co-bound to the specific target, such as a nucleic acid, the proximity of the dye and quencher are such that a substantially non-fluorescent complex is formed. In either approach, the membrane impermeable quencher is not permitted to enter viable cells via an intact membrane, which prevents the formation of the non-fluorescent complex in viable cells. In one embodiment of the invention, fluorescent dye—fluorescence quencher pairs are chosen such that the fluorescent dye and fluorescence quencher both bind to a specific cellular component such as a nucleic acid. This approach has the advantage that non-specific fluorescent staining is reduced because the fluorescent dye and fluorescence quencher bind to a specific target. As a result, this approach can reduce non-specific fluorescent staining which optimizes the signal to noise ratio when differentiating between viable cells. The nucleic acid binding fluorescent dyes and nucleic acid binding fluorescence quenchers are selected such that there is spectral overlap between the emission spectrum of the fluorescent dye and the absorbance spectrum of the quencher, for example, as shown schematically in FIG. 12A.

Exemplary combinations of fluorescent dyes and fluorescence quenchers that selectively bind a nucleic acid (for example, a DNA or RNA) are set forth in TABLE IV. The feature of spectral overlap between the emission spectrum of the fluorescent dye and the absorbance spectrum of the quencher may be used to guide the selection of a particular fluorescent dye for use with a particular quencher. This approach can be particularly effective when the dye and quencher both bind, for example, selectively bind to a cellular organelle or cell component such as a protein, glycoprotein, carbohydrate, lipid, or nucleic acid.

TABLE IV

Exemplary Nucleic Acid Binding Dye - Nucleic Acid Binding Quencher Combinations

| Exemplary Nucleic Acid Binding Dye | Exemplary Nucleic Acid Binding Quencher |
|---|---|
| D1 | Q16, Q17, or Q18, or any combination thereof |
| D2 | Q16, Q17, or Q18, or any combination thereof |
| D3 | Q16, Q17, or Q18, or any combination thereof |
| D4 | Q16, Q17, or Q19, or any combination thereof |
| D6 | Q16, Q17, or Q18, or any combination thereof |
| D7 | Q16, Q17, or Q18, or any combination thereof |
| D8 | Q16, Q17, or Q19, or any combination thereof |
| D9 | Q16, Q17, or Q19, or any combination thereof |
| D10 | Q16, Q17, or Q19, or any combination thereof |
| D11 | Q16, Q17, or Q19, or any combination thereof |
| D12 | Q16, Q17, or Q19, or any combination thereof |
| D13 | Q16, Q17, or Q19, or any combination thereof |
| D14 | Q16, Q17, or Q19, or any combination thereof |
| D15 | Q16, Q17, or Q19, or any combination thereof |
| D16 | Q16, Q17, or Q18, or any combination thereof |
| D17 | Q16, Q17, or Q18, or any combination thereof |
| D18 | Q16, Q17, or Q19, or any combination thereof |
| D19 | Q16, Q17, Q18, or Q19, or any combination thereof |
| D20 | Q16, Q17, Q18, or Q19, or any combination thereof |
| D21 | Q16, Q17, or Q19, or any combination thereof |
| D22 | Q16, Q17, or Q19, or any combination thereof |
| D23 | Q16, Q17, or Q19, or any combination thereof |
| D24 | Q16, Q17, or Q19, or any combination thereof |
| D25 | Q16, Q17, or Q19, or any combination thereof |
| D26 | Q16, Q17, or Q19, or any combination thereof |
| D27 | Q16, Q17, or Q19, or any combination thereof |
| D28 | Q16, Q17, or Q19, or any combination thereof |
| D29 | Q16, Q17, or Q19, or any combination thereof |
| D30 | Q16, Q17, or Q19, or any combination thereof |
| D31 | Q16, Q17, or Q19, or any combination thereof |
| D32 | Q16, Q17, or Q19, or any combination thereof |
| D33 | Q16, Q17, or Q19, or any combination thereof |
| D34 | Q16, Q17, or Q19, or any combination thereof |
| D35 | Q16, Q17, or Q19, or any combination thereof |
| D36 | Q16, Q17, or Q19, or any combination thereof |
| D37 | Q16, Q17, or Q19, or any combination thereof |
| D38 | Q16, Q17, Q18, or Q19, or any combination thereof |
| D39 | Q16, Q17, Q18, or Q19, or any combination thereof |
| D40 | Q16, Q17, or Q18, or any combination thereof |
| D41 | Q16, Q17, Q18, or Q19, or any combination thereof |
| D42 | Q16, Q17, or Q18, or any combination thereof |
| D43 | Q16, Q17, or Q18, or any combination thereof |
| D44 | Q16, Q17, Q18, or Q19, or any combination thereof |

Figure 12A:
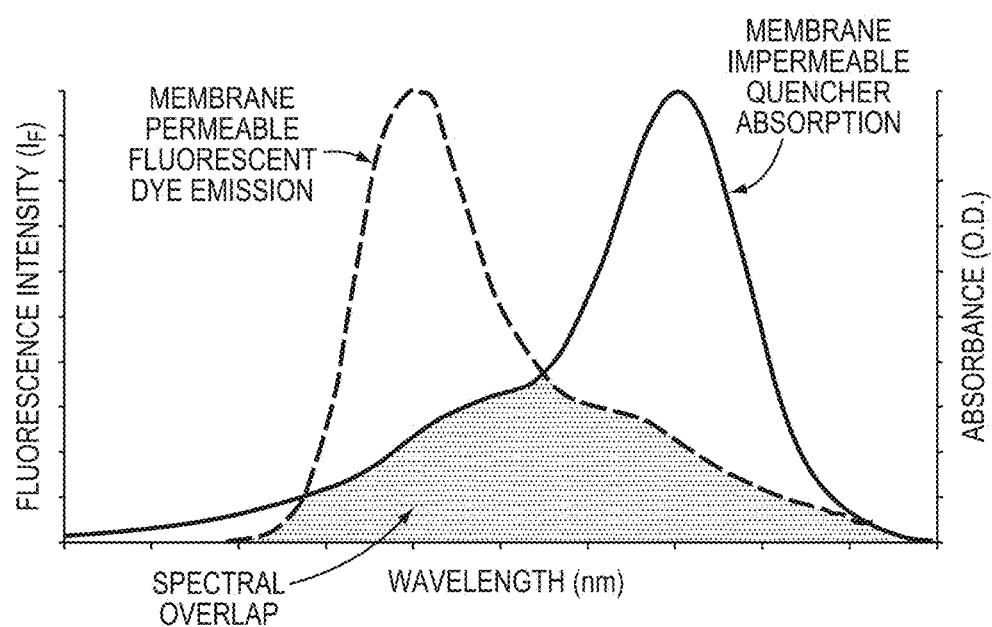
FIG. 12A is a schematic representation of the spectral overlap between the emission of an exemplary fluorescent dye (dashed line, in units of fluorescence intensity ($I_F$)) and the absorption spectrum of an exemplary quencher (solid line, in units of absorbance or optical density (O.D.))

The dye and quencher can be chosen to permit spectral overlap of the emission spectrum of the dye with the absorption spectrum of the quencher, for example, as demonstrated in FIG. 12A to permit the requisite level of quenching to occur. Under these conditions, the fluorescent emission of the fluorescent dye can be suppressed by the quencher via FRET.

The dye and quencher pair can be further characterized according to the extent to which the emission spectrum of the dye overlaps the emission spectrum (if any) of the quencher. Under certain circumstances, it can be desirable to minimize the extent to which emission spectrum of the quencher overlaps with the emission spectrum of the fluorescent dye, particularly that portion of the emission spectrum of the dye that is detected by a detector (e.g., a fluorescence detector) during the cell viability assay. Therefore, in certain embodiments, the quencher is selected such that if the quencher is excited by the light source (excitation light) used to excite the fluorescent dye and such quencher is capable of emitting a photon, then the quencher preferably has one or more of the following properties: (i) the quencher does not emit substantial, or any, electromagnetic radiation within the emission spectrum of the dye (particularly that portion of the emission spectrum of the fluorescent dye that is measured during the cell viability assay, i.e., the portion of the emission spectrum of the fluorescent dye that falls within the bandwidth of detection in the detector (see, wavelength range $\lambda_1$-$\lambda_2$ in FIG. 12B)), and (ii) the quencher has a lower quantum yield than that of the fluorescent dye. As a result, the quencher remains non-fluorescent or substantially non-fluorescent over the range of wavelengths measured during the cell viability assay. Accordingly, when a detection channel in a detector is set to detect the emission signal emanating preferentially from the fluorescent dye, substantially less fluorescence (for example, less than 40%, 30%, 20%, 10% or 5% of the fluorescence) or no fluorescence emanating from the quencher (for example, via autofluorescence or fluorescence created by the excitation source) is detected in the detection channel of the detector (see, wavelength range $\lambda_1$-$\lambda_2$ in FIG. 12B).

Figure 12B:
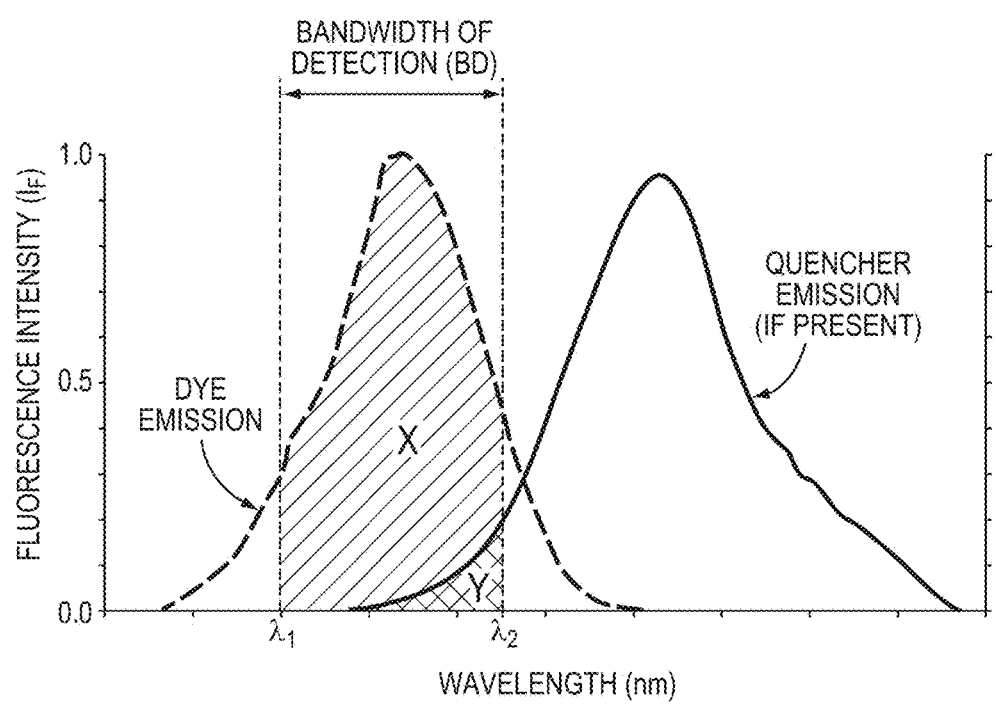
FIGS. 12B-12C are schematic representations showing a partial overlap between the emission spectra of an exemplary fluorescent dye and an exemplary quencher demonstrating two approaches for selecting a dye-quencher pair for use in the cell viability assays discussed herein.

In one approach for selecting an appropriate dye-quencher pair, as shown schematically in FIG. 12B, the emission spectrum of the fluorescent dye (e.g., the membrane permeable dye) is shown by the hatched line and the emission spectrum of the quencher (e.g., the membrane impermeable quencher) is shown by the solid line. A detector with a bandwidth of detection (BD), which is represented, for example, as a wavelength range between wavelength value $\lambda_1$ and wavelength value $\lambda_2$) is capable of detecting a portion of the emission spectrum of the fluorescent dye (area denoted as region X). The area X is the detectable emission of the fluorescent dye. Given the bandwidth of detection, the detector is sometimes also capable of detecting a portion of the emission spectrum of the quencher (area denoted as region Y), assuming that the quencher has its own emission spectrum (certain quenchers are not fluorescent and do not produce an emission spectrum) or the emission spectrum of the quencher overlaps at least a portion of the emission spectrum of the dye. The area Y is the detectable emission of the quencher. In cases where the quencher does produce an emission spectrum, the detectable emission of the quencher (area Y) is no greater than 50% (e.g., no greater than 40%, no greater than 30%, no greater than 20%, no greater than 10%, or no greater than 5%) of the detectable emission of the dye (area X) so as to provide the appropriate signal-to-noise ratio for the detection of viable cells. In a preferred embodiment, the detectable emission of the quencher (area Y) is no greater than 30% of the detectable emission of the dye (area X).

This approach can be performed by taking the fluorescence emission spectra of the dye and quencher and then identifying the portions (areas under the curve) under each spectra that fall within the bandwidth of the proposed detector (see FIG. 12B). The ratio of these values is then used to determine that the detectable emission of the quencher is no greater than 50% of the detectable emission of the dye. The choice of the dye-quencher pair depends upon the choice of the appropriate bandwidth of detection in the detector, the fluorescent dye and the quencher.

Figure 12C:
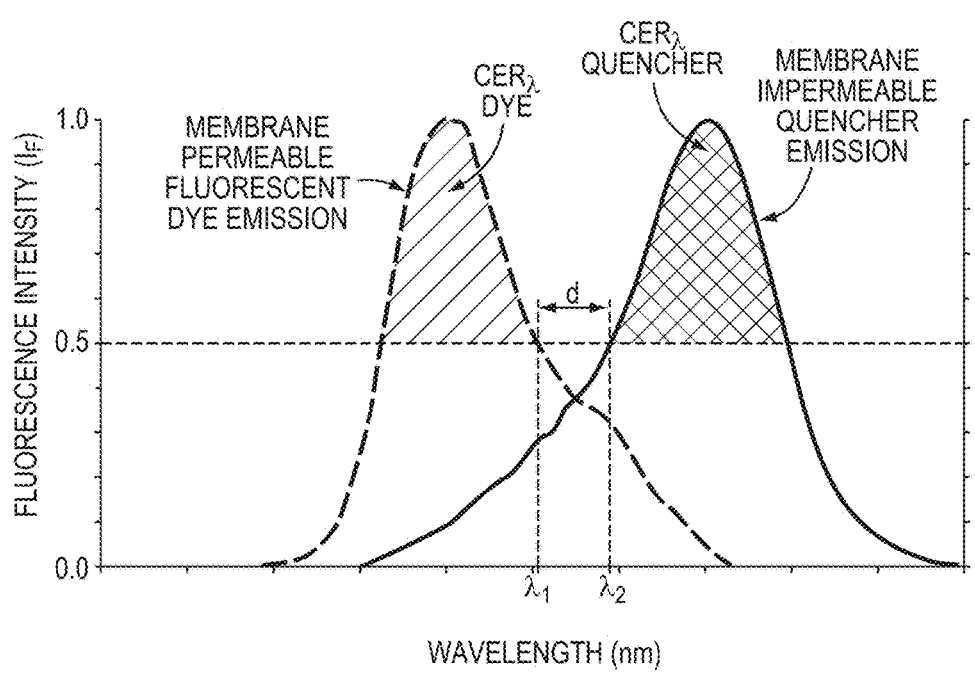

An alternative approach can be used for selecting an appropriate dye—quencher pair. For example, in another embodiment, the separation of the emission spectra of the fluorescent dye from the emission spectra (if present) of the quencher can be characterized according to non-overlap of the critical emission wavelength range of the fluorescent dye and the critical emission wavelength range of the quencher. The separation of the critical emission wavelength range of the fluorescent dye from the critical emission wavelength range of the quencher is illustrated in FIG. 12C. The term "critical emission wavelength range(s)" or CER$_\lambda$ means the wavelength range(s) of the emission profile over which a fluorophore has an emission intensity that is at least 40%, 50%, 60%, 70%, 80%, or 90% of the maximum emission intensity at the $\lambda_{max}$ of the emission spectrum of the fluorophore. Thus, the critical emission wavelength range of the fluorescent dye is the wavelength range of the emission profile of the fluorescent dye over which the dye has an emission intensity that is at least 40%, 50%, 60%, 70%, 80%, or 90% of the maximum emission intensity at the $\lambda_{max}$ of the emission spectrum of the fluorescent dye. The critical emission wavelength range of the quencher is the wavelength range of the emission profile (if any) of the quencher over which the quencher has an emission intensity that is at least 40%, 50%, 60%, 70%, 80%, or 90% of the maximum emission intensity at the $\lambda_{max}$ of emission spectrum of the quencher.

To illustrate further, the emission intensity of an exemplary fluorescent dye and emission intensity of an exemplary quencher are illustrated in FIG. 12C. The critical emission wavelength range of the fluorescent dye is labeled CER$_\lambda$ dye, and corresponds to those wavelengths where the emission intensity of the dye is at least 50% of the maximum emission intensity of the dye at its $\lambda_{max}$. The critical emission wavelength range of the quencher is labeled CER$_\lambda$ quencher, and corresponds to those wavelengths where the emission intensity of the quencher is at least 50% of the maximum emission intensity of the quencher at its $\lambda_{max}$. As depicted in FIG. 12C, there is no overlap of the critical emission wavelength range of the fluorescent dye with the critical emission wavelength range of the quencher. The difference between the wavelengths (i.e., $\lambda_1$-$\lambda_2$) is denoted by the term "d" in FIG. 12C, which preferably is at least 5 nm (or at least 10 nm, 20 nm, 30 nm, 40 nm, 50 nm, 60 nm, 70 nm, 80 nm, 90 nm or 100 nm).

Depending on the emission spectra of the fluorescent dye and the quencher, it is understood that wavelengths that exceed the threshold intensity (e.g., 50% of the maximum emission intensity of the dye at its $\lambda_{max}$) may not be continuous. For example, the emission spectra of the dye and/or quencher may contain two or more wavelength ranges that exceed the threshold intensity (e.g., 50% of the maximum emission intensity of the dye or the quencher at its respective $\lambda_{max}$). Preferably there is little or no overlap between the critical emission wavelength range(s) of the fluorescent dye and the critical emission wavelength range(s) of the quencher. Using these criteria, it is possible to choose dye-quencher combinations useful in the cell viability assays described herein.

The concentrations of a particular membrane permeable fluorescent dye and membrane impermeable fluorescent quencher are selected to (i) provide sufficient fluorescence intensity from the fluorescent dye in viable cells, (ii) substantially quench fluorescence of the fluorescent dye in non-viable cells, and (iii) to minimize any toxicity of the dye and/or quencher. In certain embodiments, the membrane permeable fluorescent dye is used at a concentration in the range of from about 0.1 µM to about 50 µM, from about 0.5 µM to about 30 µM, or from about 1 µM to about 10 µM, when applied to cells. In certain embodiments, the amount of membrane impermeable fluorescent quencher applied to cells is about the same molar concentration as the fluorescent dye or greater. In certain embodiments, the amount of membrane impermeable fluorescent quencher applied to cells is at a concentration of 0.1 µM to about 200 mM, from about 0.5 µM to about 100 mM, from about 0.5 µM to about 1 mM, from about 0.5 µM to about 500 µM, from about 1 µM to about 500 µM, or from about 1 µM to about 100 µM, when applied to cells. In other embodiments, the quencher is provided at a molar excess of, for example, 2-fold, 3-fold, 4-fold, 5-fold, 6-fold, 7-fold, 8-fold, 9-fold, 10-fold, 20-fold, 40-fold, 60-fold, 80-fold, 100-fold, 200-fold, 300-fold, 400-fold, 500-fold, 1000-fold, or 2,000-fold, 5,000-fold, 10,000-fold, 20,000-fold, 50,000-fold or 100,000-fold, relative to the concentration of the fluorescent dye. The amount of the quencher should be chosen so that the quencher is non-toxic or is substantially non-toxic to the cells being detected in a given sample. In certain embodiments, the amount of membrane impermeable fluorescent quencher applied to cells is in the range of about a 5-fold molar excess to about a 20-fold molar excess or about a 5-fold molar excess to about a 10-fold molar excess, relative to the amount of membrane permeable fluorescent dye applied to cells.

Depending upon the cells being detected and desired sensitivity, it is possible to expose the cells to a plurality of different fluorescent dyes and/or a plurality of different fluorescence quenchers. Furthermore, depending upon the dyes and quenchers to the used, and the cells to be detected, the cells can be exposed to the fluorescent dye and then exposed to fluorescence quencher. Alternatively, the cells can be exposed to the fluorescent dye and the fluorescence quencher at the same time. In certain methods, a washing step using, for example, a physiologically acceptable salt and/or buffer solution can be used to remove residual dye or quencher before detection. In certain methods, a subsequent washing step is not necessary and the washing step if employed could even be undesirable if the fluorescent dye is removed or extracted from the viable cells, for example, via diffusion out of the cells during the washing step.

The detection method can be performed on single cells, clusters of cells or colonies of cells. Under certain circumstances, for example, to increase the sensitivity of the assay, it may be desirable to culture the cells under conditions that permit cell proliferation prior to and/or during and/or after exposing the cells to the fluorescent dye and the fluorescence quencher. The culture conditions, including, the choice of the growth media, the temperature, the duration of the culture, can be selected to permit at least one of cells in the sample to have one or more cell divisions.

For example, depending upon the sensitivity required, the cells, once captured on the membrane, can be contacted with growth media and/or spore germination initiators and then permitted to proliferate for one or more doubling times to increase the number of cells at a particular locus on the membrane. In one embodiment, the cells are captured on membrane 202, a solution containing the fluorescent dye and the fluorescence quencher and growth medium (e.g., Nutrient Broth T7 105 from PML Microbiologicals, Wisonville, Oreg.) are poured into the cup assembly and pulled through membrane 202 via vacuum suction. The lid 588 is then placed upon base 554 (see FIG. 10C), and the resulting unit can be placed in an incubator at a preselected temperature (e.g., 37° C.) for a desired length of time (e.g., from 15 minutes to 8 hours, or from 30 minutes to 4 hours) depending upon the doubling time of the organisms. During this time, the membrane 202 remains moist in view of the growth media and stain present within solid support 558. This approach also provides more time for the fluorescent dye and quencher to permeate and stain the cells. After incubation, the base 554 can then be transferred to and placed into stage 802 for insertion into the detection device.

In certain embodiments, the fluorescent dye and/or the fluorescence quencher, bind to a nucleic acid within the cell. In other embodiments, the fluorescent dye and the fluorescence quencher bind to one another in the cell.

In certain embodiments, the beam of light used to excite the fluorescent dye or fluorescent dyes has a wavelength in the range of from about to 350 nm to about 1000 nm, from about 350 nm to about 900 nm, from about 350 nm to about 800 nm, from about 350 nm to about 700 nm, or from about 350 nm to about 600 nm. For example, the wavelength of excitation light is at least in one range from about 350 nm to about 500 nm, from about 350 nm to about 500 nm, from about 350 nm to about 600 nm, from about 400 nm to about 550 nm, from about 400 nm to about 600 nm, from about 400 nm to about 650 nm, from about 450 nm to about 600 nm, from about 450 nm to about 650 nm, from about 450 nm to about 700 nm, from about 500 nm to about 650 nm, from about 500 nm to about 700 nm, from about 500 nm to about 750 nm, from about 550 nm to about 700 nm, from about 550 nm to about 750 nm, from about 550 nm to about 800 nm, from about 600 nm to about 750 nm, from about 600 nm to about 800 nm, from about 600 nm to about 850 nm, from about 650 nm to about 800 nm, from about 650 nm to about 850 nm, from about 650 nm to about 900 nm, from about 700 nm to about 850 nm, from about 700 nm to about 900 nm, from about 700 nm to about 950 nm, from about 750 to about 900 nm, from about 750 to about 950 nm or from about 750 to about 1000 nm. Certain ranges include from about 350 nm to about 600 nm and from out 600 nm to about 750 nm.

The fluorescent emission can be detected within a range of from about 350 nm to about 1000 nm, from about 350 nm to about 900 nm, from about 350 nm to about 800 nm, from about 350 nm to about 700 nm, or from about 350 nm to about 600 nm. For example, the fluorescent emission can be detected within a range from about 350 nm to 550 nm, from about 450 nm to about 650 nm, from about 550 nm to about 750 nm, from about 650 nm to about 850 nm, or from about 750 nm to about 950 nm, from about 350 nm to about 450 nm, from about 450 nm to about 550 nm, from about 550 nm to about 650 nm, from about 650 nm to about 750 nm, from about 750 nm to about 850 nm, from about 850 nm to about 950 nm, from about 350 nm to about 400 nm, from about 400 nm to about 450 nm, from about 450 nm to about 500 nm, from about 500 nm to about 550 nm, from about 550 nm to about 600 nm, from about 600 nm to about 650 nm, from about 650 nm to 700 nm, from about 700 nm to about 750 nm, from about 750 nm to about 800 nm, from about 800 nm to about 850 nm, from about 850 nm to about 900 nm, from about 900 nm to about 950 nm, or from about 950 nm to about 1000 nm. In certain embodiments, the emitted light is detected in the range from about 660 nm to about 690 nm, from about 690 nm to about 720 nm, and/or from about 720 nm to about 850 nm.

In each of the foregoing, the method can further comprise exposing the cells to a second, different membrane permeable fluorescent dye that labels viable cells, non-viable cells or a combination of viable and non-viable cells.

(IV) Cell Detection

Once the cell capture system has been used to capture cells originally present in the fluid sample, the membrane or the membrane assembly can be inserted into a membrane holder (e.g., holder 802) for insertion into a suitable detection system. Exemplary detection systems are described, for example, in International Patent Application No. PCT/IB2010/054965, filed Nov. 3, 2010, U.S. patent application Ser. No. 13/034,402, filed Feb. 24, 2011, International Patent Application No. PCT/IB2010/054966, filed Nov. 3, 2010, U.S. patent application Ser. No. 13/034,380, filed Feb. 24, 2011, International Patent Application No. PCT/IB2010/054967, filed Nov. 3, 2010, and U.S. patent application Ser.

No. 13/034,515, filed Feb. 24, 2011. In the foregoing detection systems, a membrane is rotated while a beam of excitation light is directed onto the surface of the membrane. The emitted light is detected with at least one optical detector.

In order to facilitate rotation of the permeable membrane, the membrane can be disposed in a membrane holder. In one embodiment, for example, in a membrane assembly that comprises a mask and optional spokes, the membrane assembly may be inserted into a membrane holder that can be placed within sample assembly 120 of FIG. 1A. In particular, the membrane assembly may be placed upon the rotating platform 130.

Figure 13A:
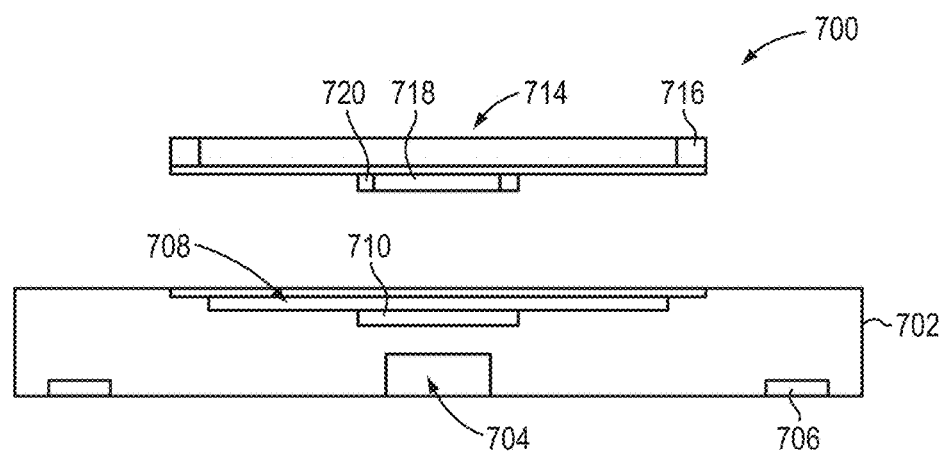
FIG. 13A is a schematic exploded cross-sectional side view of an exemplary membrane holder for use with the system of FIG. 1A.
Figure 13B:
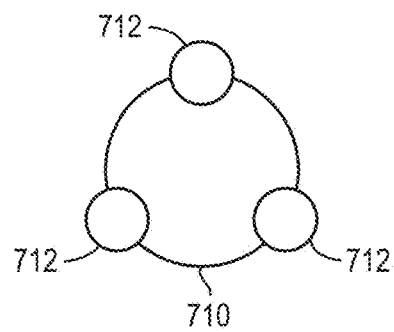
FIG. 13B is a schematic of a configuration of magnets for use with the membrane holder (stage) of FIG. 13A.

FIGS. 13A and 13B show an exemplary membrane holder that can be used in such a detection system. Membrane holder 700 comprises a container 702 (e.g., a metallic container made of aluminum) defining a central cylindrical recess 704 and an offset drive aperture or notch 706. The container 702 may be disposed upon a rotatable shaft such that the shaft is received within, coupled to, or otherwise engaged with the recess 704. The shaft may form a disk to support the holder 700 and can include a protrusion, such as a driver pin that couples with the drive notch 706. As a result, rotation of the disk about its axis of rotation correspondingly positively rotates the membrane holder 700 without slippage.

The container 702 also defines a chamber 708 to receive a membrane and any components for holding the membrane generally flat. These components include a holder having spokes (described with reference to FIGS. 2A and 2B), the masks (described with reference to FIGS. 3A and 3B), and/or or the porous supporting member (described with reference to FIGS. 4A-4B). Under the chamber 708, a plurality of magnets 712 can be disposed within the container 702. An exemplary magnet configuration 710 is depicted in FIG. 13B. The configuration 710 includes three magnets 712 located approximately in a circular pattern having a center at or near the axis of rotation of the container 702. The plane of the circle of magnets 712 is substantially parallel to the surface of the chamber 708. The container 702 further comprises a window 714 such as a glass, polycarbonate or PERSPEX® window enclosed in a magnetic ring 716. In certain embodiments, the magnets 712 are disk magnets and are used to maintain the elements in the chamber 708 during rotation (e.g., by attraction of the magnetic ring 716). It should be understood that the configuration 710 is for illustrative purposes only, and that other configurations, such as those having fewer or more than three magnets, may incorporate patterns other than a circular pattern, as well as other retention schemes, and are considered within the scope of the present invention.

The window 714 protects the underlying cell retaining membrane, as well as the cells, and can maintain the sterility of the membrane if is to be subsequently removed and incubated under conditions (e.g., temperature, moisture, and nutrition) to facilitate growth of the viable cells. The magnetic ring 716 can have an extension 718 forming a magnetic stainless steel ring 720. The center of the extension 718 is located at or near the axis of rotation of container 702. Accordingly, when the window 714 is disposed over a membrane assembly received in the chamber 708, the ring 720 is substantially disposed directly over the configuration 710 of magnets 712. As the magnetic ring 720, and hence, the window 714 are moved toward the magnets 712, the membrane received in the chamber 708 is generally held in place as the container 702 rotates about its axis of rotation. The extension 718 may also apply downward pressure on the membrane (e.g., via a central mask, etc.), helping preserve the flatness of the membrane received in the chamber 708.

Figure 13C:
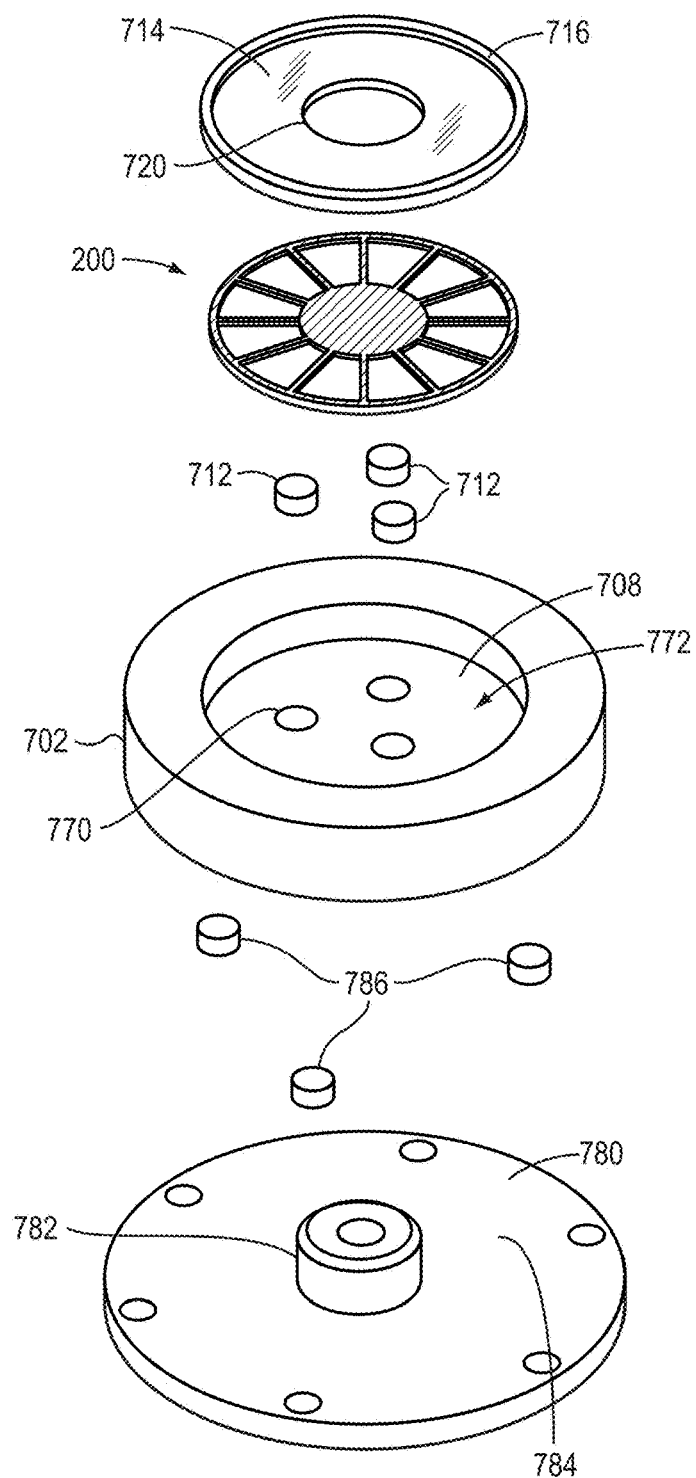
FIG. 13C is a schematic exploded perspective view of the membrane holder (stage) of FIG. 13A with a membrane assembly and chuck.
Figure 13D:
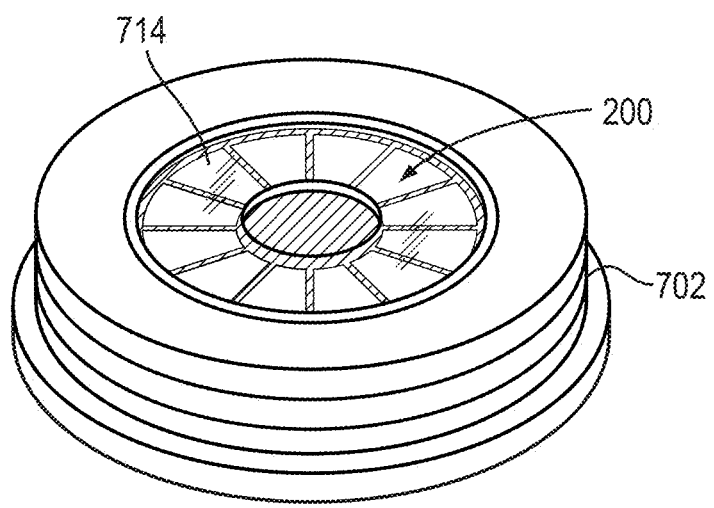
FIG. 13D is a schematic perspective view of the membrane holder, membrane assembly, and chuck of FIG. 13C in an assembled configuration.

FIG. 13C depicts a membrane holder assembly for use in an optical detection system assembly disposed within the container (also called a cartridge holder) 702. Other membrane assemblies, including those described herein, may also be received in the container/holder 702. The window 714 is disposed over the membrane assembly 200. The magnets 712 are disposed in recesses 770 in a bottom surface 772 of the container 702. As described above, when the membrane assembly 200 is received in the chamber 708, the magnets 712 pull ring 720 of the window 714 toward the surface 772 of the container/cartridge holder 702, thereby holding the membrane assembly 200 in place, as depicted in FIG. 13D.

The container/holder 702 can then be placed on a disk or chuck 780 that has a shaft 782 and a driver mechanism 784 that engages a recess defined by the base of the container/holder 702. The shaft 782 engages with the notch 704. The disk/chuck 780 fits on a motor shaft of the detection system. Rotation of the motor shaft drives the rotation of the membrane assembly 200. The shaft 782 and the driver 784 prevent the container/holder 702 from slipping or sliding on the surface of the disk 780. In addition, the magnets 786 align the container/cartridge holder 702 with a predetermined position on the surface of the disk 780, thereby facilitating registration of the initial orientation of the membrane assembly 200. Such registration can be beneficial when mapping the location of any fluorescence events (e.g., light emitted by viable cells, non-viable cells or particles).

Many other embodiments of a membrane holder are contemplated. For example, a membrane holder with three magnets disposed in a rim of a container and a window having an integral or separate magnetic rim that has three notches and three legs has been contemplated. In such an embodiment, the rim of the membrane holder may have three stops. When the magnetic rim is disposed over the container, the legs can slide along the outer surface of the rim until the legs are in contact with the stops. The magnets are disposed in the rim and the notches are located in the magnetic rim, such that when the legs are in contact with the stoppers, each of the notches is positioned directly over one of the magnets. In this position, the magnetic rim and the window can be readily separated from the membrane holder, and a membrane assembly can be received in or removed from a chamber of the container. Thereafter, the window can be replaced. The window can be rotated such that the notches are not aligned with the magnets, and as such, the magnetic rim and the window are substantially held in place by the magnets. Consequently, the membrane assembly received in the chamber is also substantially held in place.

Figure 15A:
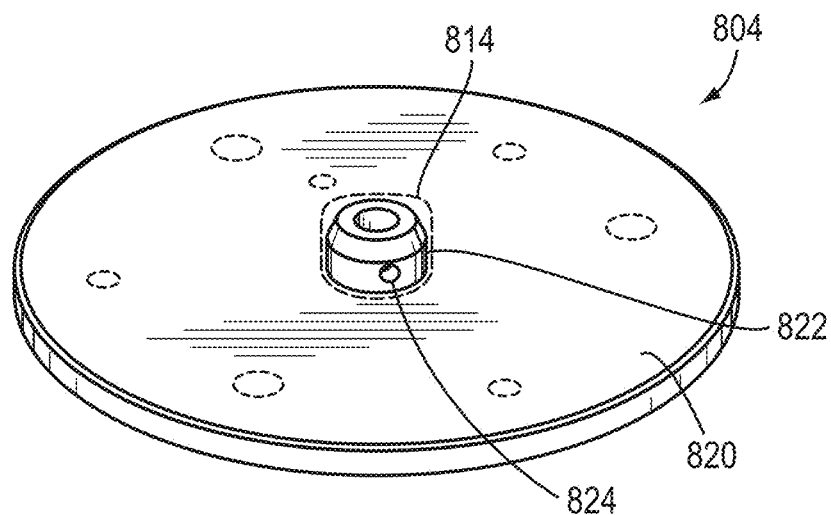
FIGS. 15A-15D are schematic perspective, top, bottom, and side views, respectively, of an exemplary chuck.
Figure 15B:
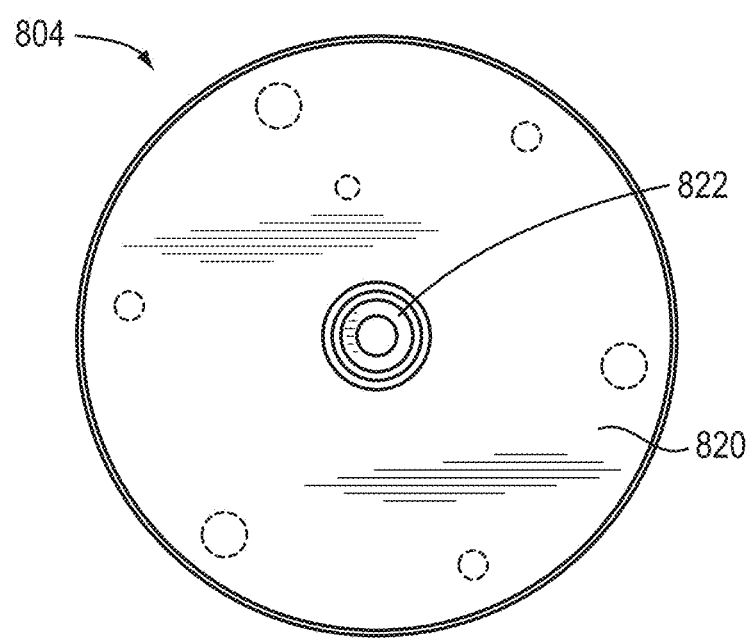
Figure 15C:
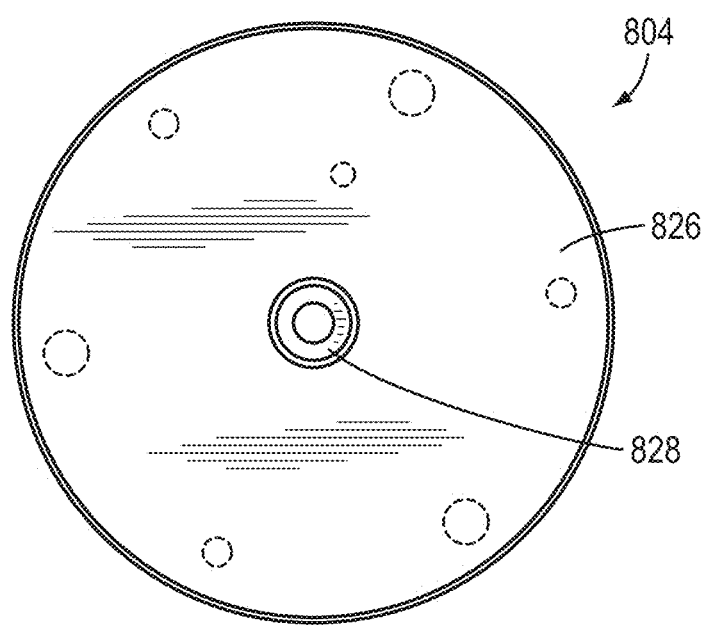
Figure 15D:
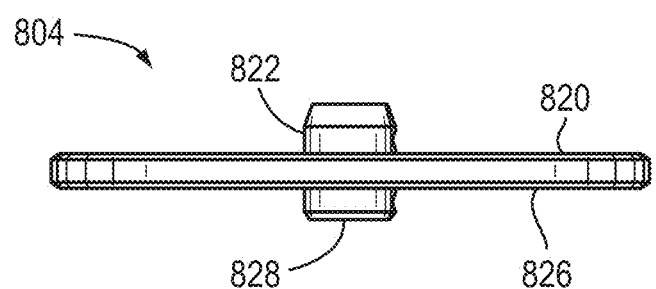

In order to minimize the number of manipulation steps for transferring the porous membrane assembly 200 into the membrane holder, which can increase the risk of contaminating the membrane assembly 200, it is contemplated that the membrane holder can be adapted to engage the membrane assembly together with the base of a cup (e.g., the base 554). FIGS. 14A-14C depict the stage 802 adapted to receive the base 554. The stage 802 may have multiple recesses 810, each adapted to receive a separate base 554. Walls 812 of the recesses are tapered to receive the similar tapered lower portion 576 of the base 554, helping ensure a secure fit for stability during rotation. The stage 802 is depicted in a substantially circular form, but may be any shape. The stage 802 may be sized to fit within the enclosure 110, either permanently or temporarily. A lower surface of the stage 810 includes a mating recess 814 for attachment to the chuck 804 (depicted in FIGS. 15A-15D). The chuck 804 provides a base on which the stage 802 sits, and provides the means for rotating the stage 802. The chuck 804 can be permanently installed in the enclosure 110, or may be removable. In an embodiment where the stage 802 and the chuck 804 are already disposed within the enclosure 110, only the base 554 with the saturated membrane 202 would need to be transferred into the enclosure 110 to begin operation, thus minimizing the number of handling steps. The chuck 804 has an upper surface 820 that can be sized to support a large portion of the stage 802 for increased stability during operation. A protrusion 822 on the top surface 820 is adapted to mate with the mating recess 814 of the stage 802, which is depicted in broken outline in FIG. 15A. The protrusion 822 may have an aperture 824 for receiving a fastener (e.g., a set screw) for further securing the stage 802 to the chuck 804. A bottom surface 826 of the chuck 804 has a protrusion 828 for mating with a drive for rotating the chuck 804.

As discussed above, for accurate detection and/or estimation of cells and/or particles, the porous membrane 202 should be flat, substantially horizontal, and at or about a predetermined distance from the source of the light impinged thereupon. Optionally, the membrane 202 is located at or near the focal length of the detection system 170. The thickness of the base 554 and flatness of the surface of the base 554 can affect the height and plane of the membrane 202.

Figure 16A:
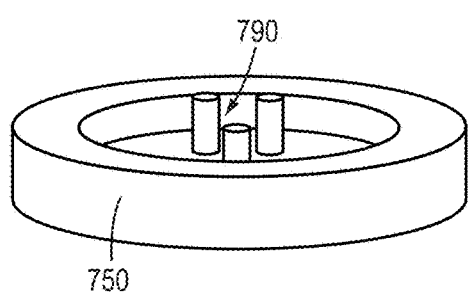
FIG. 16A is a schematic perspective view of an exemplary membrane holder (stage) for receiving a base.
Figure 16B:
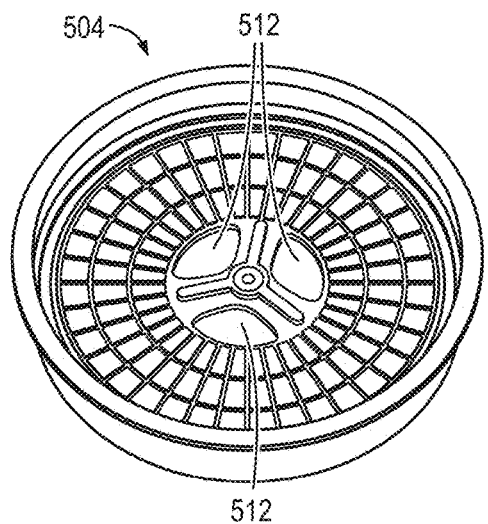
FIG. 16B is a schematic perspective view of an exemplary base for use with the membrane holder of FIG. 16A.
Figure 16C:
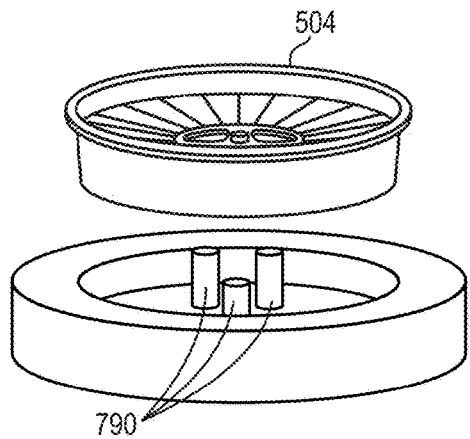
FIG. 16C is a schematic perspective view of the exemplary membrane holder of FIG. 16A and the base of FIG. 16B in an unassembled configuration.
Figure 16D:
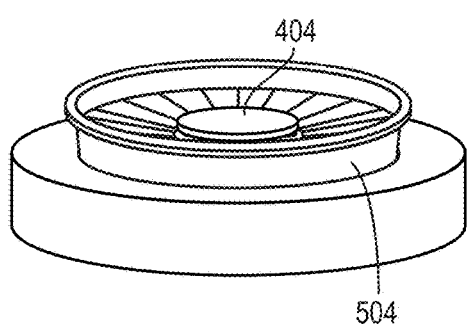
FIG. 16D is a schematic perspective view of the exemplary membrane holder of FIG. 16A and the base of FIG. 16B in an assembled configuration showing posts extending from the membrane holder and passing through operatives defined by the base.

The distance and planarity may be maintained using a variety of different approaches. In one embodiment, as depicted in FIGS. 16A-16D, when using an assembly for use in the system of FIG. 1, depicted posts 790 pass through the openings 512 in the base 504, and can contact the bottom surface of the porous member 404 disposed within the base 504. The porous member 404 is lifted from base 504 as shown in FIG. 16D. Both the top and bottom surfaces of the porous member 404 can be very flat and parallel, and disposed within the focal plane of the detection system 170. The heights of the posts 790 are precisely machined to define a horizontal plane at a predetermined height in the detection system 170, such that the posts 790 directly support the membrane support member 404, free from the base 504. Accordingly, by controlling precisely solely the thickness and flatness of the support members 404, the exposed surfaces of the membranes 202 can be reliably and repeatably positioned almost exactly at the focal plane of the detection system 170. Variability in the dimensions of the bases 504 thereby do not affect the accuracy of the detection system 170. In other words, the membrane 202 disposed upon the top surface of the porous member 404 can be located substantially at the focal plane of the detection system 170 on a consistent basis. While described with respect to the base 504, the base 554 has similar openings 586 that may be used in conjunction with the posts 790.

In another embodiment, posts are disposed upon and extend from the bottom surface of the container/holder. The base of a cup is disposed above the posts so that the posts pass through the corresponding apertures formed in the base. The height of the posts can be adjusted so that the membrane is in a substantially horizontal plane and at a certain height within a specified tolerance from the bottom surface of the container/holder. Thus, the membrane can be at or near the focal plane of the detection system.

The systems and methods described herein can be used to detect the presence and/or quantity of viable cells (for example, prokaryotic cells or eukaryotic cells) in a liquid sample. The method can be used in combination with a cell capture system and/or an optical detection system for detecting the presence of viable cells in a cell sample. The method can be used in a method to measure the bioburden (e.g., the number and/or percentage and/or fraction of viable cells (for example, viable microorganisms, for example, bacteria, yeast, and fungi)) of a particular sample of interest.

The invention provides a method of determining the presence and/or amount of cells in a liquid sample. The method comprises the steps of: (a) capturing cells, for example, viable cells, present in the sample on the any one of the cell capture system and/or the cell capture cup disclosed hereinabove; and (b) determining the presence or amount of cells captured in step (a). The method can further comprise the step of labeling, for example, selectively labeling, the captured cells with a detectable moiety, for example, a fluorescent label (fluorescent moiety). The determining step can utilize an optical detector, for example, a fluorescence detector. The invention also provides a method of detecting presence of viable cells, and/or measuring the viability of cells, in a liquid sample. The method comprises the steps of: (a) capturing cells present in the sample and/or the cell capture cup disclosed above; (b) selectively labeling captured viable cells; and detecting the presence of cells labeled in step (b) and/or measuring the viability of cells labeled in step (b). The cells can be labeled using at least one of a viability stain and a viability staining system, each of which can comprise a fluorescent moiety. The labeled viable cells can be detected with an optical detector, for example, a fluorescence detector.

The invention also provides a method of detecting the presence and/or quantity of viable cells in a liquid sample. The method comprises (a) labeling with a fluorescent label any viable cells retained by at least a portion of a substantially planar porous membrane after passing the liquid sample through the portion of the substantially planar porous membrane with a fluorescent label; (b) scanning the portion of the porous membrane by rotating the porous membrane relative to a detection system comprising (i) a light source emitting a beam of light of a wavelength adapted to excite the fluorescent label to produce an emission event, and (ii) at least one detector capable of detecting the emission event, thereby to interrogate a plurality of regions of the planar porous membrane and to detect emission events produced by excitation of fluorescent label associated with any viable cells; and (c) determining the presence and/or quantity of viable cells captured by the membrane based upon the emission events detected in step (b).

The scanning step can comprise tracing at least one of a nested circular pattern and a spiral pattern on the porous membrane with the beam of light. It is understood that during the scanning step, the porous membrane may move (for example, via linear translation) while the detection system remains static. Alternatively, the detection system may move (for example, via linear translation) while the porous membrane rotates about a single point (i.e., the porous membrane rotates about a single rotational axis). Alternatively, it is possible that both the porous membrane and the detection may move and that their relative positions are measured with respect to one another.

During operation, the membrane holder 700 and the membrane are rotated at a constant speed, and the speed can range from about 1 rpm to about 5,000 rpm, from about 1 rpm to about 1,000 rpm, from about 1 rpm to about 750 rpm, from about 1 rpm to about 500 rpm, from about 1 rpm to about 400 rpm, from about 1 rpm to about 300 rpm, from about 1 rpm to about 200 rpm, from about 1 rpm to about 100 rpm, from about 1 rpm to about 50 rpm, 20 rpm to about 5,000 rpm, from about 20 rpm to about 1,000 rpm, from about 20 rpm to about 750 rpm, from about 20 rpm to about 500 rpm, from about 20 rpm to about 400 rpm, from about 20 rpm to about 300 rpm, from about 20 rpm to about 200 rpm, from about 20 rpm to about 100 rpm, from about 20 rpm to about 50 rpm, 30 rpm to about 5,000 rpm, from about 30 rpm to about 1,000 rpm, from about 30 rpm to about 750 rpm, from about 30 rpm to about 500 rpm, from about 30 rpm to about 400 rpm, from about 30 rpm to about 300 rpm, from about 30 rpm to about 200 rpm, from about 30 rpm to about 100 rpm, or from about 30 rpm to about 50 rpm.

Similarly, the rotating membrane may be translated relative to the detection system at a constant linear velocity, which may or may not be dependent on the rotational speed. The linear velocity can vary from about 0.01 mm/min to about 20 mm/min, from about 0.01 mm/min to about 10 mm/min, from about 0.01 mm/min to about 5 mm/min, from about 0.01 mm/min to about 2 mm/min, from about 0.01 mm/min to about 1 mm/min, from about 0.01 mm/min to about 0.5 mm/min, from about 0.06 mm/min to about 20 mm/min, from about 0.06 mm/min to about 10 mm/min, from about 0.06 mm/min to about 5 mm/min, from about 0.06 mm/min to about 2 mm/min, from about 0.06 mm/min to about 1 mm/min, from about 0.06 mm/min to about 0.5 mm/min, from about 0.1 mm/min to about 20 mm/min, from about 0.1 mm/min to about 10 mm/min, from about 0.1 mm/min to about 5 mm/min, from about 0.1 mm/min to about 2 mm/min, from about 0.1 mm/min to about 1 mm/min, from about 0.1 mm/min to about 0.5 mm/min, from about 0.6 mm/min to about 20 mm/min, from about 0 6 mm/min to about 10 mm/min, from about 0.6 mm/min to about 5 mm/min, from about 0 6 mm/min to about 2 mm/min, or from about 0.6 mm/min to about 1 mm/min.

Figure 17A:
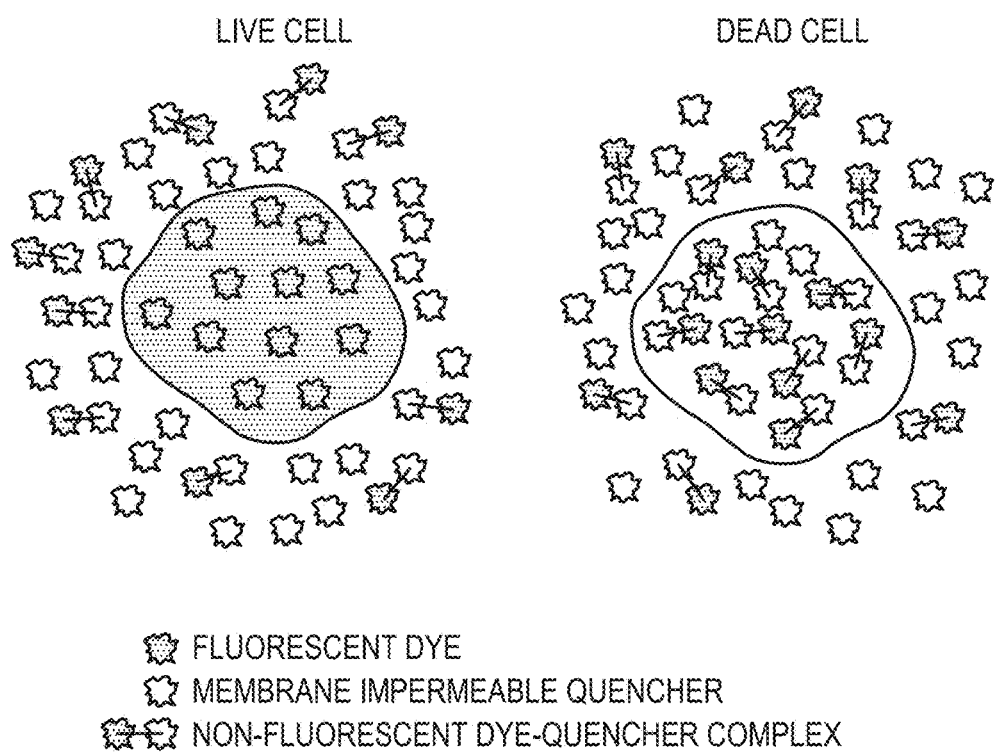
FIG. 17A is a schematic representation of viable (live) and non-viable (dead) cells following staining with a membrane permeable fluorescent dye that permeates both viable and non-viable cells and a membrane impermeable quencher that selectively permeates non-viable cells.

FIG. 17A is a schematic representation of cells that have been stained with the viability staining procedure described herein. The cells are exposed to a membrane permeable fluorescent dye that permeates both viable (live) and non-viable (dead) cells. When exposed to the membrane impermeable quencher, the quencher only permeates and resides within the non-viable cells to create a non-fluorescent dye-quencher complex where the fluorescent dye in the non-viable cells is quenched and does not create a substantial emission event that can be detected by the detection system. In contrast, the fluorescent dye in the viable cells are not quenched and can create a substantial emission event that can be detected by the detection system. In this figure, the fluorescent dye and the fluorescence quencher bind to each other to form a complex. In this procedure, the viable cells create fluorescence events that are significantly larger (brighter) than those created by the dead cells.

Figure 17B:
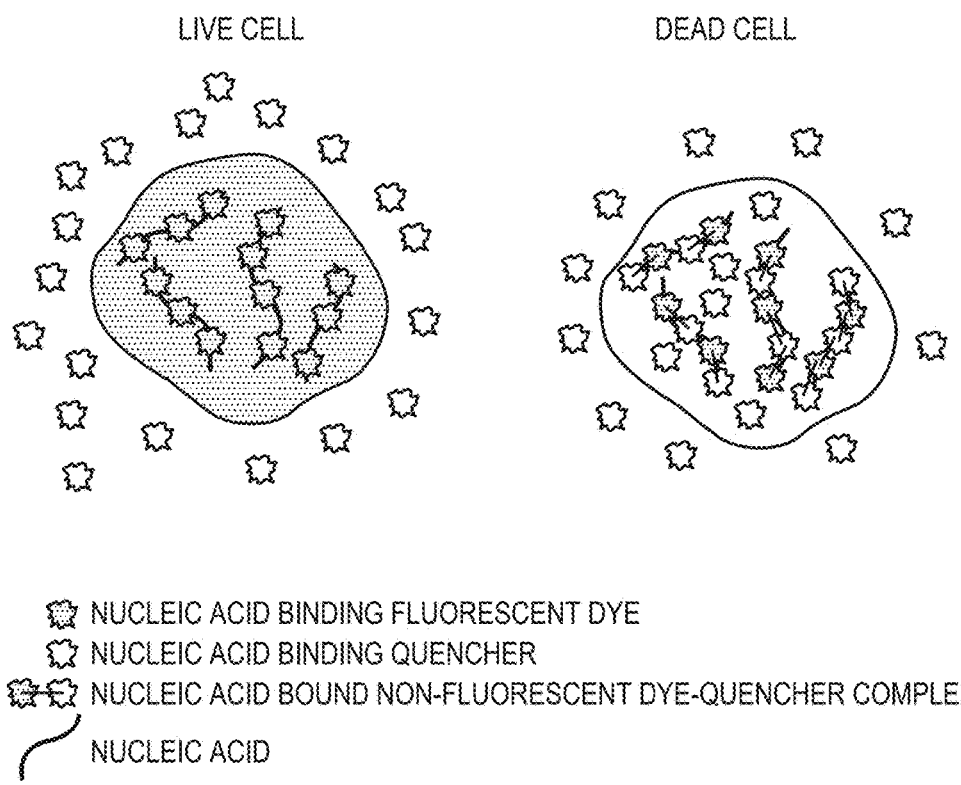
FIG. 17B is a schematic representation of viable (live) and non-viable (dead) cells following staining with a membrane permeable nucleic acid binding fluorescent dye that permeates both viable and non-viable cells and a membrane impermeable nucleic acid binding quencher that selectively permeates non-viable cells.

FIG. 17B is a schematic representation of cells that have been stained with the viability staining procedure as described for FIG. 17A. However, in this embodiment, both the fluorescent dye and the fluorescence quencher bind to a nucleic acid within the cell, for example, DNA or RNA (e.g., mRNA or tRNA). The membrane permeable fluorescent dye permeates both viable (live) and non-viable (dead) cells, and the membrane impermeable quencher only permeates and resides within the non-viable cells to create a nucleic acid bound non-fluorescent dye-quencher complex. As a result, the fluorescent dye within the non-viable cells is quenched and does not create a substantial emission event that can be detected by the detection system. In contrast, the fluorescent dye in the viable cells is not quenched and can create a substantial emission event that can be detected by the detection system. As a result, the viable cells create fluorescence events that are significantly larger (brighter) than those created by the dead cells.

Figure 18:
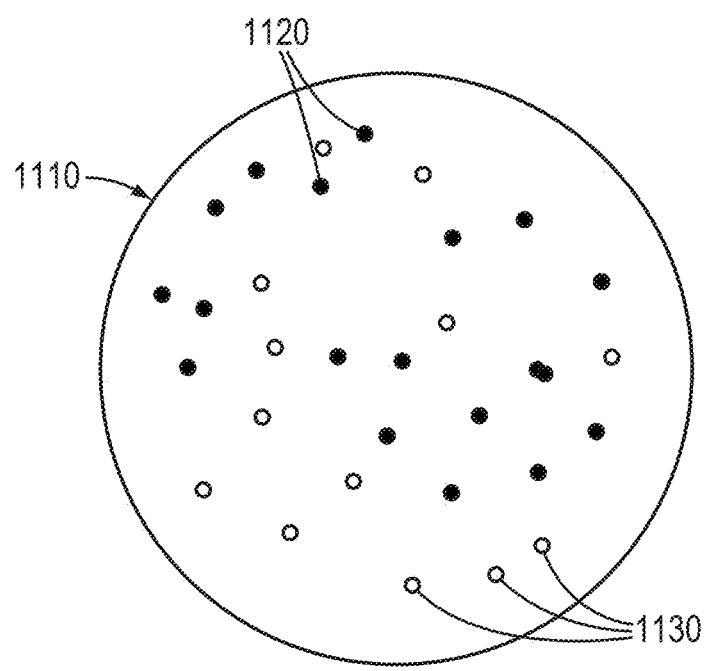
FIG. 18 is a schematic representation of a region of a permeable membrane showing viable and non-viable cells stained with an exemplary viability staining system shown in FIG. 17A or 17B.

An illustrative view of cells stained by the methods described herein (e.g., as presented schematically in FIGS. 17A and 17B) is shown in FIG. 18. A region 1110 being interrogated by the detection system contains bright viable cells 1120 and dark non-viable cells 1130. The number, magnitude and location of the fluorescent events can be captured digitally and represented in a form that permits the operator to quantify (for example to determine the number of, percentage of) viable cells in a sample and/or otherwise to determine the bioburden of a particular sample.

As noted above, in certain embodiments, the cell capture system, the staining method, and the detection step can include or use a plurality of detectable particles, for example, fluorescent particles. The particles can be used as part of a positive control system to ensure that one or more of the cell capture system, the cell capture method, the detection system, and the method of detecting the viable cells are operating correctly. The fluorescent particles can be adapted to be excited by light having a wavelength at least in a range from about 350 nm to about 1000 nm. For example, the wavelength is at least in one range from about 350 nm to about 600 nm, from about 400 nm to about 650 nm, from about 450 nm to about 700 nm, from about 500 nm to about 750 nm, from about 550 nm to about 800 nm, from about 600 nm to about 850 nm, from about 650 nm to about 900 nm, from about 700 nm to about 950 nm, from about 750 to about 1000 nm. Certain ranges include from about 350 nm to about 600 nm and from out 600 nm to about 750 nm.

Depending upon the design of the cell capture system, the particles can be pre-disposed upon at least a portion of the porous membrane or disposed within a well formed in a mask associated with the membrane. Alternatively, the particles (for example, the fluorescent particles) can be mixed with a liquid sample prior to passing the sample through the porous membrane. In such an approach, the fluorescent particles can be dried in a vessel that the sample of interest is added to. Thereafter, the particles can be resuspended and/or dispersed within the liquid sample. Alternatively, the fluorescent particles can be present in a second solution that is mixed with the sample of interest. Thereafter, the particles can dispersed within the liquid sample. The particles, for example, a plurality of particles, can then be captured on the porous membrane along with the cells in the cell sample, which acts as a positive control for the cell capture system. The particles, for example, the fluorescent particles, can be detected once they emit a fluorescent event upon activation by light from the light source.

Using the staining protocols described herein, it is possible to determine the number of viable cells in at least a portion of the cell sample, for example, a liquid sample. The liquid sample can be, for example, a water sample, a comestible fluid (e.g., wine, beer, milk, baby formula or the like), a body fluid (e.g., blood, lymph, urine, cerebrospinal fluid or the like), growth media, a liquid sample produced by harvesting cells from a source of interest (e.g., via a swab) and then dispersing and/or suspending the harvested cells, if any, a liquid sample, for example, buffer or growth media. Furthermore, the detection system can be used to determine the location(s) of the viable cells on the permeable membrane, as described above.

After the detection step, the viable cells can be cultured under conditions that permit growth and/or proliferation of the viable cells (e.g., microorganisms) captured by the porous membrane. The genus and/or species of the viable organisms can be determined by standard procedures, for example, microbiological staining and visualization procedures, or molecular biological procedures, for example, amplification procedures including polymerase chain reaction, ligase chain reaction, rolling circle replication procedures, and the like, and by nucleic acid sequencing.

EXAMPLES

The invention now being generally described, will be more readily understood by reference to the following examples, which are included merely for purposes of illustration of certain aspects and embodiments of the present invention, and are not intended to limit the scope of the invention in any way.

Example 1—Imaging of Viable and Non-Viable E. coli on a Solid Support Using a Fluorescent Probe and a Quencher Wash This Example demonstrates that it is possible to selectively stain and image viable bacteria (E. coli) on a solid support using a fluorescent probe and a single quencher wash.

Viable and non-viable E. coli cell fractions were prepared by picking a colony cultured on a conventional media plate and then transferring the cells into Phosphate Buffered Saline (PBS). The cells then were suspended by vortexing and then were further diluted in PBS to give a turbidity equivalent to a 1.0 McFarland standard. This stock solution served as the live cell fraction. An aliquot of the live cell fraction was transferred to a glass tube that was placed into a boiling water bath for about 15 minutes to heat kill the E. coli. The tube was removed from the bath and allowed to cool to room temperature. This heat killed suspension served as the dead cell fraction.

A fluorescent stain solution was prepared as a 0.005 mM solution of Oxazine 170 perchlorate (Sigma-Aldrich, St. Louis, Mo.) in PBS containing a 1:100,000 dilution of 10% w/v 0.8 μm Sky Blue latex fluorescent particles (Spherotech, Lake Forest, Ill.). A separate quencher wash solution was prepared as a 10 mM Sodium ascorbate (Sigma-Aldrich, St. Louis, Mo.) solution in PBS.

The live and dead cell fractions were diluted separately 1:1000 into 10 mL PBS and filtered through separate 0.2 μm black CYCLOPORE® membranes (Whatman, Sanford, Me.) to capture the cells on each membrane using a vacuum system. Both membranes were then stained for about 3 minutes with 5 mL of the stain solution which was then filtered through the membrane. Each membrane was then rinsed with a 10 mL fraction of quencher wash.

Figure 19A:
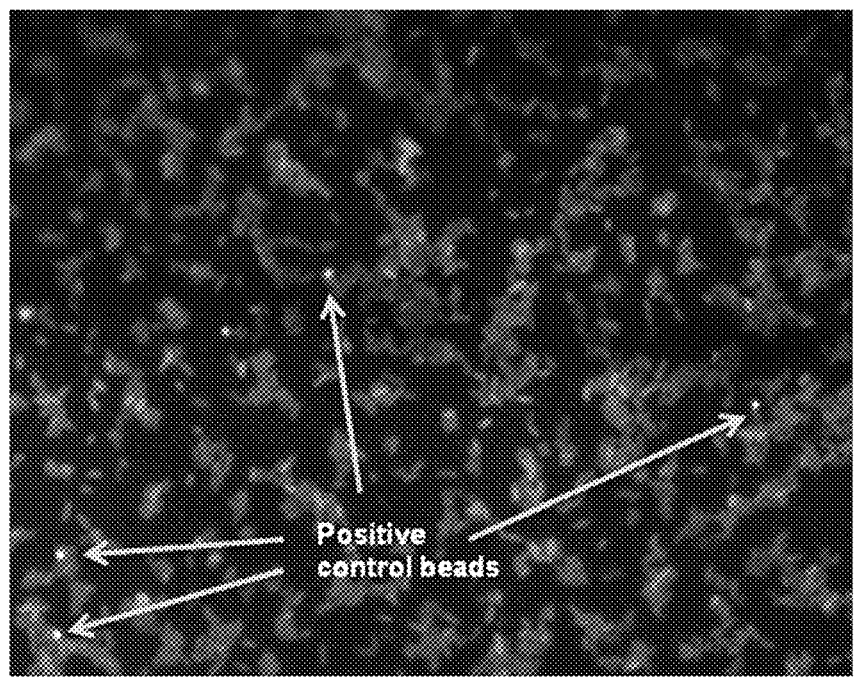
FIGS. 19A and 19B are pictorial representations of viable cells and non-viable cells, respectively, with positive control beads depicted in each figure.
Figure 19B:
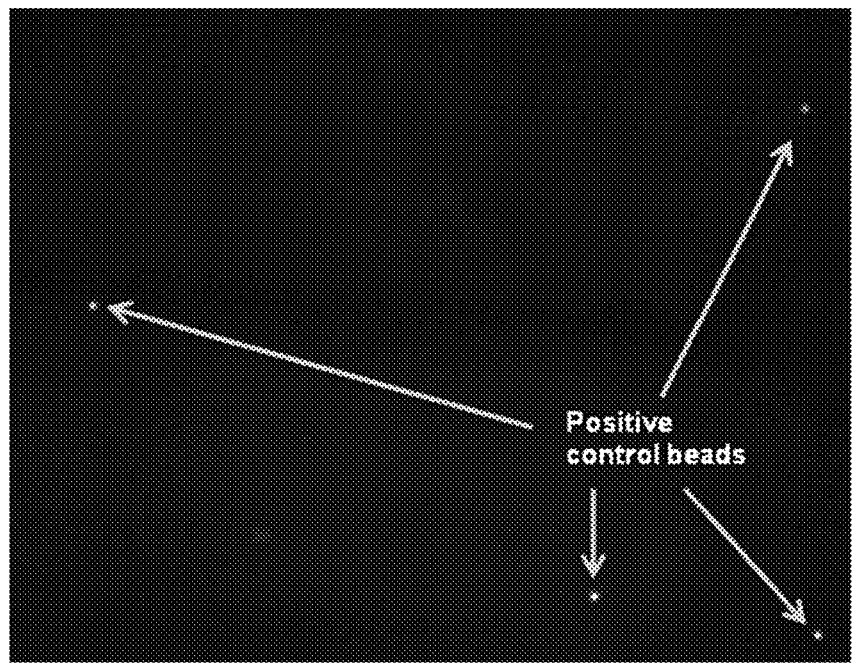

The cells then were imaged using a fluorescent microscope (Carl Zeiss, LLC—Thornwood, N.Y.) with an excitation of 575 nm-625 nm and measured emission of 660 nm-710 nm. FIG. 19A is a fluorescent image showing the live cell population. In the viable cells, the impermeable quencher (sodium ascorbate) was excluded from the viable cells. As a result, the viable cells were stained brightly, as were the fluorescent latex particles, which acted as a positive control. FIG. 19B shows an image created using the heat killed cells. The heat killed cells were permeated by the ascorbate quencher, which resulted in the quenching of the fluorescent signal and a loss of fluorescence. The positive control latex particles can be seen in FIG. 19B, which validates that the membrane functioned to capture the particles, the surface of the membrane was in focus, and the image had been captured under equivalent lighting conditions and parameters.

Example 2—Discrimination of Viable and Non-Viable E. coli Cells Using a Fluorescent Probe and Two Photo-Induced Electron Transfer (PET) Quenchers This Example demonstrates that it is possible to selectively stain and image viable bacteria (E. coli) in solution with a fluorescent probe and two PET quenchers.

The viable and heat killed E. coli were preparations were prepared as described in Example 1. The heat killed E. coli suspension was then combined with the viable cell suspension and mixed by vortexing. The resulting cell suspension served as the viable and non-viable E. coli solution.

A fluorescent probe-quencher stain was prepared as a solution consisting of 0.005 mM Oxazine 170 perchlorate (Sigma-Aldrich, St. Louis, Mo.), 0.4 mM p-Sulfonic calix[6]arene (TCI America, Portland, Oreg.), 100 mM Sodium ascorbate (Sigma-Aldrich, St. Louis, Mo.) in PBS.

The viable and non-viable E. coli suspension was then diluted 1:1000 into the fluorescent probe-quencher solution to stain the cells. After incubation for approximately 5 minutes, a droplet of the stained cell solution was placed onto a microscope slide and imaged on a fluorescent microscope (Carl Zeiss, LLC, Thornwood, N.Y.).

Figures 20A, 20B:
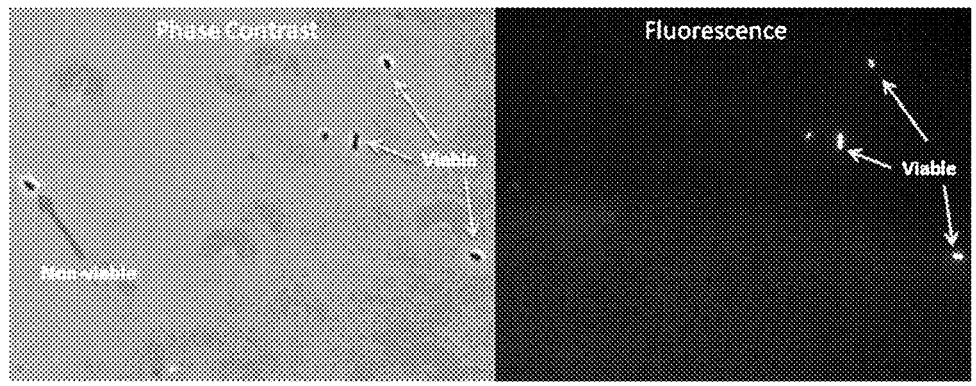
FIGS. 20A and 20B depict phase contrast and fluorescence images, respectively, for viable and non-viable cells using an exemplary viability staining system.

FIGS. 20A and 20B show a combined image of the viable and non-viable stained E. coli captured under phase contrast (FIG. 20A) as well as fluorescent conditions (excitation 575-625 nm, emission 660-710 nm) (FIG. 20B). The viable and non-viable cells were indistinguishable in phase contrast but under fluorescent conditions the viable cells were brightly fluorescent whereas the non viable cells were not. The membrane impermeable quenchers, p-Sulfonic calix[6]arene and sodium ascorbate, permeated the non-viable cell membranes resulting in an effective quenching of fluorescence.

Example 3—Discrimination Between Viable and Non-Viable E. coli Using a Fluorescent Probe, a Photo-Induced Electron Transfer (PET) Quencher, and a Fluorescence Resonance Energy Transfer (FRET) Quencher This Example demonstrates that it is possible to selectively stain and image viable bacteria (E. coli) in solution with a fluorescent probe and a combination of a PET quencher and FRET quencher.

A cell suspension containing both viable and non-viable E. coli cells was produced as described in Example 2. A fluorescent probe-quencher stain was prepared as a solution consisting of 0.005 mM Oxazine 170 perchlorate (Sigma-Aldrich, St. Louis, Mo.), 0.2 mM IR-783 (Sigma-Aldrich, St. Louis, Mo.), 100 mM 5'Guanosine monophosphate (Sigma-Aldrich, St. Louis, Mo.) in PBS.

The viable and non-viable E. coli suspension was then diluted 1:1000 into the fluorescent probe-quencher solution to stain the cells. After an incubation of approximately 5 minutes, a droplet of the stained cell solution was placed onto a microscope slide and imaged on a fluorescent microscope (Carl Zeiss, LLC, Thornwood, N.Y.).

Figures 21A, 21B:
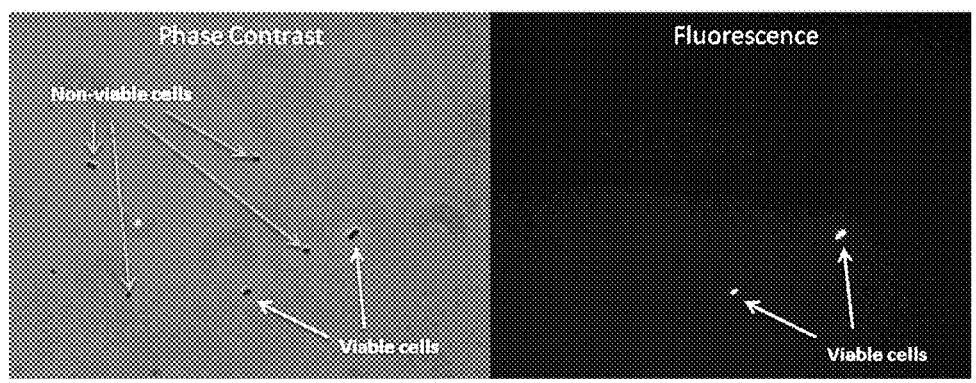
FIGS. 21A and 21B are phase contrast and fluorescence images, respectively, for viable and non-viable cells using an exemplary viability staining system.

FIGS. 21A and 21B show a combined image of the viable and non-viable stained E. coli captured under phase contrast (FIG. 21A) as well as fluorescent conditions (excitation 575-625 nm, emission 660-710 nm) (FIG. 21B). The viable and non-viable cells were indistinguishable in phase contrast, but under fluorescent conditions the viable cells were brightly fluorescent, whereas the non-viable cells were not. The membrane impermeable quenchers permeated the non-viable cell membranes resulting in an effective quenching of fluorescence.

Example 4—Imaging of Viable Microbes (*E. coli* and *Candida albicans*) on a Rotating Membrane Using a Fluorescent Probe and a Quencher Wash This Example demonstrates that it is possible to selectively stain and image viable microbes with a fluorescent probe and a quencher wash on using a detection system shown schematically in FIG. 1A.

A solution of viable microbes was prepared by combining a 550 CFU Bioball of *E. coli* and a 550 CFU Bioball of *Candida albicans* (bioMerieux Durham, N.C.) in a PBS solution. The solution was vortexed briefly to suspend the cells. The suspension then was filtered through a 0.2 µm black CYCLOPORE® membrane (Whatman Sanford, Me.) by using a vacuum system to capture the cells on the membrane. The cells were captured upon a porous membrane disposed upon a porous support member, for example, as shown in FIGS. 4A and 4B, by passing the solution through the membrane and porous support member.

A fluorescent stain solution was prepared as a 0.005 mM solution of Oxazine 170 perchlorate (Sigma-Aldrich, St. Louis, Mo.) in PBS. A separate quencher wash solution was prepared as a 50 mM Sodium ascorbate (Sigma-Aldrich, St. Louis, Mo.) solution in PBS. The captured cells were then incubated with 5 mL of the stain solution for about 5 minutes. The stain was filtered through the membrane and followed with 20 mL of quencher wash solution.

Figure 22:
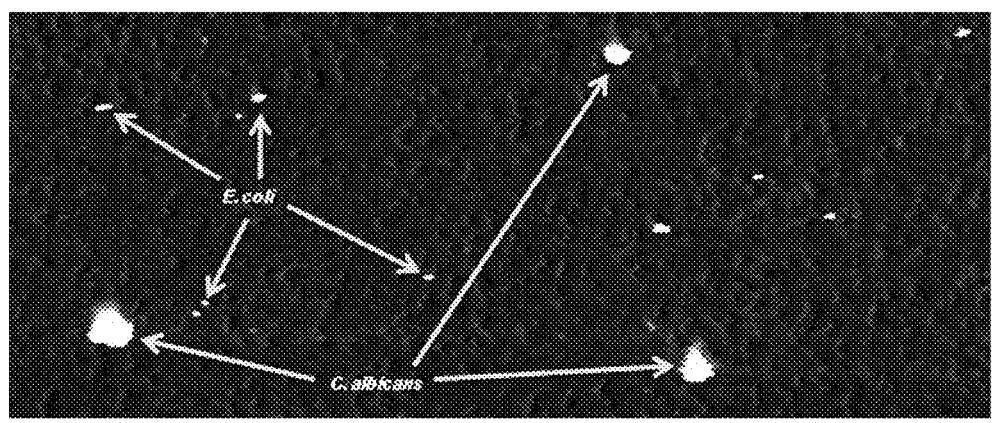
FIG. 22 is an image of viable cells (*E. coli* and *Candida albicans*) captured on a permeable membrane, stained with an exemplary viability staining system and detected as fluorescent events on a rotating disc using the detection system shown of FIG. 1A.

The resulting membrane then was transferred to the platform of a detection system shown schematically in FIG. 1. The membrane was rotated at 5 revolutions per second, and the fluorescent events were detected via the detection system. FIG. 22 shows a small portion of the scanned surface in which the viable populations of *E. coli* and *C. albicans* are clearly visible as bright fluorescent events.

Example 5—Discrimination Between Viable and Non-Viable Microorganisms Using a Nucleic Acid Binding Fluorescent Probe and a Nucleic Acid Binding Quencher This example demonstrates that it is possible to selectively stain and image viable microorganisms (*E. coli, S. aureus, C. albicans*) by using a nucleic acid binding membrane permeable fluorescent dye paired with a nucleic acid binding membrane impermeable quencher.

Cell suspensions of viable and non-viable *E. coli, S. aureus*, and *C. albicans* were prepared by picking colonies of each respective microorganism from a conventional cultured media plate and transferring the cells into separate glass tubes containing 0.9% (w/v) NaCl. The cells then were suspended by vortexing and then were further diluted in saline to give a turbidity equivalent to a 2.0 McFarland standard. These suspensions served as the live cell fractions. An aliquot of each live cell fraction was transferred to a separate glass tube that was then placed into a heat block at 80° C. for 2 hours. The tube was removed from the bath and allowed to cool to room temperature. These heat killed cell suspensions served as the dead cell fractions.

Quencher Q16 can be prepared according to a modified method from Beletskaya et. al. (2005) *Eur. J. Org. Chem.* 2005, 381-305. Briefly. 1 mmol of 1,4,5,8-tetrachloroanthraquinone (Pure Chemistry Scientific, Sugarland, Tex.), 0.08 mmol of tris(dibenzylideneacetone)dipalladium (0) (Sigma-Aldrich, St. Louis, Mo.), 0.16 mmol of 2,2'-bis(diphenylphosphino)-1'-binaphthyl (Sigma-Aldrich, St. Louis, Mo.), 5 mmol of 3-(dimethylamino)-1-propylamine (Sigma-Aldrich, St. Louis, Mo., and 5 mmol of caesium carbonate (Sigma-Aldrich, St. Louis, Mo.) is combined into 5 mL of dioxane (Sigma-Aldrich, St. Louis, Mo.). The mixture is stirred under nitrogen in a sealed vessel at 100° C. for 24 hrs. The resulting suspension is filtered and the filtrate diluted into 100 mL of 5% (w/v) aqueous potassium carbonate. The resulting precipitate can be collected by centrifugation. The resulting pellet can then be dissolved in 5 mL of 1-methyl-2-pyrrolidinone (Sigma-Aldrich, St. Louis, Mo.) and the alkyl amines quaternized by mixing in an excess molar amount of methyl p-toluenesulfonate (Sigma-Aldrich, St. Louis, Mo.) and stirring at 60° C. for 6 hrs. The solution is diluted into 100 mL of acetone (Sigma-Aldrich, St. Louis, Mo.) and the crude product precipitated as a Hue solid, and can be used as is.

Quencher Q17 can be prepared based on a modified version of the synthetic procedures described in U.S. Pat. No. 5,342,974. Briefly, 1 mmol of 1,4,5,8-Tetrachloroanthraquinone (Pure Chemistry Scientific, Sugarland, Tex.), 0.10 mmol of copper sulfate (Sigma-Aldrich, St. Louis, Mo.), 5 mmol benzyl alcohol (Sigma-Aldrich, St. Louis, Mo.), 5 mmol potassium acetate (Sigma-Aldrich, St. Louis, Mo.), and 5 mmol of 3-(dimethylamino)-1-propylaraine (Sigma-Aldrich, St. Louis, Mo.) are combined into 10 mL of 2-ethoxyethanol (Sigma-Aldrich, St. Louis, Mo.). The stirred mixture is then heated at 130° C. under nitrogen in a sealed vessel for 10 hours. The resulting suspension can be filtered and the resulting filtrate diluted into 100 ml, of 5% w/v aqueous potassium carbonate. The resulting precipitate can be collected by centrifugation. The pellet is dissolved into 5 mL of 1-methyl-2-pyrrolidinone (Sigma-Aldrich, St. Louis, Mo.) and the alkyl amines quaternized by mixing in an excess molar amount of methyl p-toluenesulfonate (Sigma-Aldrich, St. Louis, Mo.) and stirring at 60° C. for 6 hrs. The solution is diluted into 100 mL of acetone (Sigma-Aldrich, St. Louis, Mo.) and the crude product precipitated as a blue-green solid.

Quencher Q18 can be prepared according to the combined methods from F. Y. Kwong, et. al. (2002) *Org. Lett.*, Vol. 4, No. 4, 581-584 and Griffiths, et. al. (1999) *Dyes and Pigments*, 42, 29-34). Briefly, 1 mmol of iodobenzene (Sigma-Aldrich, St. Louis, Mo.), 1.1 mmol of N,N,N'-trimethyl-1,3-propanediaraine (Sigma-Aldrich, St. Louis, Mo.), 2 mmol ethylene glycol (Sigma-Aldrich, St. Louis, Mo.), 0.10 mmol copper (I) iodide (Sigma-Aldrich, St. Louis, Mo.), and 2 mmol of tripotassium phosphate (Sigma-Aldrich, St. Louis, Mo.) are combined into 5 mL of isopropanol (Sigma-Aldrich, St. Louis, Mo.). The reaction mixture is refluxed for 24 hrs, cooled to room temperature and filtered. The solvents are evaporated under reduced pressure. Half of the crude product is dissolved into concentrated HCl (Sigma-Aldrich, St. Louis, Mo.) in a cooled ice bath. To the solution is added a stoichiometric amount of sodium nitrite (Sigma-Aldrich, St. Louis, Mo.), keeping the temperature under 5° C. The mixture then is stirred for 1 hr and a saturating amount of sodium chloride (Sigma-Aldrich, St. Louis, Mo.) is added. The nitrosylated product precipitated can be collected by filtration.

A stoichiometric amount of the nitrosylated fraction is combined with the non-nitrosylated fraction in acetic anhydride and stirred at room temperature until judged to be complete by T.L.C. analysis. The product is collected by precipitation in diethyl ether (Sigma-Aldrich, St. Louis, Mo.). The precipitate then is resuspended in 1-methyl-2-pyrrolidinone (Sigma-Aldrich, St. Louis, Mo.) and the alkyl amines quaternized by mixing in an excess molar amount of methyl p-toluenesulfonate. The mixture is reacted for 8 hours at room temperature and then the product is collected by precipitation in diethyl ether (Sigma-Aldrich, St. Louis, Mo.) as a dark green solid.

Fluorescent dye-quencher solutions (see TABLE V, which refers to dyes and quenchers identified in TABLES I and II, respectively) were formulated at a concentration of 5 µM fluorescent dye and 50 µM quencher in 0.9% (w/v) NaCl. An aliquot from a live cell fraction of one species, and an aliquot from a dead cell fraction of another species were combined into the fluorescent dye-quencher solution such that the each fraction was diluted 1:100 from its respective stock concentration. The resulting mixed cell suspension then was incubated at room temperature for approximately five minutes to stain the cells. A droplet of the stained cell solution then was placed onto a microscope slide and imaged on a fluorescence microscope (Carl Zeiss, LLC—Thornwood, N.Y.) utilizing the excitation/emission filters appropriate for each fluorescent dye. The fluorescent dyes and quencher pairs, the excitation/emission filters used, and the microorganisms tested in each entry summarized in TABLE V.

TABLE V

| Expt No. | Fluorescent Dye | Quencher | Live/Dead Microorganism Mix | Excitation/Emission Filters (nm) |
|---|---|---|---|---|
| 1 | D9 | Q19 | Live - *E. coli* Dead - *S. aureus* | Ex. - 365 nm Em. - 420-470 nm |
| 2 | D10 | Q19 | Live - *C. albicans* Dead - *E. coli* | Ex. - 365 nm Em. - 420-470 nm |
| 3 | D18 | Q16 | Live - *S. aureus* Dead - *E. coli* | Ex. - 575-625 nm Em. - 660-710 nm |
| 4 | D26 | Q16 | Live - *E. coli* Dead - *S. aureus* | Ex. - 575-625 nm Em. - 660-710 nm |
| 5 | D42 | Q16 | Live - *E. coli* Dead - *S. aureus* | Ex. - 575-625 nm Em. - 660-710 nm |

Figures 23A, 23B:
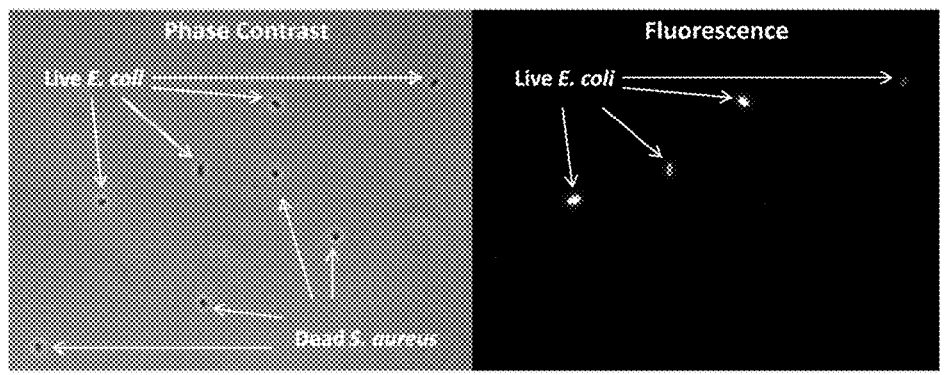
FIGS. 23A-J are phase contrast and fluorescence images of mixed population of viable and non-viable microorganisms stained with exemplary pairs of nucleic acid binding fluorescent dyes and a nucleic acid binding fluorescence quenchers.
Figures 23C, 23D:
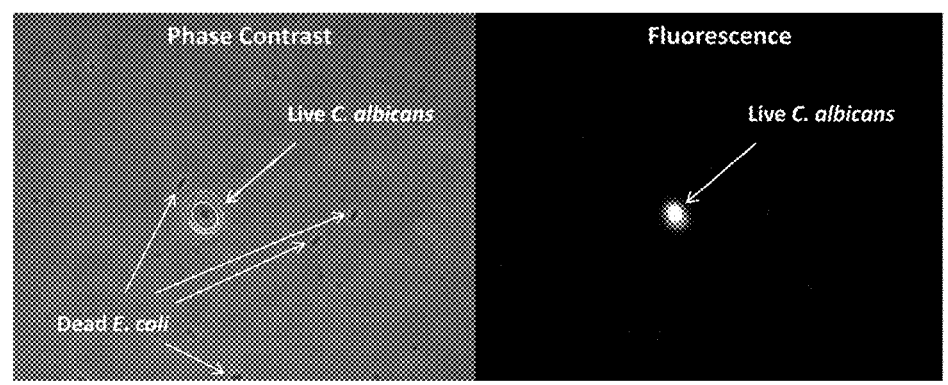
Figures 23E, 23F:
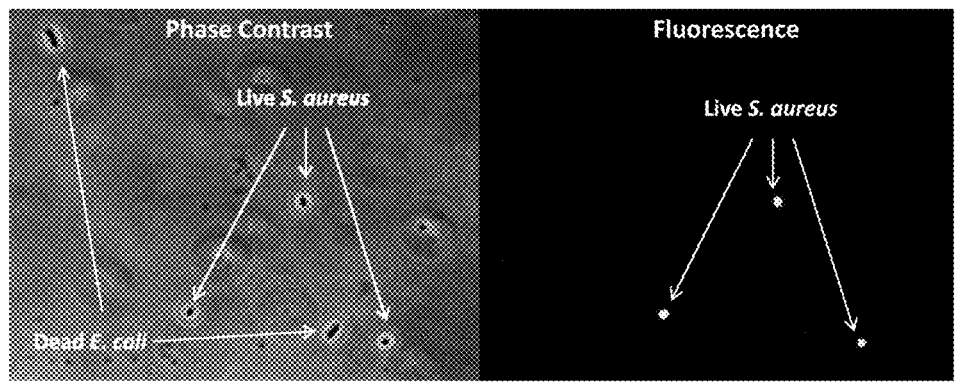
Figures 23G, 23H:
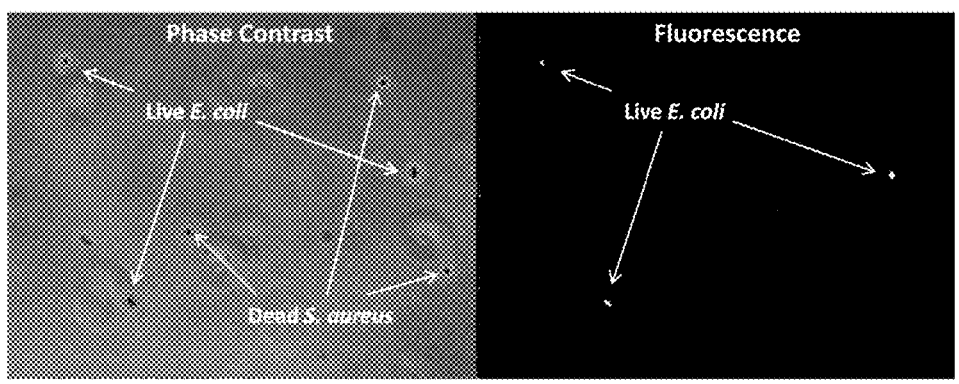
Figures 23I, 23J:
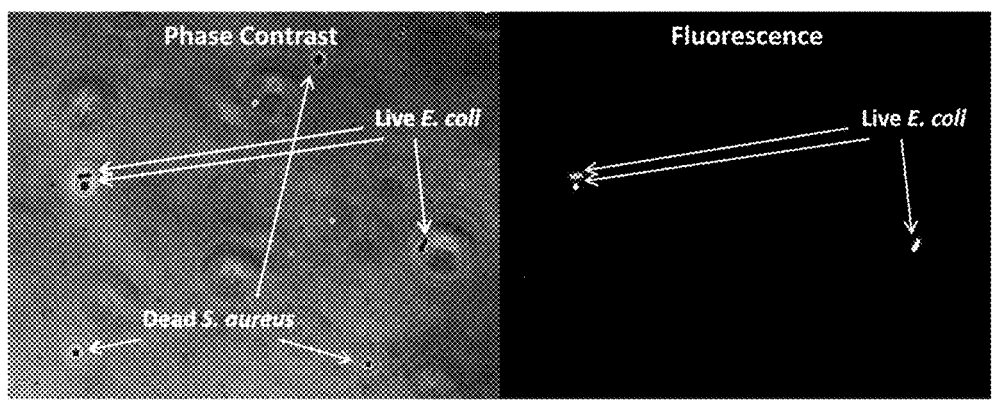

The captured images, both phase contrast and fluorescent, for each fluorescent dye-quencher pair set forth in TABLE V are shown in FIGS. 23A-J, where FIGS. 23A and B correspond to phase contrast and fluorescence images, respectively, for Experiment 1, FIGS. 23C and D correspond to phase contrast and fluorescence images, respectively, for Experiment 2, FIGS. 23E and F correspond to phase contrast and fluorescence images, respectively, for Experiment 3, FIGS. 23G and H correspond to phase contrast and fluorescence images, respectively, for Experiment 4, and FIGS. 23I and J correspond to phase contrast and fluorescence images, respectively, for Experiment 5. In each experiment, the membrane impermeable nucleic acid binding quencher was excluded by the intact cellular membrane of a viable cell resulting in brightly fluorescent, easily distinguishable population of viable cells. The dead cells however, were permeated by the nucleic acid binding quencher thus allowing the co-binding of fluorescent dye and quencher to nucleic acids in the dead cells resulting in a dark non-fluorescent complex.

Example 6—Imaging of Viable Microbes Using a Nucleic Acid Binding Fluorescent Probe and a Nucleic Acid Binding Quencher This example demonstrates that it is possible to selectively stain and image viable microorganisms (*E. coli* and *S. aureus*) by using a nucleic acid binding membrane permeable fluorescent dye paired with a nucleic acid binding membrane impermeable quencher and then image the viable cells using either an epifluorescent microscope or a detection system described herein where viable cells are detected on a rotating membrane.

Cell suspensions of viable and non-viable *E. coli* and *S. aureus* were prepared by picking colonies of each respective microorganism from a conventional cultured media plate and transferring the cells into separate glass tubes containing 0.9% (w/v) NaCl. The cells then were suspended by vortexing and then were further diluted in saline to give a turbidity equivalent to a 2.0 McFarland standard. These suspensions served as the live cell fractions. An aliquot of each live cell fraction was transferred to a separate glass tube that was then placed into a heat block at 80° C. for 2 hours. The tube was removed from the bath and allowed to cool to room temperature. These heat killed cell suspensions served as the dead cell fractions.

Fluorescent dye-quencher solutions (see, TABLE VI, which refers to dyes and quenchers identified in TABLES I and II, respectively) were formulated at a concentration of 5 µM fluorescent dye and 50 µM quencher in 10 µM Tris, 0.9% (w/v) NaCl, pH 7.4. For experiment numbers 1 and 2 in TABLE VI, an aliquot from a live cell fraction of one species, and an aliquot from a dead cell fraction of another species were combined into the fluorescent dye-quencher solution such that the each fraction was diluted 1:100 from its respective stock concentration. The resulting mixed cell suspension then was incubated at room temperature for approximately fifteen minutes to stain the cells. A droplet of the stained cell solution then was placed onto a microscope slide and imaged on a fluorescence microscope (Carl Zeiss, LLC—Thornwood, N.Y.) utilizing the excitation/emission filters appropriate for each fluorescent dye.

To image the viable microorganisms on a rotating membrane, an aliquot from the live cell fraction of *E. coli* and an aliquot from the dead cell fraction of *S. aureus* were suspended in a solution of 10 µM Tris, 0.9% (w/v) NaCl, pH 7.4 and then filtered through an assembly depicted in FIG. 10A that contained a gold sputtered PET 0.45 µm membrane. The cells captured on the membrane were then exposed to a 2 mL volume of fluorescent dye and quencher solution (see, TABLE VI, Experiment No. 3) and incubated at room temperature for fifteen minutes to stain the cells. The stain solution was evacuated by vacuum filtration and the assembly depicted in FIG. 10C was placed into a holder depicted in FIG. 14A and then imaged with a detection system depicted in FIG. 1A where the membrane was rotated at a speed of about 5 revolutions per second (300 revolutions per minute). The fluorescent dyes and quencher pairs, the excitation/emission filters used, and the microorganisms tested in each experiment are summarized in TABLE VI.

TABLE VI

| Exp. No. | Fluorescent Dye | Quencher | Live/Dead Microorganism Mix | Excitation/Emission Filters (nm) |
|---|---|---|---|---|
| 1 | D16 | Q17 | Live - *S. aureus* Dead - *E. coli* | Ex. - 575-625 nm Em. - 660-710 nm |
| 2 | D17 | Q17 | Live - *E. coli* Dead - *S. aureus* | Ex. - 575-625 nm Em. - 660-710 nm |
| 3 | D17 | Q17 | Live - *E. coli* Dead - *S. aureus* | Ex. - 640 nm Em. - 660 nm-690 nm |

Figure 24E:
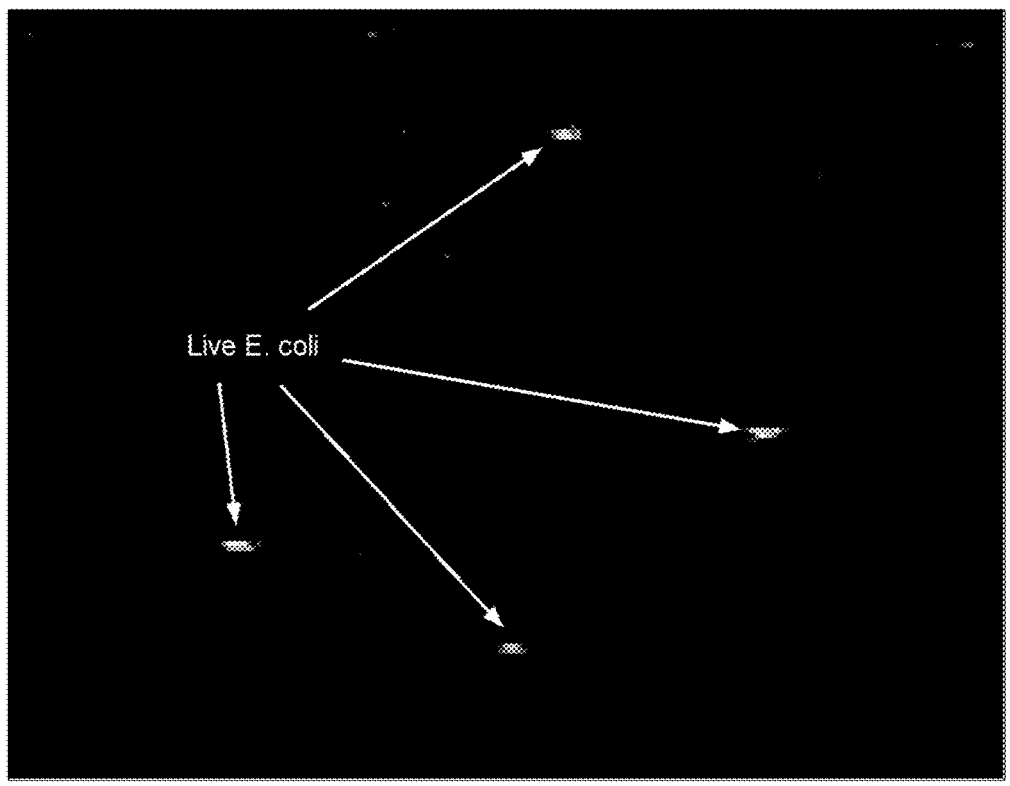

The captured images, both phase contrast and fluorescent, for each fluorescent dye-quencher pair set forth in TABLE VI, are set forth in FIG. 24, where FIGS. 24A and B correspond to phase contrast and fluorescence images, respectively, for Experiment 1, FIGS. 24C and D correspond to phase contrast and fluorescence images, respectively, for Experiment 2, and FIG. 24E corresponds to the fluorescence image for Experiment 3. In each experiment, regardless of the imaging technique (via epifluorescent microscope or detection by a system depicted in FIG. 1A), the membrane impermeable nucleic acid binding quencher was excluded by the intact cellular membrane of a viable cell resulting in brightly fluorescent, easily distinguishable population of viable cells. The dead cells, however, were permeated by the nucleic acid binding quencher resulting in a dark, non-fluorescent complex.

INCORPORATION BY REFERENCE

The entire disclosure of each of the patent documents and scientific articles referred to herein is incorporated by reference for all purposes. The entire description of U.S. Provisional Patent Application Ser. Nos. 61/641,805; 61/641,809; 61/641,812; 61/784,759; 61/784,789; and 61/784,807 are incorporated by reference herein for all purposes.

EQUIVALENTS

The invention may be embodied in other specific forms without departing from the spirit or essential characteristics thereof. The foregoing embodiments are therefore to be considered in all respects illustrative rather than limiting the invention described herein. Various structural elements of the different embodiments and various disclosed method steps may be utilized in various combinations and permutations, and all such variants are to be considered forms of the invention. Scope of the invention is thus indicated by the appended claims rather than by the foregoing description, and all changes that come within the meaning and range of equivalency of the claims are intended to be embraced therein.

What is claimed is:

1. A cell capture system comprising:
   (a) a fluid permeable, planar membrane comprising an exposed first surface and a second opposing surface, at least a portion of the first surface is adapted to retain cells thereon, the portion:
       (i) defining a plurality of pores having an average diameter less than about 1 µm so as to permit fluid to traverse the portion of the membrane while retaining cells thereon;
       (ii) being substantially non-autofluorescent when exposed to light having a wavelength in a range from about 350 nm to about 1000 nm; and
       (iii) having a flatness tolerance of up to about 100 µm when a fluid sample has passed through the membrane;
   (b) a fluid permeable support member adjacent and supporting at least a portion of the second opposing surface of the membrane, the fluid permeable support member comprising an upper surface that contacts the second opposing surface of the membrane and has a flatness tolerance of up to about 100 µm so as to maintain the flatness tolerance of the portion of the membrane when the fluid sample has passed through the membrane; and
   (c) an optional register associated with the membrane.

2. The system of claim 1, wherein the membrane comprises a disc.

3. The system of claim 2, wherein the disc has a thickness in a range selected from the group consisting of: from 1 µm to 3,000 µm; from 10 µm to 2,000 µm; and from 100 µm to 1,000 µm.

4. The system of claim 1, wherein the support member has a thickness in a range selected from the group consisting of: from 0.1 mm to 10 mm; from 0.5 mm to 5 mm; and from 1 mm to 3 mm.

5. The system of claim 1, further comprising a mask proximate at least another portion of the first surface of the membrane.

6. The system of claim 5, wherein the mask is circular.

7. The system of claim 1, further comprising a plurality of detectable particles.

8. The system of claim 7, wherein the particles are fluorescent particles.

9. The system of claim 8, wherein the particles are adapted to be excited by light having a wavelength at least in a range from about 350 nm to about 1000 nm.

10. The system of claim 9, wherein the particles are adapted to be excited by light having a wavelength at least in one range from about 350 nm to about 600 nm and from about 600 nm to about 750 nm.

11. The system claim 1 having a sterility assurance level less than $10^{-6}$, $10^{-7}$, $10^{-8}$, or $10^{-9}$.

12. A cell capture system comprising:
   (a) a fluid permeable, planar membrane comprising an exposed first surface and a second opposing surface, at least a portion of the first surface is adapted to retain cells thereon, the portion:
       (i) defining a plurality of pores having an average diameter less than about 1 µm so as to permit fluid to traverse the portion of the membrane while retaining cells thereon;
       (ii) being substantially non-autofluorescent when exposed to light having a wavelength in a range from about 350 nm to about 1000 nm; and
       (iii) having a flatness tolerance of up to about 100 µm when a fluid sample has passed through the membrane;
   (b) a fluid permeable support member adjacent and supporting at least a portion of the second opposing surface of the membrane, the fluid permeable support member comprising an upper surface that contacts the second opposing surface of the membrane and has a flatness tolerance of up to about 100 µm so as to maintain the flatness tolerance of the portion of the membrane when the fluid sample has passed through the membrane;
   (c) an optional register associated with the membrane; and
   (d) a mask comprising a plurality of detectable particles disposed within a well defined by the mask.

* * * * *